(12) United States Patent
Kesteleyn et al.

(10) Patent No.: US 10,029,984 B2
(45) Date of Patent: Jul. 24, 2018

(54) MONO- OR DI-SUBSTITUTED INDOLE DERIVATIVES AS DENGUE VIRAL REPLICATION INHIBITORS

(71) Applicants: Janssen Pharmaceuticals, Inc., Titusville, NJ (US); Katholieke Universiteit Leuven, Leuven (BE)

(72) Inventors: Bart Rudolf Romanie Kesteleyn, Berlare (BE); Jean-François Bonfanti, Ande (FR); Tim Hugo Maria Jonckers, Heist-op-den-Berg (BE); Pierre Jean-Marie Bernard Raboisson, Rosieres (BE); Dorothée Alice Marie-Eve Bardiot, Heverlee (BE); Arnaud Didier M Marchand, Bierbeek (BE)

(73) Assignees: Janssen Pharmaceuticals, Inc., Titusville, NJ (US); Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 15/542,735

(22) PCT Filed: Jan. 15, 2016

(86) PCT No.: PCT/EP2016/050715
§ 371 (c)(1),
(2) Date: Jul. 11, 2017

(87) PCT Pub. No.: WO2016/113371
PCT Pub. Date: Jul. 21, 2016

(65) Prior Publication Data
US 2018/0002282 A1 Jan. 4, 2018

(30) Foreign Application Priority Data
Jan. 16, 2015 (EP) .................... 15151481

(51) Int. Cl.
*A01N 43/38* (2006.01)
*A61K 31/40* (2006.01)
*C07D 209/14* (2006.01)
*A61K 31/4045* (2006.01)

(52) U.S. Cl.
CPC ........ *C07D 209/14* (2013.01); *A61K 31/4045* (2013.01); *C07B 2200/13* (2013.01)

(58) Field of Classification Search
CPC ........................ A61K 31/404; C07D 209/12
USPC ........................................ 514/419; 548/493
See application file for complete search history.

(56) References Cited

FOREIGN PATENT DOCUMENTS

WO WO 2013/045516 4/2013

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*

* cited by examiner

*Primary Examiner* — Jeffrey H Murray
(74) *Attorney, Agent, or Firm* — Andrea Jo Kamage

(57) ABSTRACT

The present invention relates to mono- or di-substituted indole compounds, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

5 Claims, No Drawings

SEQUENCE LISTING

```
<160> NUMBER OF SEQ ID NOS: 6

<210> SEQ ID NO 1
<211> LENGTH: 19
<212> TYPE: DNA
<213> ORGANISM: Dengue virus
<220> FEATURE:
<221> NAME/KEY: source
<222> LOCATION: 1..19
<223> OTHER INFORMATION: /organism="Dengue virus"
      /mol_type="unassigned DNA"

<400> SEQUENCE: 1
cggttagagg agacccctc                                                  19

<210> SEQ ID NO 2
<211> LENGTH: 21
<212> TYPE: DNA
<213> ORGANISM: Dengue virus
<220> FEATURE:
<221> NAME/KEY: source
<222> LOCATION: 1..21
```

```
<223> OTHER INFORMATION: /organism="Dengue virus"
      /mol_type="unassigned DNA"

<400> SEQUENCE: 2
gagacagcag gatctctggt c                                              21

<210> SEQ ID NO 3
<211> LENGTH: 28
<212> TYPE: DNA
<213> ORGANISM: Dengue virus
<220> FEATURE:
<221> NAME/KEY: source
<222> LOCATION: 1..28
<223> OTHER INFORMATION: /organism="Dengue virus"
      /mol_type="unassigned DNA"

<400> SEQUENCE: 3
aaggactaga ggttagagga gaccccccc                                      28

<210> SEQ ID NO 4
<211> LENGTH: 18
<212> TYPE: DNA
<213> ORGANISM: Dengue virus
<220> FEATURE:
<221> NAME/KEY: source
<222> LOCATION: 1..18
<223> OTHER INFORMATION: /organism="Dengue virus"
      /mol_type="unassigned DNA"

<400> SEQUENCE: 4
ggccaggtca tcaccatt                                                  18

<210> SEQ ID NO 5
<211> LENGTH: 21
<212> TYPE: DNA
<213> ORGANISM: Dengue virus
<220> FEATURE:
<221> NAME/KEY: source
<222> LOCATION: 1..21
<223> OTHER INFORMATION: /organism="Dengue virus"
      /mol_type="unassigned DNA"

<400> SEQUENCE: 5
atgtccacgt cacacttcat g                                              21

<210> SEQ ID NO 6
<211> LENGTH: 21
<212> TYPE: DNA
<213> ORGANISM: Dengue virus
<220> FEATURE:
<221> NAME/KEY: source
<222> LOCATION: 1..21
<223> OTHER INFORMATION: /organism="Dengue virus"
      /mol_type="unassigned DNA"

<400> SEQUENCE: 6
ttccgctgcc ctgaggctct c                                              21
```

MONO- OR DI-SUBSTITUTED INDOLE DERIVATIVES AS DENGUE VIRAL REPLICATION INHIBITORS

This application is a national stage application of PCT/EP2016/050715, filed Jan. 15, 2016, which claims priority benefit of Application No. EP 15151481.7 filed Jan. 16, 2015. The complete disclosures of the aforementioned related patent applications are hereby incorporated herein by reference for all purposes.

The present invention relates to mono- or di-substituted indole compounds, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

BACKGROUND OF THE INVENTION

Flaviviruses, which are transmitted by mosquitoes or ticks, cause life-threatening infections in man, such as encephalitis and hemorrhagic fever. Four distinct, but closely related serotypes of the flavivirus dengue are known, so-called DENV-1, -2, -3, and -4. Dengue is endemic in most tropical and sub-tropical regions around the world, predominantly in urban and semi-urban areas. According to the World Health Organization (WHO), 2.5 billion people of which 1 billion children are at risk of DENV infection (WHO, 2002). An estimated 50 to 100 million cases of dengue fever [DF], half a million cases of severe dengue disease (i.e. dengue hemorrhagic fever [DHF] and dengue shock syndrome [DSS]), and more than 20,000 deaths occur worldwide each year. DHF has become a leading cause of hospitalization and death amongst children in endemic regions. Altogether, dengue represents the most common cause of arboviral disease. Because of recent large outbreaks in countries situated in Latin America, South-East Asia and the Western Pacific (including Brazil, Puerto Rico, Venezuela, Cambodia, Indonesia, Vietnam, Thailand), numbers of dengue cases have risen dramatically over the past years. Not only is the number of dengue cases increasing as the disease is spreading to new areas, but the outbreaks tend to be more severe.

To prevent and/or control the disease associated with dengue viral infection, the only available methods at present are mosquito eradication strategies to control the vector. Although progress is being made in the development of vaccines against dengue, many difficulties are encountered. These include the existence of a phenomenon referred to as antibody-dependent enhancement (ADE). Recovery from an infection by one serotype provides lifelong immunity against that serotype but confers only partial and transient protection against a subsequent infection by one of the other three serotypes. Following infection with another serotype, pre-existing heterologous antibodies form complexes with the newly infecting dengue virus serotype but do not neutralize the pathogen. Instead, virus entry into cells is believed to be facilitated, resulting in uncontrolled virus replication and higher peak viral titers. In both primary and secondary infections, higher viral titers are associated with more severe dengue disease. Since maternal antibodies can easily pass on to infants by breast feeding, this might be one of the reasons that children are more affected by severe dengue disease than adults.

In locations with two or more serotypes circulating simultaneously, also referred to as hyper endemic regions, the risk of serious dengue disease is significantly higher due to an increased risk of experiencing a secondary, more severe infection. Moreover, in a situation of hyper-endemicity, the probability of the emergence of more virulent strains is increased, which in turn augments the probability of dengue hemorrhagic fever (DHF) or dengue shock syndrome.

The mosquitoes that carry dengue, including *Aedes aegypti* and *Aedes albopictus* (tiger mosquito), are moving north on the globe. According to the United States (US) Centers for Disease Control and Prevention (CDC), both mosquitoes are currently omnipresent in southern Texas. The spread north of dengue-carrying mosquitoes is not confined to the US, but has also been observed in Europe.

Despite large efforts over the past 3 decades, there is currently no vaccine available to protect humans against dengue virus disease. The main problem is to develop a vaccine that offers protection against all four serotypes (a tetravalent vaccine) to the same extent. Furthermore, today, specific antiviral drugs for the treatment or prevention of dengue fever virus infection are not available. Clearly, there is still a great unmet medical need for therapeutics for the prevention or treatment of viral infections in animals, more in particular in humans and especially for viral infections caused by Flaviviruses, more in particular Dengue virus. Compounds with good anti-viral potency, no or low levels of side-effects, a broad spectrum activity against multiple Dengue virus serotypes, a low toxicity and/or good pharmacokinetic or -dynamic properties are highly needed.

The present invention now provides compounds, mono- or di-substituted indole derivatives, which show high potent activity against all four (4) serotypes of the Dengue virus. Also the compounds according to the invention possess a good pharmacokinetic profile and surprisingly these specific compounds show an improved chiral stability.

SUMMARY OF THE INVENTION

The present invention is based on the unexpected finding that at least one of the above-mentioned problems can be solved by the current compounds of the invention.

The present invention provides compounds which have been shown to possess potent antiviral activity against all four (4) serotypes currently known. The present invention furthermore demonstrates that these compounds efficiently inhibit proliferation of Dengue virus (DENV). Therefore, these compounds constitute a useful class of potent compounds that can be used in the treatment and/or prevention of viral infections in animals, mammals and humans, more specifically for the treatment and/or prevention of infections with Dengue viruses.

The present invention furthermore relates to the use of such compounds as medicines and to their use for the manufacture of medicaments for treating and/or preventing viral infections, in particular with viruses belonging to the family of the Dengue viruses in animals or mammals, more in particular in humans. The invention also relates to methods for the preparation of all such compounds and to pharmaceutical compositions comprising them in an effective amount.

The present invention also relates to a method of treatment or prevention of dengue viral infections in humans by the administration of an effective amount of one or more such compounds, or a pharmaceutically acceptable salt thereof optionally in combination with one or more other medicines, like another antiviral agent or dengue vaccine or both, to a patient in need thereof.

One aspect of the invention is the provision of compounds of formula (I)

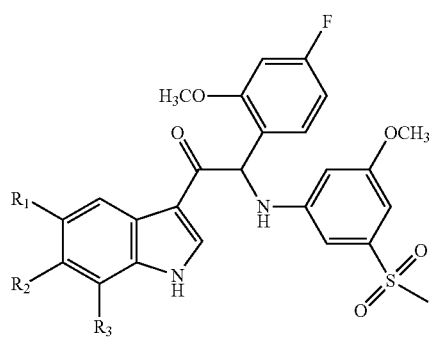

(I)

a stereo-isomeric form, a pharmaceutically acceptable salt, solvate or polymorph thereof comprising a mono- or di-substituted indole group; said compound is selected from the group wherein:
$R_1$ is F, $R_2$ is F, $CH_3$ or $OCH_3$ and $R_3$ is H,
$R_1$ is H, $R_2$ is Cl or F and $R_3$ is $CH_3$,
$R_1$ is $CH_3$, $R_2$ is $OCH_3$, F or H and $R_3$=H,
$R_1$ is H, $R_2$ is Cl or F and $R_3$ is H,
$R_1$ is $CH_3$, $R_2$ is H and $R_3$ is F,
$R_1$ is F, $R_2$ is H and $R_3$ is $CH_3$,
$R_1$ is H, $R_2$ is $OCH_3$ and $R_3$ is H or Cl,
$R_1$ is H, $R_2$ is F and $R_3$ is F,
$R_1$ is $CF_3$ or $OCF_3$, $R_2$ is H and $R_3$ is H,
$R_1$ is Cl, $R_2$ is $OCH_3$ and $R_3$ is H.

In particular the compounds of the invention or their stereo-isomeric form, a pharmaceutically acceptable salt, solvate or polymorph thereof are selected from the group:

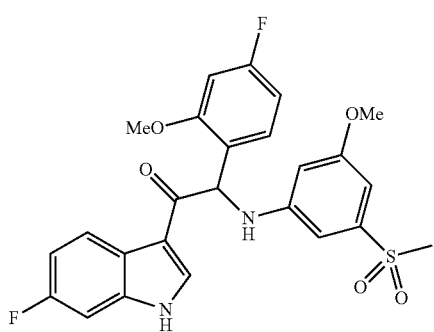

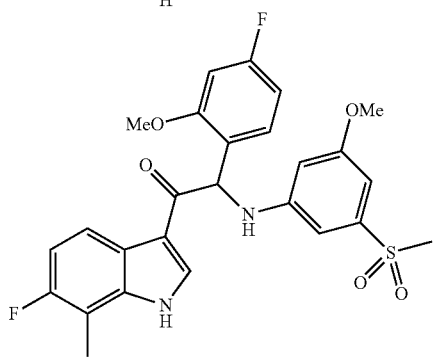

-continued

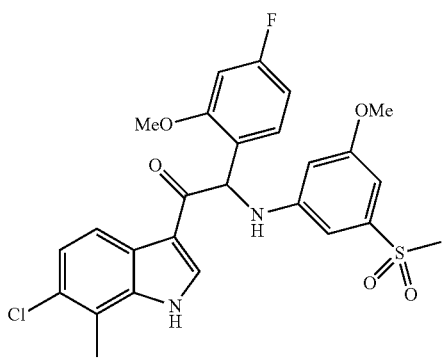

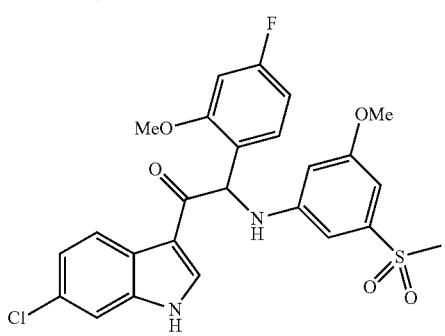

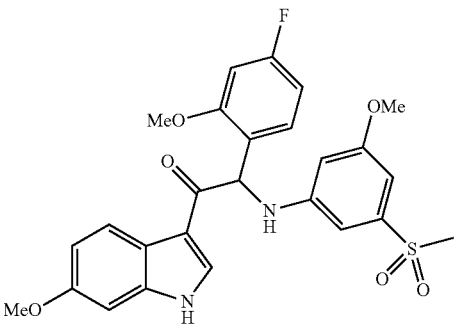

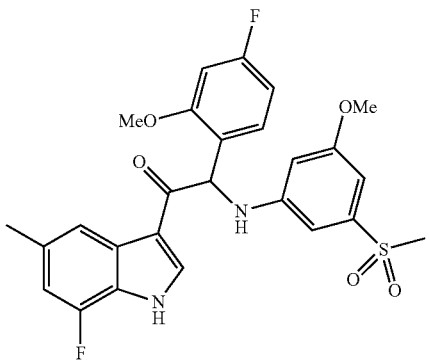

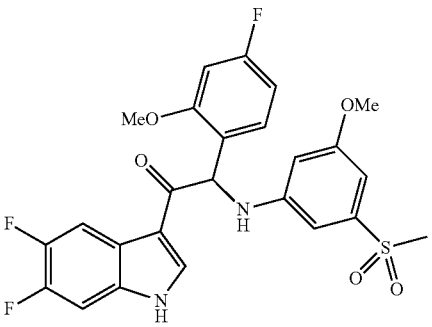

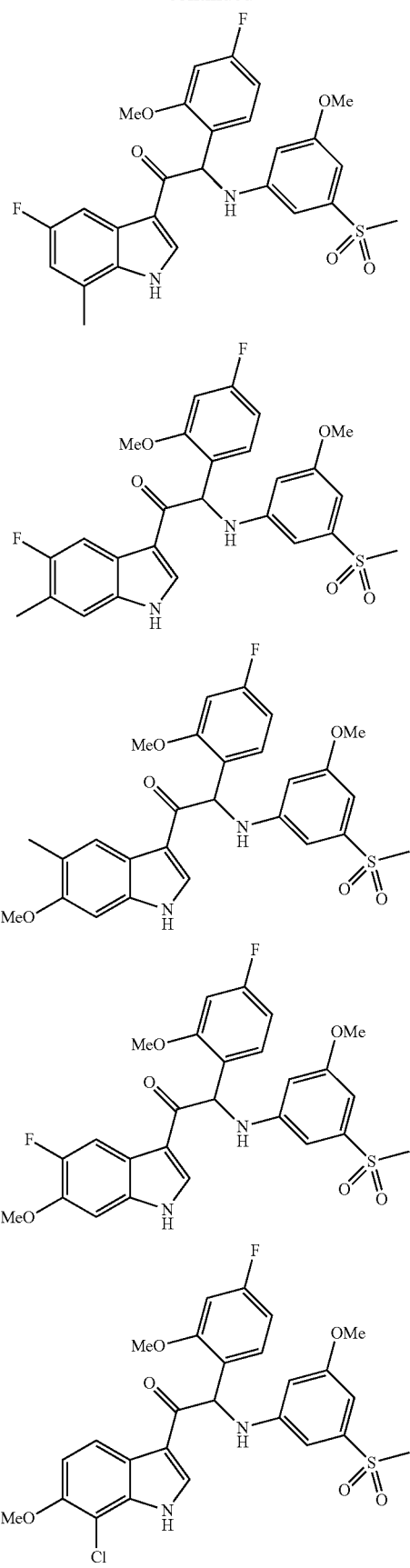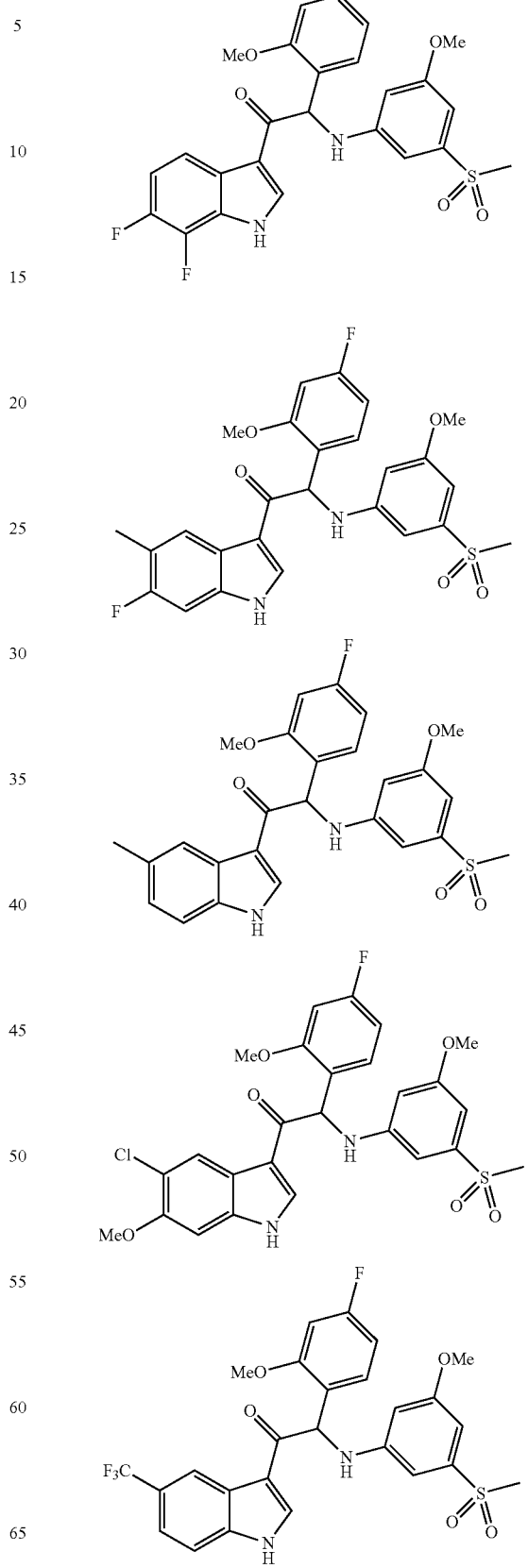

-continued

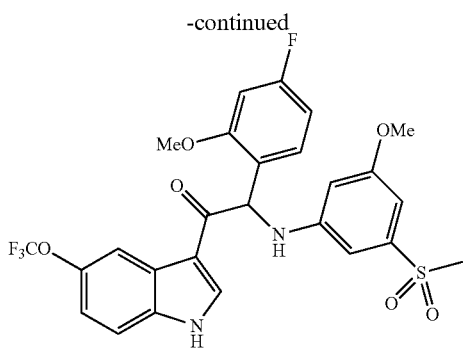

Another aspect of the invention is the use of a compound represented by the following structural formula (I)

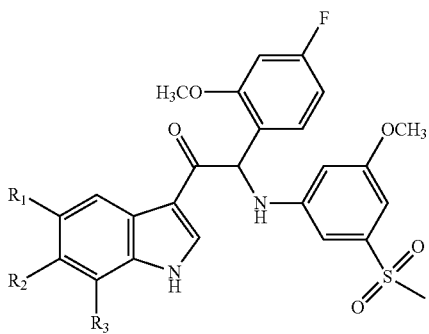

(I)

a stereo-isomeric form, a pharmaceutically acceptable salt, solvate or polymorph thereof comprising a mono- or di-substituted indole group; said compound is selected from the group wherein:
$R_1$ is F, $R_2$ is F, $CH_3$ or $OCH_3$ and $R_3$ is H,
$R_1$ is H, $R_2$ is Cl or F and $R_3$ is $CH_3$,
$R_1$ is $CH_3$, $R_2$ is $OCH_3$, F or H and $R_3$=H,
$R_1$ is H, $R_2$ is Cl or F and $R_3$ is H,
$R_1$ is $CH_3$, $R_2$ is H and $R_3$ is F,
$R_1$ is F, $R_2$ is H and $R_3$ is $CH_3$,
$R_1$ is H, $R_2$ is $OCH_3$ and $R_3$ is H or Cl,
$R_1$ is H, $R_2$ is F and $R_3$ is F,
$R_1$ is $CF_3$ or $OCF_3$, $R_2$ is H and $R_3$ is H,
$R_1$ is Cl, $R_2$ is $OCH_3$ and $R_3$ is H
for inhibiting the replication of dengue virus(es) in a biological sample or patient.

Part of the current invention is also a pharmaceutical composition comprising a compound of formula (I) or a stereo-isomeric form, a pharmaceutically acceptable salt, solvate or polymorph thereof together with one or more pharmaceutically acceptable excipients, diluents or carriers.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral or rectal administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

The present disclosure is also intended to include any isotopes of atoms present in the compounds of the invention. For example, isotopes of hydrogen include tritium and deuterium and isotopes of carbon include C-13 and C-14. The present compounds used in the current invention may also exist in their stereo-chemically isomeric form, defining all possible compounds made up of the same atoms bonded by the same sequence of bonds but having different three-dimensional structures, which are not interchangeable. Unless otherwise mentioned or indicated, the chemical designation of compounds encompasses the mixture of all possible stereo-chemically isomeric forms, which said compounds might possess.

Said mixture may contain all dia-stereomers and/or enantiomers of the basic molecular structure of said compound. All stereo-chemically isomeric forms of the compounds used in the present invention either in pure form or in admixture with each other are intended to be embraced within the scope of the present invention including any racemic mixtures or racemates.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of compounds and intermediates used in this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

GENERAL SYNTHETIC APPROACHES

The synthesis of compounds of general formula I can be performed as outlined in Scheme 1. 2-(4-Fluoro-2-methoxyphenyl)acetic acid (II) can be converted to the corresponding 2-(4-fluoro-2-methoxyphenyl)acetyl chloride (III) with a chlorination reagent like for example thionyl chloride. The Friedel-Crafts reaction of the acid chloride III with a substituted indole of general formula IV can be performed using a Lewis acid reagent like for example $Et_2AlCl$ or $TiCl_4$ in a suitable solvent like for example $CH_2Cl_2$ or 1,2-dichloroethane, and under suitable reaction conditions that typically (but not exclusively) involve cooling, to provide the 3-acylated indole of general formula V. The introduction of an aniline moiety in alpha position to the carbonyl moiety of the compounds of general formula V can be accomplished by a reaction sequence that involves for example bromination of V with a reagent like for example phenyltrimethylammonium tribromide in a suitable solvent like for example THF, to provide the compounds of general formula VI, and subsequent reaction of the compounds of general formula VI 3-methoxy-5-(methylsulfonyl)-aniline (VII) in a suitable solvent like for example $CH_3CN$, and typically using a base like for example TEA or DIPEA, to provide the compounds of general formula I as racemic mixtures. Chiral separation of the compounds of general formula I can be performed by for example chiral chromatography to provide the Enantiomers A and B of general formula I.

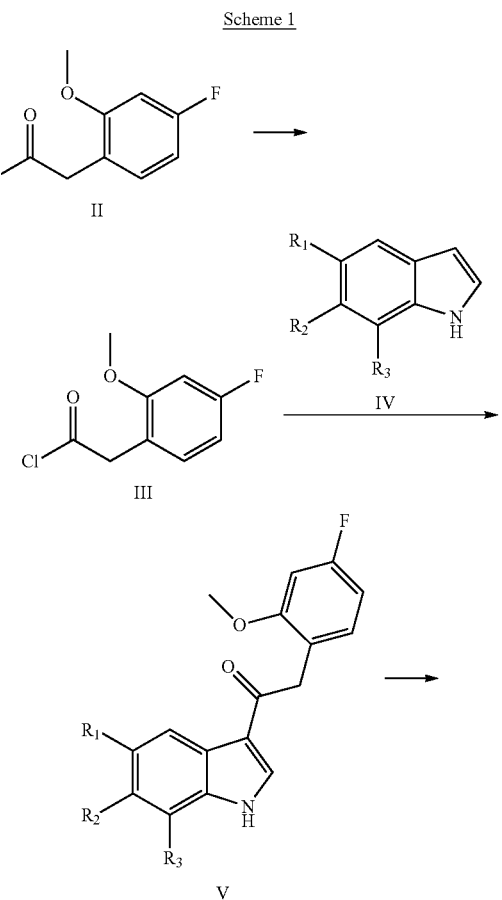

Scheme 1

-continued

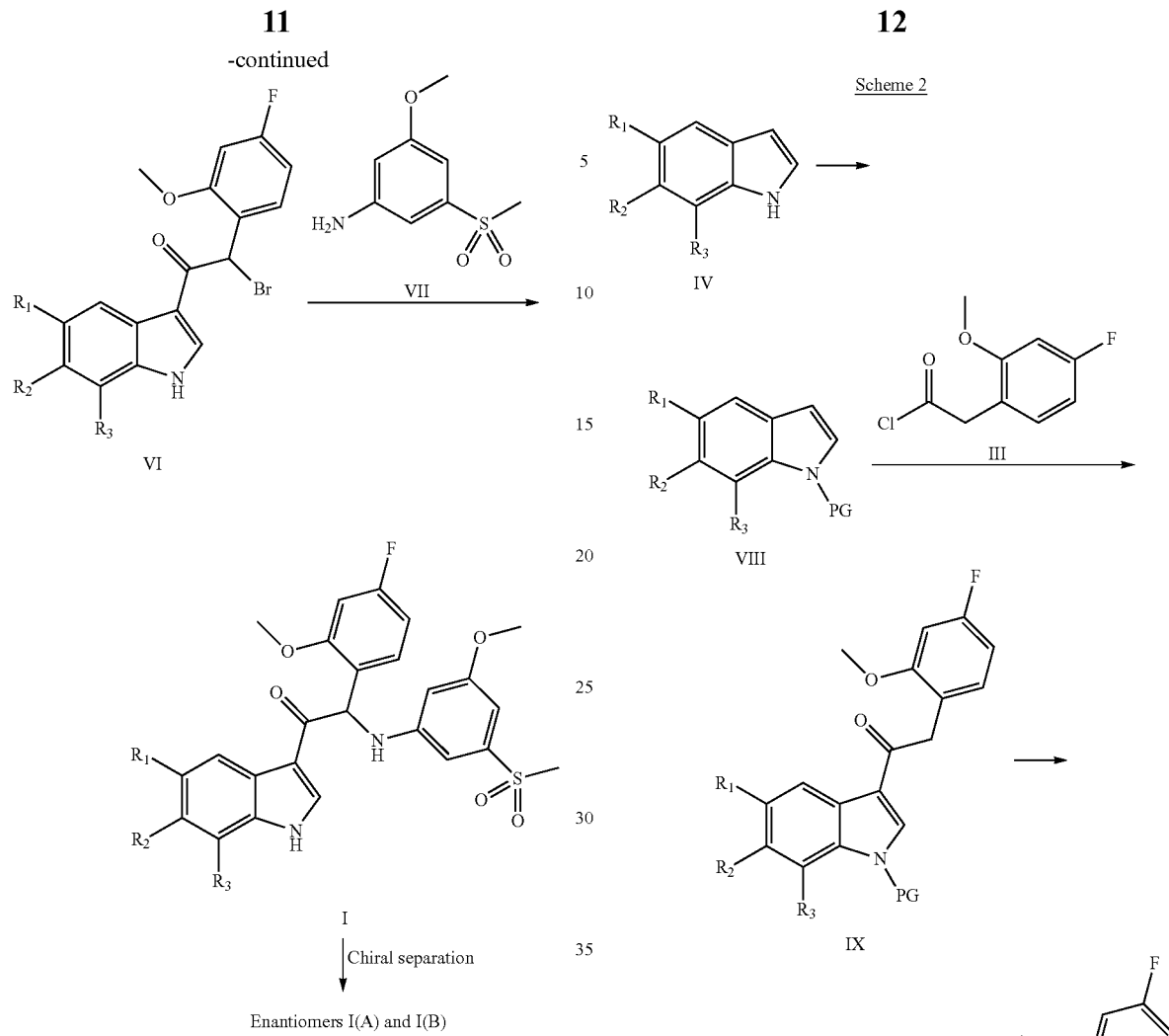

In some cases, the synthesis of the intermediate of general formula V via the Friedel-Crafts synthesis approach, benefits from the presence of a protecting group (PG) at the indole-N during the Friedel-Crafts reaction step, as outlined in Scheme 2. To this end, the substituted indole of general formula IV can be converted first to an N-protected intermediate of general formula VIII, such as for example an N-Tosylated intermediate of general formula VIII (PG=Ts), using a reagent like for example tosyl chloride, in the presence of a base like for example sodium hydride. The Friedel-Crafts reaction of the substituted indole of general formula IV with acid chloride III can be performed using a Lewis acid reagent like for example $Et_2AlCl$ or $TiCl_4$ in a suitable solvent like for example $CH_2Cl_2$ or 1,2-dichloroethane, and under suitable reaction conditions that typically (but not exclusively) involve cooling, to provide the 3-acylated N-protected indole of general formula IX. Removal of the indole-N protecting group PG of the intermediate of general formula IX can be accomplished with a reagent like for example LiOH (for PG=Ts) in a solvent mixture like for example THF/water an at a suitable reaction temperature, to provide the 3-acylated indole of general formula V.

EXAMPLES

LC/MS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

LCMS Method codes (Flow expressed in mL/min; column temperature (T) in ° C.; Run time in minutes).

SFC-MS Methods

The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Analytical SFC-MS Methods (Flow expressed in mL/min; column temperature (T) in ° C.; Run time in minutes, Backpressure (BPR) in bars.

| Method code | Instrument | Column | Mobile phase | Gradient | Flow / Col T | Run time (min) |
|---|---|---|---|---|---|---|
| LC-A | Waters: Acquity ® UPLC ®-DAD-SQD | Waters: BEH C18 (1.7 μm, 2.1 × 50 mm) | A: 10 mM $CH_3COONH_4$ in 95% $H_2O$ + 5% $CH_3CN$ B: $CH_3CN$ | From 95% A to 5% A in 1.3 min, held for 0.7 min. | 0.8 mL/min 55° C. | 2 |
| LC-B | Waters: Acquity ® UPLC ®-DAD-SQD | Waters: HSS T3 (1.8 μm, 2.1 × 100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.7 mL/min 55° C. | 3.5 |
| LC-C | Waters: Acquity ® UPLC ®-DAD-Quattro Micro ™ | Waters: BEH C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 mL/min 40° C. | 6.2 |
| LC-D | Dionex ®: Ultima ® 3000 ®-DAD-Brucker ® Esquire 6000 | X-Bridge C18 (3.5 μm, 3.0 × 100 mm) with guard (3.5 μm, 3.0 × 20 mm) | A: 10 mM $CH_3COONH_4$ in $H_2O$ adjust pH 10 with ammonia solution B: $CH_3CN$ | 50% A for 0.20 min, to 10% A in 5.8 min, held for 4.8 min, back to 50% A in 0.20 min, held for 3.00 min. | 1.0 mL/min 30° C. | 14 |
| LC-E | Dionex ®: Ultima ® 3000 ®-DAD-Brucker ® Esquire 6000 | X-Bridge C18 (3.5 μm, 3.0 × 100 mm) with guard (3.5 μm, 3.0 × 20 mm) | A: 10 mM $CH_3COONH_4$ in $H_2O$ adjust to pH 10 with ammonia solution B: $CH_3CN$ | 80% A for 0.20 min, to 40% A in 6.8 min, to 10% A in 1 min held for 2.8 min, back to 80% A in 0.20 min, held for 3.00 min. | 1.0 mL/min 30° C. | 14 |
| LC-F | Waters: Acquity ® UPLC ®-DAD-Acquity ® TQ detector | Waters: HSS C18 (1.8 μm, 2.1 × 50 mm) | A: 0.1% formic acid B: $CH_3CN$ | From 50% A to 10% A in 3.5 min, held for 1.5 min | 0.5 mL/min 40° C. | 5 |

| Method code | column | mobile phase | gradient | Flow/ColT | Run time/BPR |
|---|---|---|---|---|---|
| SFC-A | Daicel Chiralpak ® IC column (5 μm, 150 × 4.6 mm) | A: $CO_2$ B: MeOH | 30% B hold 7 min | 3/35 | 7/100 |
| SFC-B | Daicel Chiralpak ® IC column (5 μm, 150 × 4.6 mm) | A: $CO_2$ B: iPROH + 0.3% $iPRNH_2$ | 40% B hold 7 min | 3/35 | 7/100 |
| SFC-C | Daicel Chiralcel ® OD-H column (5 μm, 150 × 4.6 mm) | A: $CO_2$ B: MeOH | 40% B hold 7 min | 3/35 | 7/100 |
| SFC-D | Daicel Chiralpak ® AD-H column (5 μm, 150 × 4.6 mm) | A: $CO_2$ B: EtOH | 40% B hold 7 min | 3/35 | 7/100 |
| SFC-E | Daicel Chiralpak ® IC column (5 μm, 150 × 4.6 mm) | A: $CO_2$ B: MeOH | 40% B hold 7 min | 3/35 | 7/100 |
| SFC-F | Daicel Chiralpak ® AD column (5 μm, 150 × 4.6 mm) | A: $CO_2$ B: iPROH + 0.3% $iPRNH_2$ | 40% B hold 7 min | 3/35 | 7/100 |
| SFC-G | Daicel Chiralpak ® IA column (5 μm, 250 × 4.6 mm) | A: $CO_2$ B: MeOH | 30% B hold 7 min | 3/35 | 7/100 |
| SFC-H | Daicel Chiralpak ® AD-H column (5 μm, 150 × 4.6 mm) | A: $CO_2$ B: iPROH + 0.3% $iPRNH_2$ | 25% B hold 7 min | 3/35 | 7/100 |
| SFC-I | Daicel Chiralpak ® AS3 column (3 μm, 150 × 4.6 mm) | A: $CO_2$ B: EtOH + 0.2% $iPRNH_2$ + 3% $H_2O$ | 25% B hold 6 min, to 50% in 1 min hold 2.5 min | 2.5/40 | 9.5/110 |
| SFC-J | Daicel Chiralpak ® AS3 column (3 μm, 150 × 4.6 mm) | A: $CO_2$ B: EtOH + 0.2% $iPRNH_2$ + 3% $H_2O$ | 10%-50% B in 6 min, hold 3.5 min | 2.5/40 | 9.5/110 |
| SFC-K | Daicel Chiralpak ® AD3 column (3 μm, 150 × 4.6 mm) | A: $CO_2$ B: EtOH + 0.2% $iPRNH_2$ + 3% $H_2O$ | 40% B hold 6 min, to 50% in 1 min, hold 2.5 min | 2.5/40 | 9.5/110 |
| SFC-L | Daicel Chiralpak ® AD3 column (3 μm, 150 × 4.6 mm) | A: $CO_2$ B: MeOH + 0.2% $iPRNH_2$ + 3% $H_2O$ | 35% B hold 6 min, to 50% in 1 min, hold 2.5 min | 2.5/40 | 9.5/110 |
| SFC-M | Daicel Chiralpak ® OD3 column (3 μm, 150 × 4.6 mm) | A: $CO_2$ B: EtOH + 0.2% $iPRNH_2$ + 3% $H_2O$ | 35% B hold 6 min, to 50% in 1 min, hold 2.5 min | 2.5/40 | 9.5/110 |
| SFC-N | Daicel Chiralpak ® AD3 column (3 μm, 150 × 4.6 mm) | A: $CO_2$ B: EtOH + 0.2% $iPRNH_2$ + 3% $H_2O$ | 45% B hold 6 min, to 50% in 1 min, hold 2.5 min | 2.5/40 | 9.5/110 |
| SFC-O | Daicel Chiralpak ® AD3 column (3 μm, 150 × 4.6 mm) | A: $CO_2$ B: EtOH + 0.2% $iPRNH_2$ + 3% $H_2O$ | 35% B hold 6 min, to 50% in 1 min, hold 2.5 min | 2.5/40 | 9.5/110 |

Melting Points

Values are either peak values or melt ranges, and are obtained with experimental uncertainties that are commonly associated with this analytical method.

DSC823e (Indicated as DSC)

For a number of compounds, melting points were determined with a DSC823e (Mettler-Toledo). Melting points were measured with a temperature gradient of 10° C./minute. Maximum temperature was 300° C.

Optical Rotations:

Optical rotations were measured on a Perkin-Elmer 341 polarimeter with a sodium lamp and reported as follows: $[\alpha]°$ ($\lambda$, c g/100 ml, solvent, T° C.).

$[\alpha]_\lambda^T = (100\alpha)/(l \times c)$: where l is the path length in dm and c is the concentration in g/100 ml for a sample at a

Example 1 synthesis of 1-(6-fluoro-1H-indol-3-yl)-2-(4-fluoro-2-methoxyphenyl)-2-((3-methoxy-5-(methylsulfonyl)phenyl)amino)ethanone (Compound 1) and chiral separation into Enantiomers 1A and 1B

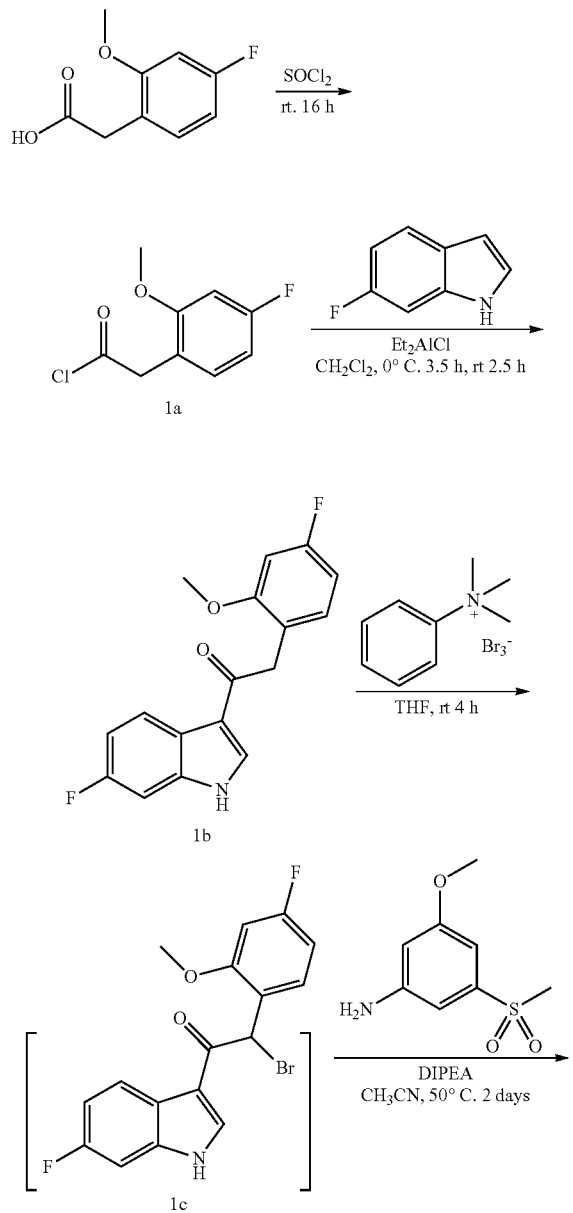

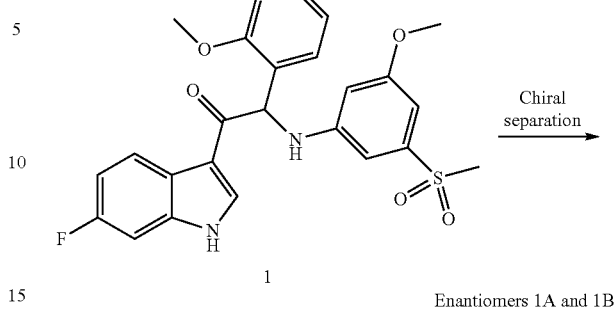

Enantiomers 1A and 1B

Synthesis of Intermediate 1a 2-(4-Fluoro-2-methoxyphenyl)acetic acid [CAS 886498-61-9] (28.9 g, 157 mmol) was added in small portions to thionyl chloride (150 mL) and the resulting solution was stirred overnight at room temperature. The solvent was concentrated under reduced pressure and co-evaporated with toluene to give 2-(4-fluoro-2-methoxy-phenyl)acetyl chloride 1a (31.8 g) as an oily residue that was used without further purification in the next step.

Synthesis of Intermediate 1b

A solution of 6-fluoro-1H-indole [CAS 399-51-9] (14.2 g, 105 mmol) in $CH_2Cl_2$ (400 mL) was cooled to 0° C. under $N_2$-atmosphere. A solution of diethylaluminum chloride 1M in hexane (160 mL, 160 mmol) was added over a period of 10 min to the stirred solution and the resulting mixture was kept at 0° C. for 40 min. Then, a solution of 2-(4-fluoro-2-methoxyphenyl)acetyl chloride 1a (31.8 g, 157 mmol) in $CH_2Cl_2$ (300 mL) was added dropwise over a period of 2.5 h while keeping the internal temperature of the reaction mixture below 5° C. The temperature of the stirred reaction mixture was maintained at 0° C. for 3.5 h. The ice-bath was removed and after stirring at room temperature for 2.5 h, the reaction mixture was cooled again to 0° C. and the reaction was quenched by the slow addition of a solution of potassium sodium tartrate tetrahydrate [CAS 6100-16-9] (59.6 g, 210 mmol) in water (70 mL) while keeping the internal temperature of the mixture below 10° C. After stirring for an additional 30 min at 0° C., the ice-bath was removed and the resulting mixture was diluted with THF (1 L). $Na_2SO_4$ (150 g) was added and after overnight stirring, the mixture was filtered over Dicalite®. The filter cake was washed twice with THF (2×1 L). The combined filtrates were evaporated under reduced pressure to a residual volume of approximately 50 mL. A white precipitate was filtered off and dried under vacuum at 50° C. to provide 1-(6-fluoro-1H-indol-3-yl)-2-(4-fluoro-2-methoxyphenyl)ethanone 1b (22.3 g) as a white powder.

Synthesis of Compound 1 and chiral separation of Enantiomers 1A and 1B

A stirred solution of 1-(6-fluoro-1H-indol-3-yl)-2-(4-fluoro-2-methoxyphenyl)-ethanone 1b (11.0 g, 36.3 mmol) in THF (300 mL) was cooled to 0° C. under $N_2$-atmosphere. A solution of phenyltrimethylammonium tribromide [CAS 4207-56-1] (14.3 g, 38.2 mmol) in THF (100 mL) was added dropwise over a period of 45 min. The resulting suspension was stirred at room temperature for 4 h and evaporated under reduced pressure to a white residue. This residue, containing the crude 2-bromo-1-(6-fluoro-1H-indol-3-yl)-2-(4-fluoro-2-methoxyphenyl)-ethanone 1c, was dissolved in acetonitrile (300 mL). After addition of 3-methoxy-5-(methylsulfonyl)aniline [CAS 62606-02-4] (14.8 g, 73 mmol) and diisopropylethyl-amine (13 mL, 75 mmol), the mixture was stirred at 50° C. for two days—until complete conversion to Compound 1. The reaction mixture was concentrated under reduced pressure, the residue was mixed with water (500 mL) and the product was extracted with 2-methyl-THF (2×500 mL). The combined organic layers were washed with 0.5N HCl (800 mL), a saturated aqueous solution of NaHCO$_3$ (200 mL) and brine (200 mL), dried over MgSO$_4$, filtered and evaporated under reduced pressure. The residue was crystallized from EtOAc (50 mL). The solids were filtered off and dried under vacuum at 50° C. to give 1-(6-fluoro-1H-indol-3-yl)-2-(4-fluoro-2-methoxyphenyl)-2-((3-methoxy-5-(methylsulfonyl)phenyl)-amino)ethanone (Compound 1, 9.9 g) as a racemic mixture.

Chiral separation of the enantiomers of Compound 1 (9.67 g) was performed via Normal Phase Chiral Chromatography (Stationary phase: AS 20 μm (1 kg), Mobile phase: 100% MeOH). The product fractions containing the first eluted enantiomer were combined and evaporated under reduced pressure (water bath 38° C.) to a residual volume of 30 mL. The resulting suspension was filtered and the solids were washed with small fractions of MeOH and dried under vacuum at 40° C. to provide Enantiomer 1A (2.9 g) as a white solid. The combined product fractions of the second eluted product were evaporated under reduced pressure (water bath 37° C.) until a residual volume of 90 mL. The solids were filtered off, washed with small fractions of MeOH and dried under vacuum at 40° C. to provide Enantiomer 1B (3.15 g).

Compound 1:
$^1$H NMR (360 MHz, DMSO-d$_6$) δ ppm 3.09 (s, 3 H) 3.73 (s, 3 H) 3.99 (s, 3 H) 6.23 (d, J=7.75 Hz, 1 H) 6.56-6.62 (m, 2 H) 6.74 (td, J=8.48, 2.48 Hz, 1 H) 6.91 (t, J=1.46 Hz, 1 H) 6.96 (dd, J=11.35, 2.50 Hz, 1 H) 7.02-7.11 (m, 2 H) 7.28 (dd, J=9.62, 2.38 Hz, 1 H) 7.37 (dd, J=8.61, 6.83 Hz, 1 H) 8.15 (dd, J=8.76, 5.59 Hz, 1 H) 8.44 (s, 1 H) 12.09 (br. s., 1 H)

LC/MS (method LC-A): R$_t$ 1.08 min, MH$^+$ 501

Enantiomer 1A:
$^1$H NMR (600 MHz, DMSO-d$_6$) δ ppm 3.09 (s, 3 H) 3.72 (s, 3 H) 3.99 (s, 3 H) 6.23 (d, J=7.78 Hz, 1 H) 6.58-6.59 (m, 1 H) 6.59-6.60 (m, 1 H) 6.73 (td, J=8.44, 2.49 Hz, 1 H) 6.92 (t, J=1.61 Hz, 1 H) 6.96 (dd, J=11.30, 2.49 Hz, 1 H) 7.04 (d, J=7.80 Hz, 1 H) 7.06 (ddd, J=9.68, 8.80, 2.35 Hz, 1 H) 7.27 (dd, J=9.61, 2.27 Hz, 1 H) 7.37 (dd, J=8.66, 6.90 Hz, 1 H) 8.15 (dd, J=8.80, 5.58 Hz, 1 H) 8.43 (s, 1 H) 12.09 (br. s., 1 H)

LC/MS (method LC-A): R$_t$ 1.08 min, MH$^+$ 501

[α]$_D^{20}$: +131.7° (c 0.48, DMF)

Chiral SFC (method SFC-K): R$_t$ 2.22 min, MH$^+$ 501, chiral purity 100%.

Melting point: 241° C.

Enantiomer 1B:
$^1$H NMR (360 MHz, DMSO-d$_6$) δ ppm 3.09 (s, 3 H) 3.72 (s, 3 H) 3.99 (s, 3 H) 6.23 (d, J=7.77 Hz, 1 H) 6.56-6.61 (m, 2 H) 6.73 (td, J=8.48, 2.46 Hz, 1 H) 6.91 (t, J=1.83 Hz, 1 H) 6.96 (dd, J=11.36, 2.49 Hz, 1 H) 7.01-7.12 (m, 2 H) 7.27 (dd, J=9.62, 2.38 Hz, 1 H) 7.36 (dd, J=8.62, 6.85 Hz, 1 H) 8.15 (dd, J=8.77, 5.59 Hz, 1 H) 8.44 (s, 1 H) 12.07 (br. s, 1 H)

LC/MS (method LC-A): R$_t$ 1.07 min, MH$^+$ 501

[α]$_D^{20}$: −127.7° (c 0.535, DMF)

Chiral SFC (method SFC-K): R$_t$ 3.68 min, MH$^+$ 501, chiral purity 100%.

Melting point: 249° C.

Example 2 synthesis 2-(4-fluoro-2-methoxyphenyl)-1-(6-fluoro-7-methyl-1H-indol-3-yl)-2-((3-methoxy-5-(methylsulfonyl)phenyl)amino)ethanone (Compound 2) and chiral separation into Enantiomers 2A and 2B

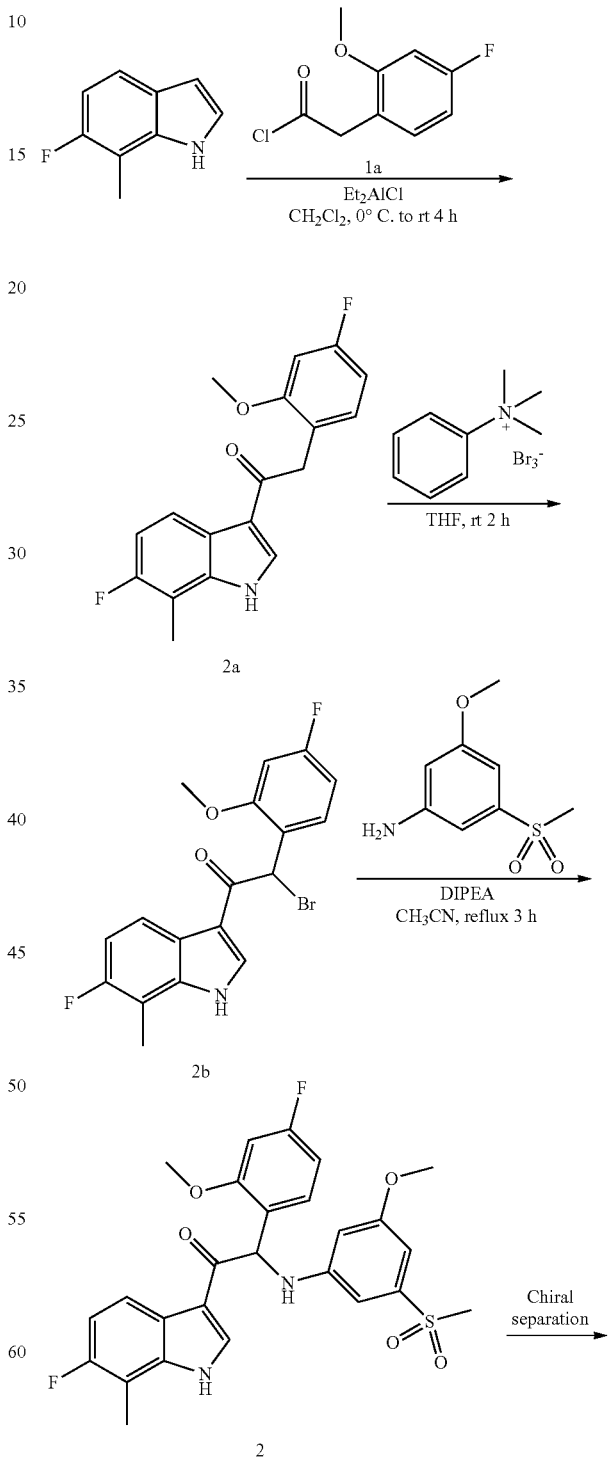

Enantiomers 2A and 2B

Synthesis of Intermediate 2a

A stirred solution of 6-fluoro-7-methyl-1H-indole [CAS 57817-10-4] (5.41 g, 36.2 mmol) in CH$_2$Cl$_2$ (100 mL) was cooled on ice under N$_2$-atmosphere. A solution of diethylaluminum chloride 1M in hexane (54.4 mL, 54.4 mmol) was added dropwise. After 15 min at 0° C., a solution of 2-(4-fluoro-2-methoxyphenyl)-acetyl chloride 1a (11.0 g, 54.4 mmol, for synthesis: see Example 1) in CH$_2$Cl$_2$ (30 mL) was added dropwise while keeping the internal temperature below 5° C. The ice-bath was removed and the resulting suspension was stirred at room temperature for 4 h. The reaction mixture was poured out slowly into a cooled (0° C.) saturated aqueous solution of NaHCO$_3$. The mixture was filtered over Dicalite® and the filter cake was washed with THF. The combined filtrates were extracted with EtOAc, dried over MgSO$_4$ and evaporated under reduced pressure. The residue was triturated with CH$_2$Cl$_2$ and the solids were filtered off to give 2-(4-fluoro-2-methoxyphenyl)-1-(6-fluoro-7-methyl-1H-indol-3-yl)ethanone 2a (7.47 g) as a white powder.

Synthesis of Intermediate 2b

A stirred solution of 2-(4-fluoro-2-methoxyphenyl)-1-(6-fluoro-7-methyl-1H-indol-3-yl)ethanone 2a (7.43 g, 23.56 mmol) in THF (100 mL) was cooled at 0° C. under N$_2$-atmosphere. A solution of phenyltrimethylammonium tribromide [CAS 4207-56-1] (8.96 g, 23.8 mmol) in THF (100 mL) was added dropwise. After the addition, the reaction mixture was stirred for 2 h at room temperature. The suspension was filtered to remove the solids and the filtrate was evaporated under reduced pressure. The residue was triturated with CH$_2$Cl$_2$, the solids were filtered off and dried under vacuum to provide 2-bromo-2-(4-fluoro-2-methoxyphenyl)-1-(6-fluoro-7-methyl-1H-indol-3-yl)ethanone 2b (8.95 g).

Synthesis of Compound 2 and chiral separation of Enantiomers 2A and 2B

2-Bromo-2-(4-fluoro-2-methoxyphenyl)-1-(6-fluoro-7-methyl-1H-indol-3-yl)-ethanone 2b (3.07 g, 7.8 mmol), 3-methoxy-5-(methylsulfonyl)aniline [CAS 62606-02-4] (1.63 g, 8.11 mmol), and diisopropylethylamine (1.35 mL, 7.83 mmol) were mixed in CH$_3$CN (100 mL) and the mixture was heated under reflux for 3 h. After cooling to room temperature, the solvent was evaporated under reduced pressure and the residue was purified by column chromatography on silica (Stationary phase: HP-Spher 25 µM (340 g), Mobile phase: heptane/EtOAc gradient 100/0 to 0/100). The product fractions were evaporated under reduced pressure. A small aliquot of the oily residue was solidified by trituration with CH$_2$Cl$_2$. The solids were isolated by filtration, washed with CH$_2$Cl$_2$ and dried under vacuum to provide 2-(4-fluoro-2-methoxyphenyl)-1-(6-fluoro-7-methyl-1H-indol-3-yl)-2-((3-methoxy-5-(methylsulfonyl)phenyl)amino)ethanone (Compound 2, 250 mg) as a racemic mixture.

Chiral separation of the enantiomers of Compound 2 (787 mg) was performed via Preparative SFC (Stationary phase: Chiralpak® Diacel OJ 30×250 mm, Mobile phase: CO$_2$, MeOH with 0.2% iPrNH$_2$) and the product fractions were combined and evaporated under reduced pressure. The first eluted enantiomer was further purified by column chromatography (Stationary phase: HP-Spher 25 µM (10 g), Mobile phase: heptane/EtOAc gradient 100/0 to 0/100). Evaporation of the product fractions and lyophilization of the oily residue from a mixture of CH$_3$CN and water provided Enantiomer 2A (91 mg) as an amorphous powder. The second eluted enantiomer was further purified by column chromatography (Stationary phase: HP-Spher 25 µM (10 g), Mobile phase: heptane/EtOAc gradient 100/0 to 0/100). Evaporation of the product fractions and lyophilization of the oily residue from a mixture of CH$_3$CN and water provided enantiomer 2B (141 mg) as an amorphous powder.

Compound 2:

$^1$H NMR (360 MHz, DMSO-d$_6$) δ ppm 2.38 (s, 3 H) 3.09 (s, 3 H) 3.72 (s, 3 H) 4.00 (s, 3 H) 6.25 (d, J=7.69 Hz, 1 H) 6.59 (d, J=10.28 Hz, 2 H) 6.73 (t, J=8.32 Hz, 1 H) 6.88-7.10 (m, 4 H) 7.36 (t, J=7.68 Hz, 1 H) 7.97 (dd, J=8.00, 6.07 Hz, 1 H) 8.45 (s, 1 H) 12.23 (br. s, 1 H)

LC/MS (method LC-A): R$_t$ 1.11 min, MH$^+$ 515

Enantiomer 2A:

$^1$H NMR (360 MHz, DMSO-d$_6$) δ ppm 2.38 (d, J=1.57 Hz, 3 H) 3.09 (s, 3 H) 3.72 (s, 3 H) 4.00 (s, 3 H) 6.25 (d, J=7.74 Hz, 1 H) 6.56-6.62 (m, 2 H) 6.73 (td, J=8.49, 2.49 Hz, 1 H) 6.90-7.07 (m, 4 H) 7.36 (dd, J=8.62, 6.83 Hz, 1 H) 7.97 (dd, J=8.71, 5.21 Hz, 1 H) 8.45 (s, 1 H) 12.22 (br. s., 1 H)

LC/MS (method LC-B): R$_t$ 2.06 min, MH$^+$ 515

$[\alpha]_D^{20}$: +110.6° (c 0.5, DMF)

Chiral SFC (method SFC-L): R$_t$ 2.86 min, MH$^+$ 515, chiral purity 100%.

Enantiomer 2B:

$^1$H NMR (360 MHz, DMSO-d$_6$) δ ppm 2.38 (d, J=1.59 Hz, 3 H) 3.09 (s, 3 H) 3.72 (s, 3 H) 4.00 (s, 3 H) 6.25 (d, J=7.73 Hz, 1 H) 6.56-6.59 (m, 1 H) 6.59-6.62 (m, 1 H) 6.73 (td, J=8.47, 2.46 Hz, 1 H) 6.87-7.10 (m, 4 H) 7.36 (dd, J=8.60, 6.83 Hz, 1 H) 7.97 (dd, J=8.68, 5.23 Hz, 1 H) 8.45 (s, 1 H) 12.22 (br. s, 1 H)

LC/MS (method LC-B): R$_t$ 2.07 min, MH$^+$ 515

$[\alpha]_D^{20}$: −104.1° (c 0.538, DMF)

Chiral SFC (method SFC-L): R$_t$ 3.38 min, MH$^+$ 515, chiral purity 100%.

Example 3

Synthesis of 1-(6-chloro-7-methyl-1H-indol-3-yl)-2-(4-fluoro-2-methoxyphenyl)-2-((3-methoxy-5-(methylsulfonyl)phenyl)amino)ethanone (Compound 3) and chiral separation into Enantiomers 3A and 3B

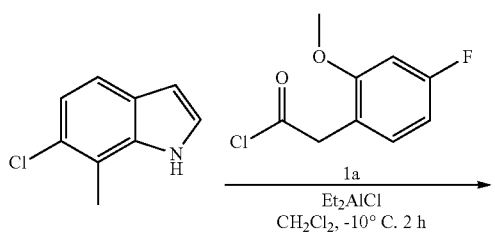

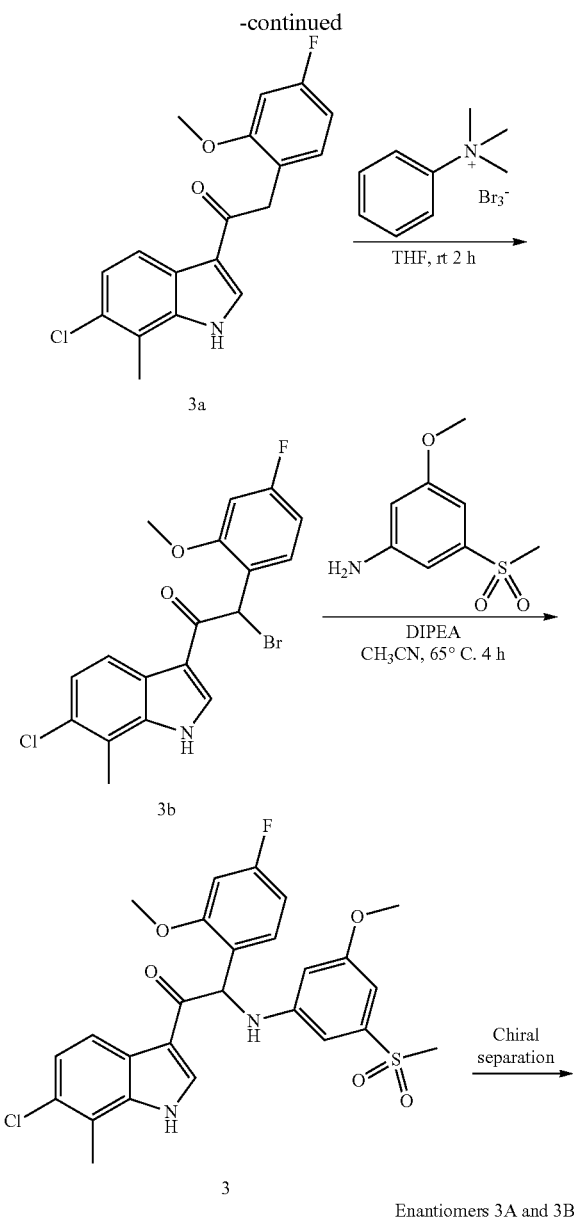

Synthesis of Intermediate 3a

A stirred solution of 6-chloro-7-methyl-1H-indole [CAS 57817-09-1] (3.2 g, 19.3 mmol) in CH₂Cl₂ (150 mL) under N₂-flow, was cooled on an ice-NaCl cooling bath. Diethylaluminum chloride 1M in hexane (29 mL, 29 mmol) was added over a period of 2 min and the cooled solution was stirred at −10° C. for 30 min. A solution of 2-(4-fluoro-2-methoxyphenyl)acetyl chloride 1a (5.48 g, 27.1 mmol, synthesis: see Example 1) in CH₂Cl₂ (30 mL) was added dropwise over 30 min while keeping the internal temperature below −10° C. and the resulting mixture was stirred for an additional 2 h at −10° C. The reaction was quenched by the slow addition of a solution of potassium sodium tartrate tetrahydrate [CAS 6100-16-9] (10.9 g, 38.6 mmol) in water (10 mL) and the mixture was stirred at room temperature for 15 min. A white precipitate was present in the reaction mixture. The precipitate was isolated by filtration, washed with water and dried under vacuum to provide 1-(6-chloro-7-methyl-1H-indol-3-yl)-2-(4-fluoro-2-methoxyphenyl) ethanone 3a (4200 mg) as an off-white solid.

Synthesis of Intermediate 3b

A solution of 1-(6-chloro-7-methyl-1H-indol-3-yl)-2-(4-fluoro-2-methoxyphenyl)-ethanone 3a (2000 mg, 6.03 mmol) in THF (120 mL) was stirred at room temperature under N₂-atmosphere. A solution of phenyltrimethylammonium tribromide [CAS 4207-56-1] (2.38 g, 6.33 mmol) in THF (35 mL) was added dropwise and the mixture was stirred for an additional 90 min at room temperature. The precipitate was filtered off and the filtrate was concentrated under vacuum to provide 2-bromo-1-(6-chloro-7-methyl-1H-indol-3-yl)-2-(4-fluoro-2-methoxyphenyl)ethanone 3b (2200 mg) as an off-white powder.

Synthesis of Compound 3 and chiral separation of Enantiomers 3A and 3B

2-Bromo-1-(6-chloro-7-methyl-1H-indol-3-yl)-2-(4-fluoro-2-methoxyphenyl)-ethanone 3b (1.29 g, 3.15 mmol) was suspended in CH₃CN (60 mL). 3-Methoxy-5-(methylsulfonyl)aniline [CAS 62606-02-4] (0.7 g, 3.46 mmol), and diisopropylethylamine (1.2 mL, 6.9 mmol) were added and the stirred mixture was heated at 65° C. for 4 h. The mixture was concentrated under vacuum and the residue was partitioned between EtOAc and water. The organic layer was separated, dried over Na₂SO₄, filtered and evaporated under reduced pressure. The residue was purified by column chromatography (Stationary phase: Grace Reveleris® silica (330 g), Mobile phase: EtOAc/heptane gradient 50/50 to 100/0) and subsequently by Preparative HPLC (Stationary phase: Uptisphere C18 ODB—10 μm, 200 g, 5 cm, Mobile phase: 0.25% NH₄HCO₃ solution in water, CH₃CN) to give 1-(6-chloro-7-methyl-1H-indol-3-yl)-2-(4-fluoro-2-methoxyphenyl)-2-((3-methoxy-5-(methylsulfonyl)phenyl)amino)ethanone (Compound 3, 725 mg) as a racemic mixture.

Chiral separation of the enantiomers of Compound 3 (635 mg) was performed using Normal Phase Chiral separation (Stationary phase: AS 5 μm, Mobile phase: 100% MeOH, isocratic elution. Detection wavelength 308 nm, flow 1 mL/min). The product fractions were combined and evaporated to provide Enantiomer 3A (223 mg) as the first eluted product and Enantiomer 3B (247 mg) as the second eluted product. Both enantiomers 3A and 3B occurred as amorphous powders.

Compound 3:

¹H NMR (400 MHz, CHLOROFORM-d) δ ppm 2.49 (s, 3 H) 2.94 (s, 3 H) 3.77 (s, 3 H) 4.12 (s, 3 H) 6.03 (d, J=6.31 Hz, 1 H) 6.18 (d, J=6.27 Hz, 1 H) 6.42 (t, J=2.20 Hz, 1 H) 6.57 (td, J=8.36, 2.42 Hz, 1 H) 6.64 (dd, J=10.56, 2.42 Hz, 1 H) 6.70 (dd, J=2.21, 1.51 Hz, 1 H) 6.84 (t, J=1.76 Hz, 1 H) 7.24-7.30 (m, 1 H) 7.28 (d, J=8.58 Hz, 1 H) 8.15 (d, J=8.61 Hz, 1 H) 8.17 (d, J=3.07 Hz, 1 H) 8.70 (br. s., 1 H)

LC/MS (method LC-B): $R_t$ 2.16 min, MH⁺ 531

Enantiomer 3A:

¹H NMR (400 MHz, DMSO-d₆) δ ppm 2.50 (s, 3 H) 3.09 (s, 3 H) 3.72 (s, 3 H) 4.00 (s, 3 H) 6.26 (d, J=7.68 Hz, 1 H) 6.57-6.59 (m, 1 H) 6.60-6.63 (m, 1 H) 6.73 (td, J=8.48, 2.50 Hz, 1 H) 6.90-6.93 (m, 1 H) 6.96 (dd, J=11.37, 2.55 Hz, 1 H) 7.02 (d, J=7.71 Hz, 1 H) 7.22 (d, J=8.53 Hz, 1 H) 7.36 (dd, J=8.62, 6.82 Hz, 1 H) 7.99 (d, J=8.50 Hz, 1 H) 8.45 (s, 1 H) 12.25 (br. s, 1 H)

LC/MS (method LC-A): $R_t$ 1.18 min, MH⁺ 531

$[\alpha]_D^{20}$: +111.1° (c 0.515, DMF)

Chiral SFC (method SFC-M): $R_t$ 2.07 min, MH⁺ 531, chiral purity 100%.

Enantiomer 3B:

$^1$H NMR (400 MHz, DMSO-$d_6$) δ ppm 2.50 (s, 3 H) 3.09 (s, 3 H) 3.72 (s, 3 H) 4.00 (s, 3 H) 6.26 (d, J=7.70 Hz, 1 H) 6.56-6.59 (m, 1 H) 6.60-6.62 (m, 1 H) 6.73 (td, J=8.48, 2.51 Hz, 1 H) 6.91-6.93 (m, 1 H) 6.96 (dd, J=11.33, 2.53 Hz, 1 H) 7.02 (d, J=7.72 Hz, 1 H) 7.22 (d, J=8.54 Hz, 1 H) 7.36 (dd, J=8.62, 6.82 Hz, 1 H) 7.99 (d, J=8.50 Hz, 1 H) 8.45 (s, 1 H) 12.25 (br. s, 1 H)

LC/MS (method LC-A): $R_t$ 1.18 min, MH$^+$ 531

$[α]_D^{20}$: −100.7° (c 0.55, DMF)

Chiral SFC (method SFC-M): $R_t$ 2.45 min, MH$^+$ 531, chiral purity 100%.

Example 4 synthesis 1-(6-chloro-1H-indol-3-yl)-2-(4-fluoro-2-methoxyphenyl)-2-((3-methoxy-5-(methylsulfonyl)phenyl)amino)ethanone (Compound 4) and chiral separation into Enantiomers 4A and 4B

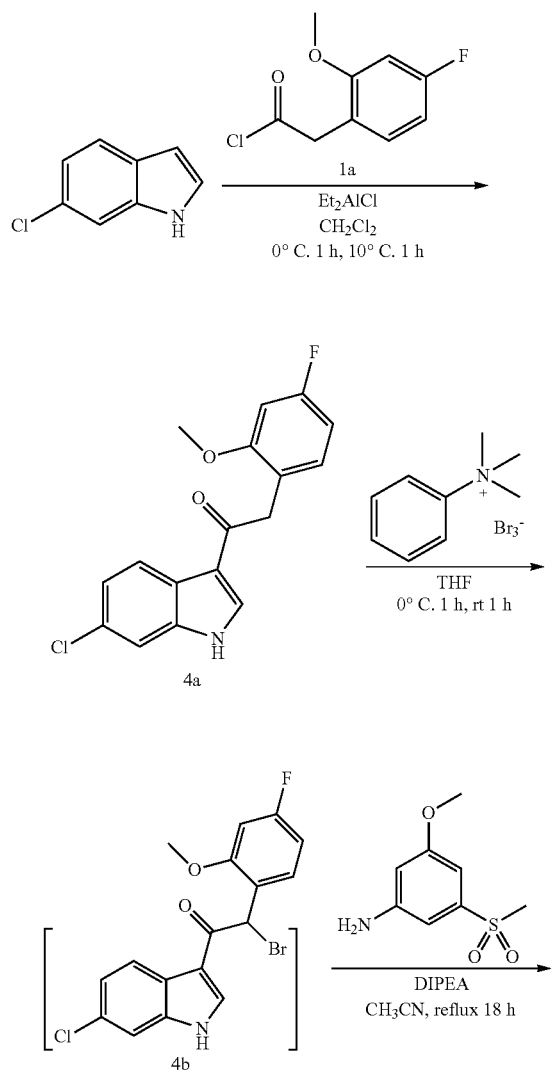

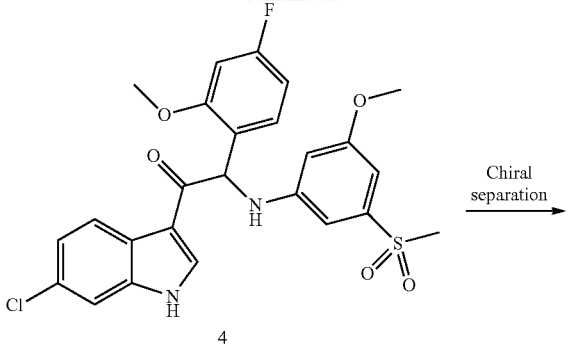

Synthesis of Intermediate 4a

A stirred solution of 6-chloro-1H-indole [CAS 17422-33-2] (2.23 g, 14.7 mmol) in CH$_2$Cl$_2$ (125 mL) under N$_2$-flow, was cooled to 0° C. using an ice-bath. A solution of diethylaluminum chloride 1M in hexane (22.1 mL, 22.1 mmol) was added dropwise and the mixture was stirred for 10 min at 0° C. Then, a solution of 2-(4-fluoro-2-methoxyphenyl)acetyl chloride 1a (4.47 g, 22.1 mmol, synthesis: see Example 1) in CH$_2$Cl$_2$ (30 mL) was added dropwise over a period of 50 min and the resulting mixture was kept at 0° C. for 1 h and was subsequently stirred at 10° C. for 1 h. After cooling to 0° C. again, the reaction was quenched by the slow addition of a solution of potassium sodium tartrate tetrahydrate [CAS 6100-16-9] (8.31 g, 29.4 mmol) in water (9 mL) and the mixture was allowed to warm to room temperature over 1 h. The reaction mixture was diluted by the addition of 2-methyl-THF (150 mL) and stirred for 30 min at room temperature. Na$_2$SO$_4$ (30 g) was added and after stirring for 30 min, the mixture was filtered over Dicalite®. The filter cake was washed several times with 2-methyl-THF and the combined filtrates were concentrated under vacuum to a residual volume of 25 mL. After standing for 2 h, a precipitate was formed and the precipitate was filtered off and dried under vacuum to provide 1-(6-chloro-1H-indol-3-yl)-2-(4-fluoro-2-methoxyphenyl)ethanone 4a (2.85 g).

Synthesis of Compound 4 and chiral separation of Enantiomers 4A and 4B

A solution of 1-(6-chloro-1H-indol-3-yl)-2-(4-fluoro-2-methoxyphenyl)ethanone 4a (0.8 g, 2.52 mmol) in THF (40 mL) was stirred under N$_2$-flow and cooled on an ice-bath. Phenyltrimethylammonium tribromide [CAS 4207-56-1] (0.99 g, 2.64 mmol) was added portionwise and the mixture was stirred at 0° C. for 1 h and subsequently at room temperature for 1 h. The solids were removed from the reaction mixture by filtration. The filtrate, containing crude 2-bromo-1-(6-chloro-1H-indol-3-yl)-2-(4-fluoro-2-methoxyphenyl)ethanone 4b, was mixed with 3-methoxy-5-(methylsulfonyl)aniline [CAS 62606-02-4] (0.56 g, 2.77 mmol) and diisopropylethylamine (1.3 mL, 7.55 mmol) and the solvents were evaporated under reduced pressure. The residue was taken up with CH$_3$CN (50 mL) and heated under reflux for 18 h. After cooling to room temperature, the reaction mixture was poured out in water (250 mL). The products were extracted with 2-methyl-THF (2×) and the combined organic layers were dried over MgSO$_4$, filtered and evaporated under reduced pressure. The residue was stirred up in EtOAc (7.5 mL) and the solids were filtered off. The filtrate was evaporated under reduced pressure and the residue was purified by flash chromatography on silica (Stationary phase: Grace Reveleris® silica 40 g, Mobile phase: heptane/EtOAc gradient 100/0 to 0/100). The fractions containing product were combined and evaporated, and the residue was further purified via Preparative HPLC (Stationary phase: Uptisphere C18 ODB—10 µm, 200 g, 5 cm, Mobile phase: 0.25% $NH_4HCO_3$ solution in water, $CH_3CN$). The product fractions were combined and evaporated under reduced pressure, and the residue was co-evaporated with MeOH. The solid residue was stirred up in $Et_2O$ (7.5 mL), filtered off and dried under vacuum at 50° C. to provide racemic 1-(6-chloro-1H-indol-3-yl)-2-(4-fluoro-2-methoxyphenyl)-2-((3-methoxy-5-(methylsulfonyl)phenyl)amino)ethanone (Compound 4, 352 mg).

Chiral separation of the enantiomers of Compound 4 (352 mg) was done via Normal Phase Chiral separation (Stationary phase: AS 500 g 20 µm, Mobile phase: 100% MeOH). The product fractions were combined and evaporated under reduced pressure. The first eluted product was stirred up in $CH_2Cl_2$ (5 mL), filtered off and dried under vacuum at 40° C. to provide Enantiomer 4A (56 mg). The second eluted product was stirred up in $CH_2Cl_2$ (3.5 mL), filtered off and dried under vacuum at 40° C. to provide Enantiomer 4B (68 mg).

Compound 4:

$^1$H NMR (500 MHz, DMSO-$d_6$) δ ppm 3.09 (s, 3 H) 3.73 (s, 3 H) 3.99 (s, 3 H) 6.24 (d, J=7.9 Hz, 1 H) 6.59 (s, 2 H) 6.74 (td, J=8.4, 2.2 Hz, 1 H) 6.92 (s, 1 H) 6.97 (dd, J=11.2, 2.4 Hz, 1 H) 7.06 (d, J=7.9 Hz, 1 H) 7.23 (dd, J=8.5, 1.6 Hz, 1 H) 7.37 (dd, J=8.4, 7.1 Hz, 1 H) 7.54 (d, J=1.6 Hz, 1 H) 8.15 (d, J=8.5 Hz, 1 H) 8.47 (s, 1 H) 11.82-12.42 (bs, 1 H)

LC/MS (method LC-A): $R_t$ 1.12 min, MH$^+$ 517

Enantiomer 4A:

$^1$H NMR (360 MHz, DMSO-$d_6$) δ ppm 3.09 (s, 3 H) 3.72 (s, 3 H) 3.99 (s, 3 H) 6.22 (d, J=7.75 Hz, 1 H) 6.56-6.60 (m, 2 H) 6.73 (td, J=8.45, 2.51 Hz, 1 H) 6.91 (t, J=1.83 Hz, 1 H) 6.96 (dd, J=11.38, 2.51 Hz, 1 H) 7.06 (d, J=7.73 Hz, 1 H) 7.20 (dd, J=8.49, 1.96 Hz, 1 H) 7.36 (dd, J=8.66, 6.83 Hz, 1 H) 7.52 (d, J=1.94 Hz, 1 H) 8.13 (d, J=8.49 Hz, 1 H) 8.45 (s, 1 H) 12.24 (br. s, 1 H)

LC/MS (method LC-A): $R_t$ 1.15 min, MH$^+$ 517

$[α]_D^{20}$: +129.9° (c 0.525, DMF)

Chiral SFC (method SFC-N): $R_t$ 2.77 min, MH$^+$ 517, chiral purity 100%.

Melting point: 245° C.

Enantiomer 4B:

$^1$H NMR (360 MHz, DMSO-$d_6$) δ ppm 3.08 (s, 3 H) 3.71 (s, 3 H) 3.98 (s, 3 H) 6.22 (d, J=7.75 Hz, 1 H) 6.56-6.60 (m, 2 H) 6.73 (td, J=8.49, 2.47 Hz, 1 H) 6.91 (t, J=1.65 Hz, 1 H) 6.96 (dd, J=11.35, 2.48 Hz, 1 H) 7.06 (d, J=7.79 Hz, 1 H) 7.20 (dd, J=8.51, 1.93 Hz, 1 H) 7.36 (dd, J=8.63, 6.84 Hz, 1 H) 7.52 (d, J=1.92 Hz, 1 H) 8.13 (d, J=8.51 Hz, 1 H) 8.45 (s, 1 H) 12.10 (br. s, 1 H)

LC/MS (method LC-A): $R_t$ 1.15 min, MH$^+$ 517

$[α]_D^{20}$: −123.3° (c 0.544, DMF)

Chiral SFC (method SFC-N): $R_t$ 3.52 min, MH$^+$ 517, chiral purity 100%.

Melting point: 247° C.

Example 5 synthesis 2-(4-fluoro-2-methoxyphenyl)-1-(6-methoxy-1H-indol-3-yl)-2-((3-methoxy-5-(methylsulfonyl)phenyl)amino)ethanone (Compound 5) and chiral separation into Enantiomers 5A and 5B

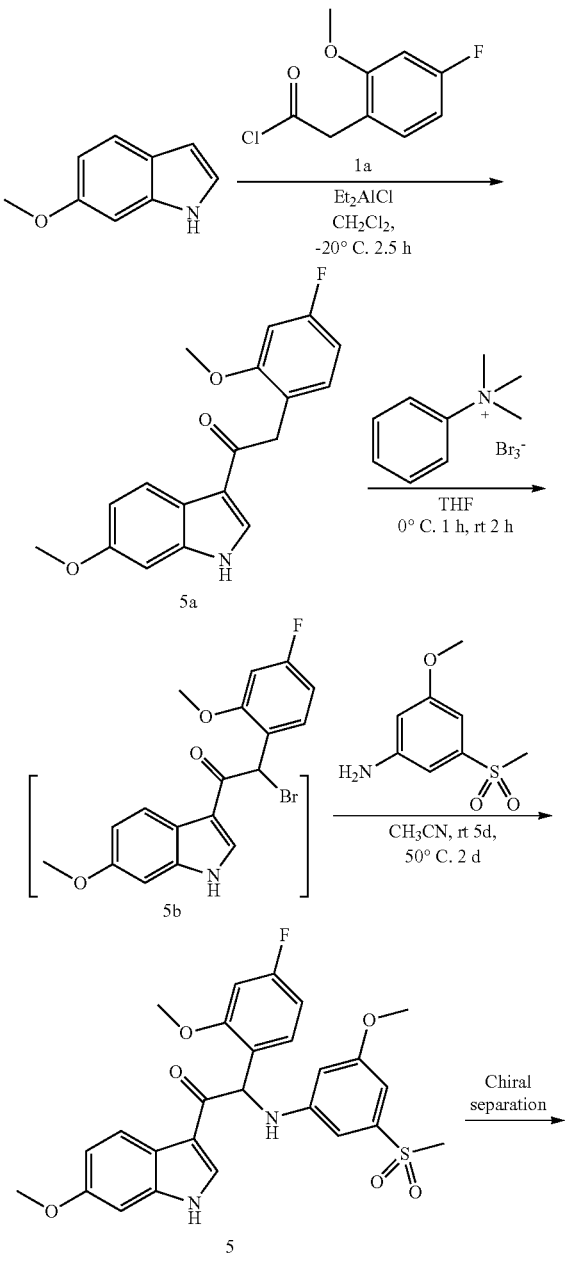

Enantiomers 5A and 5B

Synthesis of Intermediate 5a

A stirred solution of 6-methoxy-1H-indole [CAS 3189-13-7] (2.54 g, 17.3 mmol) in $CH_2Cl_2$ (100 mL) under $N_2$-flow, was cooled to −22° C. using a cryostat-controlled acetone cooling bath. A solution of diethylaluminum chloride 1 M in hexane (25.9 mL, 25.9 mmol) was added dropwise and the mixture was stirred at −22° C. for 20 min. Then, a solution of 2-(4-fluoro-2-methoxyphenyl)acetyl chloride 1a (5.24 g, 25.9 mmol, synthesis: see Example 1) in CH$_2$Cl$_2$ (60 mL) was added dropwise over a period of 90 min while keeping the internal temperature below −20° C. and the resulting mixture was kept at −20° C. for 2.5 h. The reaction was quenched by the slow addition of a solution of potassium sodium tartrate tetrahydrate [CAS 6100-16-9] (9.74 g, 34.5 mmol) in water (10 mL) and the mixture was stirred at −20° C. for 30 min and subsequently at room temperature for 1 h. The reaction mixture was diluted by the addition of THF (300 mL) and stirred for 1 h at room temperature. Na$_2$SO$_4$ (32 g) was added and after stirring for 18 h, the mixture was filtered over Dicalite®. The filter cake was washed several times with THF and the combined filtrates were concentrated under vacuum to a residual volume of 7.5 mL. After standing for 4 h, a precipitate was formed and the precipitate was filtered off and dried under vacuum at 50° C. to provide 2-(4-fluoro-2-methoxy-phenyl)-1-(6-methoxy-1H-indol-3-yl)ethanone 5a (2.21 g).

Synthesis of Compound 5 and chiral separation of Enantiomers 5A and 5B

A solution of 2-(4-fluoro-2-methoxyphenyl)-1-(6-methoxy-1H-indol-3-yl)ethanone 5a (2.2 g, 7.02 mmol) in THF (150 mL) was stirred under N$_2$-flow and cooled on an ice-bath. Phenyltrimethylammonium tribromide [CAS 4207-56-1] (2.77 g, 7.37 mmol) was added portionwise and the mixture was stirred at 0° C. for 1 h and subsequently at room temperature for 2 h. 3-Methoxy-5-(methylsulfonyl) aniline [CAS 62606-02-4] (4.24 g, 21.1 mmol) was added and approximately 125 mL solvent was evaporated under reduced pressure. CH$_3$CN (50 mL) was added and the reaction mixture was stirred at room temperature for 5 days and subsequently at 50° C. for 2 days. After cooling to room temperature, the reaction mixture was poured out in water (200 mL). The products were extracted with 2-methyl-THF (2×) and the combined organic layers were washed with brine, dried over MgSO$_4$, filtered and evaporated under reduced pressure. The residue was purified by flash chromatography on silica (Stationary phase: Grace Reveleris® silica 120 g, Mobile phase: heptane/EtOAc gradient 100/0 to 0/100). The fractions containing product were combined and washed with 1N HCl (100 mL), an aqueous saturated solution of NaHCO$_3$, dried with MgSO$_4$, filtered and evaporated under reduced pressure. The residue was crystallized from a mixture of CH$_2$Cl$_2$ (10 mL) and diisopropyl-ether (15 mL), filtered off and dried under vacuum at 50° C. to provide racemic 2-(4-fluoro-2-methoxyphenyl)-1-(6-methoxy-1H-indol-3-yl)-2-((3-methoxy-5-(methylsulfonyl)phenyl) amino)ethanone (Compound 5, 2.25 g). A small aliquot of Compound 5 (150 mg) was further purified by slurring up in MeOH (4 mL) for 2 h. The solids were filtered off and dried under vacuum at 50° C. to provide racemic 2-(4-fluoro-2-methoxyphenyl)-1-(6-methoxy-1H-indol-3-yl)-2-((3-methoxy-5-(methylsulfonyl)phenyl)amino)ethanone (Compound 5, 112 mg). Chiral separation of the enantiomers of Compound 5 (2.1 g) was done via Normal Phase Chiral separation (Stationary phase: (S,S)-Whelk-O 1, Mobile phase: 100% EtOH). The product fractions were combined and evaporated. The first eluted product was stirred up in MeOH (6 mL), filtered off and dried under vacuum at 40° C. to provide Enantiomer 5A (825 mg). The second eluted product was stirred up in MeOH (5 mL), filtered off and dried under vacuum at 40° C. to provide Enantiomer 5B (784 mg).

Compound 5:

$^1$H NMR (400 MHz, DMSO-d$_6$) δ ppm 3.08 (s, 3 H) 3.72 (s, 3 H) 3.76 (s, 3 H) 4.00 (s, 3 H) 6.19 (d, J=7.66 Hz, 1 H) 6.55-6.61 (m, 2 H) 6.72 (td, J=8.47, 2.49 Hz, 1 H) 6.83 (dd, J=8.71, 2.30 Hz, 1 H) 6.90 (t, J=1.65 Hz, 1 H) 6.92-6.98 (m, 2 H) 7.00 (d, J=7.69 Hz, 1 H) 7.36 (dd, J=8.60, 6.85 Hz, 1 H) 8.02 (d, J=8.71 Hz, 1 H) 8.29 (s, 1 H) 11.85 (br. s, 1 H)

LC/MS (method LC-A): R$_t$ 1.01 min, MH$^+$ 513

Enantiomer 5A:

$^1$H NMR (400 MHz, DMSO-d$_6$) δ ppm 3.08 (s, 3 H) 3.72 (s, 3 H) 3.77 (s, 3 H) 4.00 (s, 3 H) 6.20 (d, J=7.68 Hz, 1 H) 6.56-6.61 (m, 2 H) 6.72 (td, J=8.48, 2.48 Hz, 1H) 6.83 (dd, J=8.72, 2.30 Hz, 1 H) 6.91 (t, J=1.65 Hz, 1 H) 6.92-6.98 (m, 2 H) 7.01 (d, J=7.70 Hz, 1 H) 7.36 (dd, J=8.61, 6.85 Hz, 1 H) 8.02 (d, J=8.71 Hz, 1 H) 8.30 (s, 1 H) 11.76 (br. s, 1 H)

LC/MS (method LC-A): R$_t$ 1.04 min, MH$^+$ 513

[α]$_D^{20}$: −127.5° (c 0.6, DMF)

Chiral SFC (method SFC-I): R$_t$ 3.01 min, MH$^+$ 513, chiral purity 100%.

Melting point: 190° C.

Enantiomer 5B:

$^1$H NMR (400 MHz, DMSO-d$_6$) δ ppm 3.08 (s, 3 H) 3.72 (s, 3 H) 3.77 (s, 3 H) 4.00 (s, 3 H) 6.20 (d, J=7.67 Hz, 1 H) 6.55-6.62 (m, 2 H) 6.73 (td, J=8.48, 2.49 Hz, 1 H) 6.83 (dd, J=8.72, 2.30 Hz, 1 H) 6.91 (t, J=1.65 Hz, 1 H) 6.93-6.98 (m, 2 H) 7.01 (d, J=7.68 Hz, 1 H) 7.37 (dd, J=8.61, 6.84 Hz, 1 H) 8.03 (d, J=8.71 Hz, 1 H) 8.30 (s, 1 H) 11.82 (br. s, 1 H)

LC/MS (method LC-A): R$_t$ 1.04 min, MH$^+$ 513

[α]$_D^{20}$: +125.3° (c 0.455, DMF)

Chiral SFC (method SFC-I): R$_t$ 2.51 min, MH$^+$ 513, chiral purity 100%.

Melting point: 204° C.

Example 6

2-(4-fluoro-2-methoxyphenyl)-1-(7-fluoro-5-methyl-1H-indol-3-yl)-2-((3-methoxy-5-(methylsulfonyl) phenyl)amino)ethanone (Compound 6) and chiral separation into Enantiomers 6A and 6B

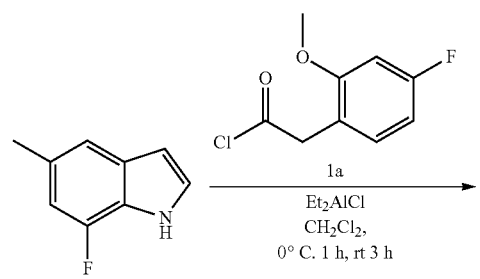

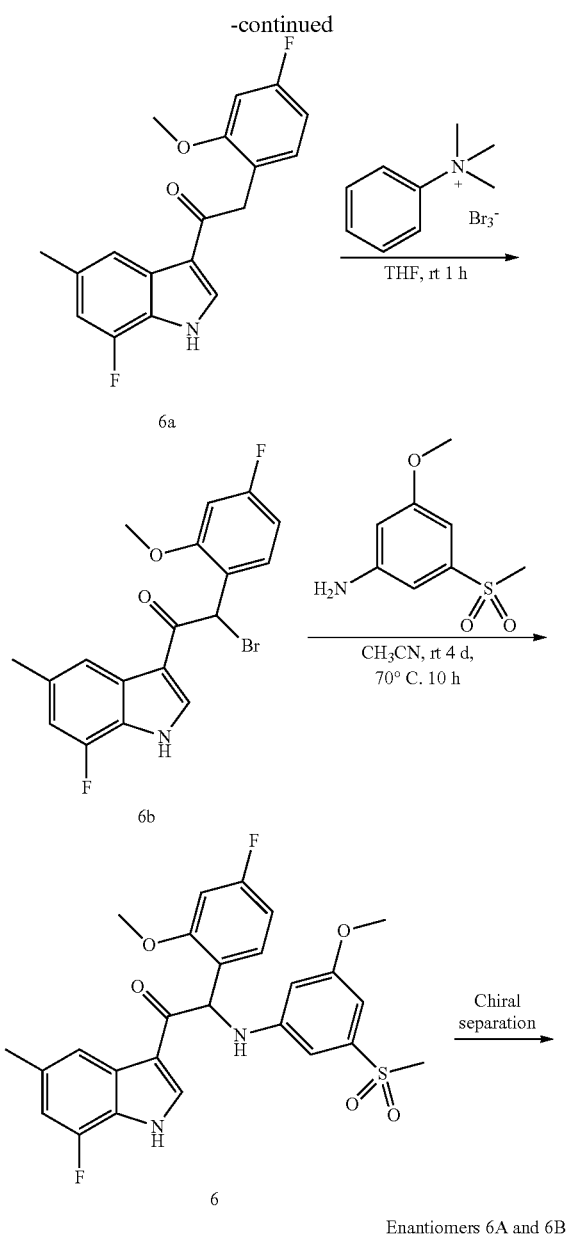

6a

6b

6

Enantiomers 6A and 6B

Synthesis of Intermediate 6a

A stirred solution of 7-fluoro-5-methyl-1H-indole [CAS 442910-91-0] (2.54 g, 17.0 mmol) in CH$_2$Cl$_2$ (150 mL) under N$_2$-flow, was cooled to 0° C. using an ice-bath. A solution of diethylaluminum chloride 1M in hexane (25.6 mL, 25.6 mmol) was added dropwise and the mixture was stirred at 0° C. for 30 min. Then, a solution of 2-(4-fluoro-2-methoxyphenyl)acetyl chloride 1a (5.18 g, 25.6 mmol, synthesis: see Example 1) in CH$_2$Cl$_2$ (150 mL) was added dropwise and the resulting mixture was stirred at 0° C. for 1 h and subsequently at room temperature for 3 h. The reaction was poured out into ice-water containing excess potassium sodium tartrate tetrahydrate [CAS 6100-16-9]. The mixture was filtered over Dicalite® and the filter cake was washed several times with THF. The organic layer was separated, washed with water, dried over MgSO$_4$, filtered and evaporated under reduced pressure. The residue was suspended in CH$_2$Cl$_2$ (20 mL). The solids were filtered off, washed with a small amount of a mixture of CH$_2$Cl$_2$/heptane (1/1) and dried under vacuum at 50° C. to provide 2-(4-fluoro-2-methoxyphenyl)-1-(7-fluoro-5-methyl-1H-indol-3-yl)ethanone 6a (4.13 g).

Synthesis of Intermediate 6b

A solution of 2-(4-fluoro-2-methoxyphenyl)-1-(7-fluoro-5-methyl-1H-indol-3-yl)-ethanone 6a (4.11 g, 13.0 mmol) in THF (100 mL) was stirred under N$_2$-flow and cooled on an ice-bath. A solution of phenyltrimethylammonium tribromide [CAS 4207-56-1] (5.39 g, 14.3 mmol) in THF (150 mL) was added dropwise and the mixture was stirred at room temperature for 1 h. The solids were removed by filtration, washed with THF and the combined filtrates were evaporated under reduced pressure. The residue was triturated with a small amount of CH$_2$Cl$_2$, the solids were isolated by filtration and dried under vacuum to provide 2-bromo-2-(4-fluoro-2-methoxyphenyl)-1-(7-fluoro-5-methyl-1H-indol-3-yl)ethanone 6b (4.81 g) as a white powder.

Synthesis of Compound 6 and chiral separation of Enantiomers 6A and 6B

A solution of 2-bromo-2-(4-fluoro-2-methoxyphenyl)-1-(7-fluoro-5-methyl-1H-indol-3-yl)ethanone 6b (1.02 g, 2.59 mmol), 3-methoxy-5-(methylsulfonyl)aniline [CAS 62606-02-4] (782 mg, 3.89 mmol) and diisopropylethylamine (670 µL, 3.89 mmol) in CH$_3$CN (25 mL) was stirred at room temperature for 4 days and the mixture was subsequently heated at 70° C. for 10 h. After cooling to room temperature, the solvents were evaporated under reduced pressure. The residue was taken up with CH$_2$Cl$_2$, washed with 0.5N HCl and water, dried over MgSO$_4$, filtered and evaporated under reduced pressure. The residue was purified by column chromatography on silica (Stationary phase: Biotage® SNAP Ultra 100 g, Mobile phase: EtOAc:EtOH (3:1)/heptane gradient 0/100 to 50/50). The fractions containing product were combined and evaporated under reduced pressure to provide racemic 2-(4-fluoro-2-methoxyphenyl)-1-(7-fluoro-5-methyl-1H-indol-3-yl)-2-((3-methoxy-5-(methylsulfonyl)phenyl)amino)ethanone (Compound 6, 747 mg) as a white solid.

Chiral separation of the enantiomers of Compound 6 (747 mg) was performed via Preparative SFC (Stationary phase: Chiralpak® Diacel AD 20×250 mm, Mobile phase: CO$_2$, EtOH with 0.2% iPrNH$_2$). The product fractions were combined, evaporated under reduced pressure and dried under vacuum at 50° C. The first eluted product provided Enantiomer 6A (275 mg) as a white amorphous solid. The second eluted product provided Enantiomer 6B (259 mg) as a white amorphous powder.

Compound 6:
LC/MS (method LC-A): R$_t$ 1.13 min, MH$^+$ 515
Enantiomer 6A:
$^1$H NMR (360 MHz, DMSO-d$_6$) δ ppm 2.39 (s, 3 H) 3.09 (s, 3 H) 3.72 (s, 3 H) 3.98 (s, 3 H) 6.24 (d, J=7.78 Hz, 1 H) 6.55-6.62 (m, 2 H) 6.73 (td, J=8.48, 2.49 Hz, 1 H) 6.88-6.99 (m, 3 H) 7.01 (d, J=7.80 Hz, 1 H) 7.35 (dd, J=8.61, 6.83 Hz, 1 H) 7.79 (s, 1 H) 8.40 (s, 1 H) 12.49 (br. s, 1 H)
LC/MS (method LC-B): R$_t$ 2.04 min, MH$^+$ 515
$[α]_D^{20}$: +134.0° (c 0.332, DMF)
Chiral SFC (method SFC-O): R$_t$ 2.24 min, MH$^+$ 515, chiral purity 100%.

Enantiomer 6B $^1$H NMR (360 MHz, DMSO-d$_6$) δ ppm 2.39 (s, 3 H) 3.10 (s, 3 H) 3.72 (s, 3 H) 3.98 (s, 3 H) 6.25 (d, J=7.79 Hz, 1 H) 6.57-6.61 (m, 2 H) 6.74 (td, J=8.48, 2.48 Hz, 1 H) 6.89-6.99 (m, 3 H) 7.02 (d, J=7.80 Hz, 1 H) 7.36 (dd, J=8.62, 6.83 Hz, 1 H) 7.79 (s, 1 H) 8.41 (s, 1 H) 12.47 (br. s, 1 H)

LC/MS (method LC-B): R$_t$ 2.04 min, MH$^+$ 515

[α]$_D^{20}$: −129.2° (c 0.288, DMF)

Chiral SFC (method SFC-O): R$_t$ 3.40 min, MH$^+$ 515, chiral purity 100%.

Example 7 synthesis of 1-(5,6-difluoro-1H-indol-3-yl)-2-(4-fluoro-2-methoxy-phenyl)-2-((3-methoxy-5-(methylsulfonyl)phenyl)amino)ethanone (Compound 7) and chiral separation in Enantiomers 7A and 7B

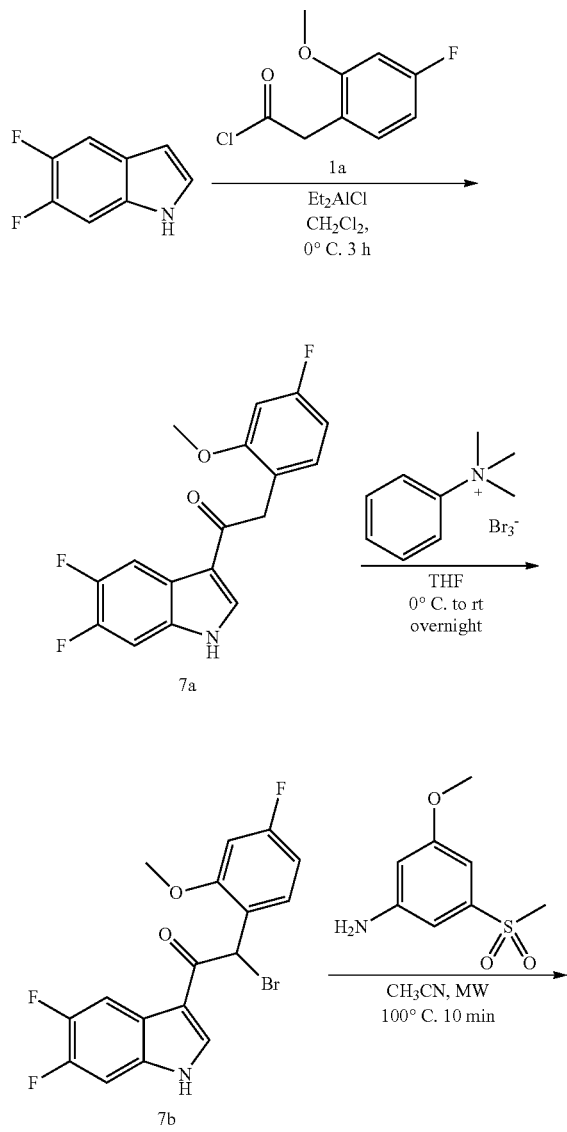

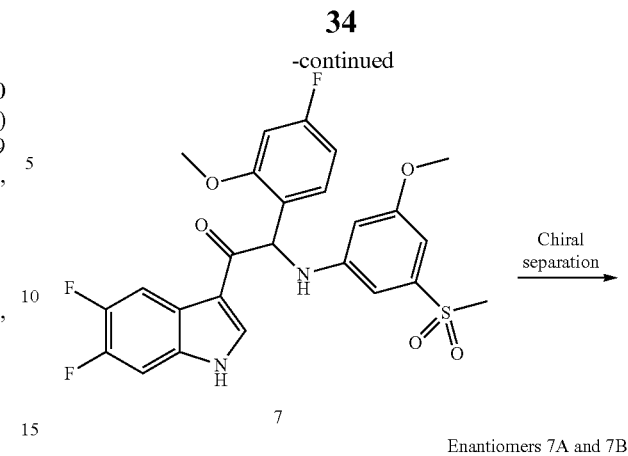

Enantiomers 7A and 7B

Synthesis of Intermediate 7a

A solution of diethylaluminum chloride 1M in hexane (19.9 mL, 19.9 mmol) was added dropwise at 0° C. to a solution of 5,6-difluoro-1H-indole [CAS 169674-01-5] (2.0 g, 13.1 mmol) in CH$_2$Cl$_2$ (24 mL). After 30 min at 0° C., a solution of 2-(4-fluoro-2-methoxyphenyl)acetyl chloride 1a (4.0 g, 19.6 mmol, synthesis: see Example 1) in CH$_2$Cl$_2$ (24 mL) was slowly added. The reaction was stirred at 0° C. for 3 h. 1N Rochelle salt solution (50 mL) was added and the reaction mixture was vigorously stirred at room temperature for 1 h. The precipitate was filtered off and partitioned between in EtOAc and 1 N HCl. The aqueous phase was extracted with EtOAc. The organic phases were combined, washed with brine, dried over MgSO$_4$, filtered and concentrated under reduced pressure to give 1-(5,6-difluoro-1H-indol-3-yl)-2-(4-fluoro-2-methoxyphenyl)ethanone 7a (4.0 g).

Synthesis of Intermediate 7b

A solution of phenyltrimethylammonium tribromide [CAS 4207-56-1] (1.9 g, 2.37 mmol) in THF (30 mL) was added dropwise at 0° C. to a solution of 1-(5,6-difluoro-1H-indol-3-yl)-2-(4-fluoro-2-methoxyphenyl)ethanone 7a (1.5 g, 4.70 mmol) in THF (50 mL). The mixture was stirred at 0° C. for 15 min and at room temperature overnight. The precipitate was filtered off and washed with EtOAc. The filtrate was concentrated under reduced pressure. The residue was taken up with a minimum of acetonitrile. The precipitate was filtered off to give 2-bromo-1-(5,6-difluoro-1H-indol-3-yl)-2-(4-fluoro-2-methoxyphenyl)ethanone 7b (1.9 g).

Synthesis of Compound 7 and chiral separation of Enantiomers 7A and 7B

A mixture of 2-bromo-1-(5,6-difluoro-1H-indol-3-yl)-2-(4-fluoro-2-methoxyphenyl)-ethanone 7b (0.800 g, 2.01 mmol) and 3-methoxy-5-(methylsulfonyl)aniline [CAS 62606-02-4] (1.2 g, 6.03 mmol) in acetonitrile (8 mL) was irradiated in a microwave oven at 100° C. for 10 min. The reaction mixture was diluted with EtOAc and washed with 1 N HCl. The organic phase was washed with an aqueous saturated NaHCO$_3$ solution and brine, dried over MgSO$_4$, filtered and concentrated under reduced pressure. The residue was crystallized from acetonitrile to afford 1-(5,6-difluoro-1H-indol-3-yl)-2-(4-fluoro-2-methoxyphenyl)-2-

((3-methoxy-5-(methylsulfonyl)phenyl)amino)ethanone (Compound 7, 640 mg) as a racemic mixture.

Chiral separation of the enantiomers of Compound 7 (596 mg) was performed via Preparative Chiral SFC (Stationary phase: Chiralpak® IA 5 µm 250×20 mm, Mobile phase: 70% $CO_2$, 30% MeOH) yielding 250 mg of the first eluted enantiomer and 250 mg of the second eluted enantiomer. The first eluted enantiomer was solidified by trituration with $Et_2O$ to afford Enantiomer 7A (194 mg) as an amorphous powder. The second eluted enantiomer was solidified by trituration with $Et_2O$ to afford Enantiomer 7B (212 mg) as an amorphous powder.

Compound 7:

$^1$H NMR (300 MHz, DMSO-$d_6$) δ ppm 3.09 (s, 3 H) 3.72 (s, 3 H) 3.98 (s, 3 H) 6.23 (d, J=7.8 Hz, 1 H) 6.57-6.61 (m, 2 H) 6.74 (td, J=8.5, 2.5 Hz, 1 H) 6.91 (s, 1 H) 6.96 (dd, J=11.4, 2.5 Hz, 1 H) 7.06 (d, J=7.9 Hz, 1 H) 7.36 (dd, J=8.6, 6.9 Hz, 1 H) 7.54 (dd, J=10.8, 7.0 Hz, 1 H) 8.01 (dd, J=11.2, 8.1 Hz, 1 H) 8.48 (s, 1 H) 12.19 (br. s., 1 H)

LC-MS (method LC-D) $R_t$ 3.3 min, MH$^+$ 519

Enantiomer 7A:

$^1$H NMR (500 MHz, DMSO-$d_6$) δ ppm 3.08 (s, 3 H) 3.72 (s, 3 H) 3.98 (s, 3 H) 6.22 (d, J=7.9 Hz, 1 H) 6.55-6.60 (m, 2 H) 6.74 (td, J=8.4, 2.4 Hz, 1 H) 6.88-6.92 (m, 1 H) 6.95 (dd, J=11.2, 2.4 Hz, 1 H) 7.04 (d, J=7.9 Hz, 1 H) 7.36 (dd, J=8.4, 6.9 Hz, 1 H) 7.53 (dd, J=10.7, 6.9 Hz, 1 H) 8.00 (dd, J=11.2, 8.0 Hz, 1 H) 8.47 (s, 1 H) 12.18 (br. s., 1 H)

LC/MS (method LC-C): $R_t$ 3.00 min, MH$^+$ 519

$[α]_D^{20}$: +103.9° (c 0.282, DMF)

Chiral SFC (method SFC-G): $R_t$ 3.16 min, MH$^+$ 519, chiral purity 100%.

Enantiomer 7B:

$^1$H NMR (500 MHz, DMSO-$d_6$) δ ppm 3.08 (s, 3 H) 3.72 (s, 3 H) 3.98 (s, 3 H) 6.22 (d, J=7.9 Hz, 1 H) 6.55-6.61 (m, 2 H) 6.74 (td, J=8.4, 2.4 Hz, 1 H) 6.91 (s, 1 H) 6.96 (dd, J=11.3, 2.4 Hz, 1 H) 7.04 (d, J=7.9 Hz, 1 H) 7.36 (dd, J=8.5, 6.9 Hz, 1 H) 7.53 (dd, J=10.7, 6.9 Hz, 1 H) 8.00 (dd, J=11.0, 8.2 Hz, 1 H) 8.47 (s, 1 H) 12.18 (br. s., 1 H)

LC/MS (method LC-C): $R_t$ 3.00 min, MH$^+$ 519

$[α]_D^{20}$: -109.2° (c 0.285, DMF)

Chiral SFC (method SFC-G): $R_t$ 3.92 min, MH$^+$ 519, chiral purity 99.17%.

Example 8 synthesis of 2-(4-fluoro-2-methoxyphenyl)-1-(5-fluoro-7-methyl-1H-indol-3-yl)-2-((3-methoxy-5-(methylsulfonyl)phenyl)amino)ethanone (Compound 8) and chiral separation into Enantiomers 8A and 8B

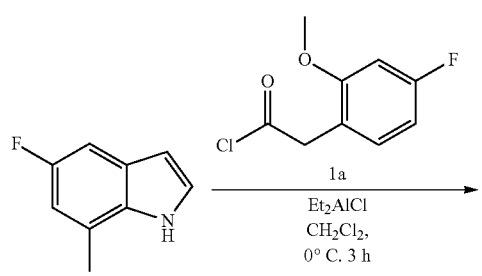

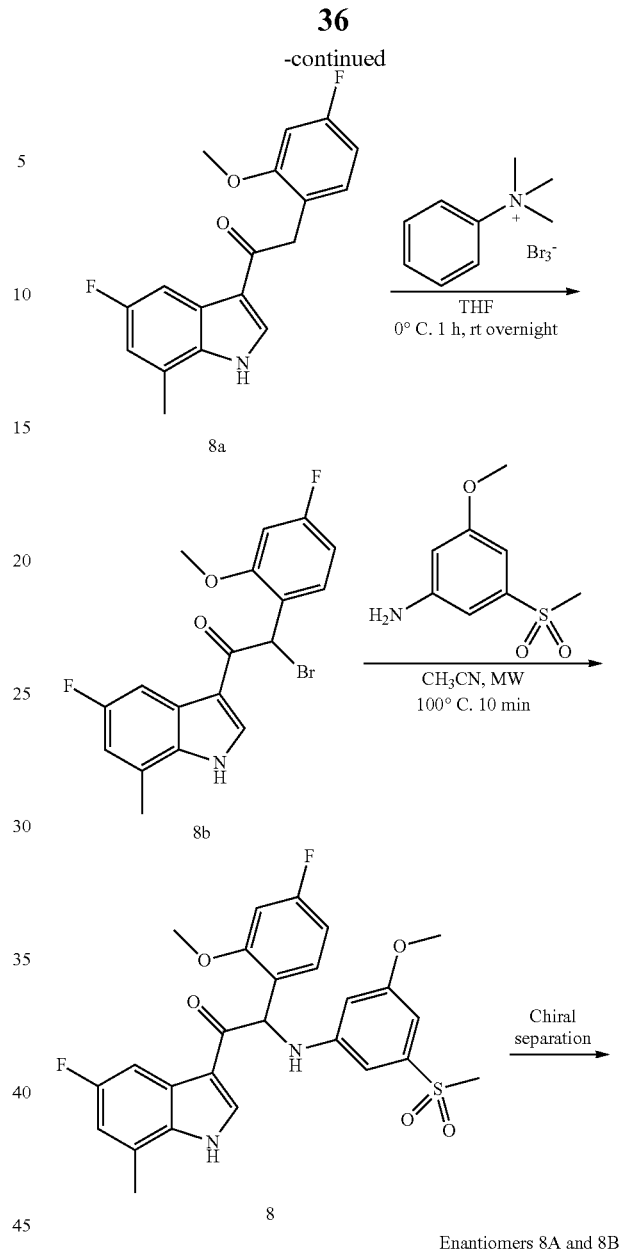

Synthesis of Intermediate 8a

Diethylaluminum chloride 1M in hexane (22 mL, 22 mmol) was added dropwise at 0° C. to a solution of 5-fluoro-7-methyl-1H-indole [CAS 1082041-52-8] (1.62 g, 10.9 mmol) in $CH_2Cl_2$ (45 mL). After 30 min at 0° C., a solution of 2-(4-fluoro-2-methoxyphenyl)acetyl chloride 1a (3.3 g, 16.3 mmol, synthesis: see Example 1) in $CH_2Cl_2$ (30 mL) was added slowly at 0° C. The reaction was stirred at 0° C. for 3 h. Rochelle salt solution (1 N, 75 mL) was added and the reaction mixture was stirred at room temperature overnight. The precipitate was filtered off and partitioned between in EtOAc and 1 N HCl. The organic phase was washed with 1 N HCl and brine, dried over $MgSO_4$, filtered and concentrated under reduced pressure. The residue was taken up with a minimum amount of EtOAc. The precipitate was filtered off to give 2-(4-fluoro-2-methoxyphenyl)-1-(5-fluoro-7-methyl-1H-indol-3-yl)ethanone 8a (2.4 g).

Synthesis of Intermediate 8b

A solution of phenyltrimethylammonium tribromide [CAS 4207-56-1] (2.2 g, 5.85 mmol) in THF (60 mL) was added dropwise at 0° C. to a solution of 2-(4-fluoro-2-methoxyphenyl)-1-(5-fluoro-7-methyl-1H-indol-3-yl)ethanone 8a (1.66 g, 5.26 mmol) in THF (45 mL). The mixture was stirred at 0° C. for 1 h and at room temperature overnight. The precipitate was filtered off and washed with EtOAc. The filtrate was concentrated under reduced pressure to give 2-bromo-2-(4-fluoro-2-methoxyphenyl)-1-(5-fluoro-7-methyl-1H-indol-3-yl)ethanone 8b (1.9 g).

Synthesis of Compound 8 and chiral separation of Enantiomers 8A and 8B

A mixture of 2-bromo-2-(4-fluoro-2-methoxyphenyl)-1-(5-fluoro-7-methyl-1H-indol-3-yl)ethanone 8b (0.100 g, 0.254 mmol) and 3-methoxy-5-(methylsulfonyl)aniline [CAS 62606-02-4] (0.155 g, 0.770 mmol) in acetonitrile (1 mL) was irradiated in a microwave oven at 100° C. for 10 min. The reaction mixture was diluted with EtOAc and washed with 1 N HCl. The organic phase was washed with an aqueous saturated NaHCO$_3$ solution and brine, dried over MgSO$_4$, filtered and concentrated under reduced pressure. The residue was crystallized from EtOAc and heptane to afford 2-(4-fluoro-2-methoxyphenyl)-1-(5-fluoro-7-methyl-1H-indol-3-yl)-2-((3-methoxy-5-(methylsulfonyl) phenyl)amino)ethanone (Compound 8, 95 mg) as a racemic mixture.

Chiral separation of the enantiomers of Compound 8 (491 mg) was performed via Preparative Chiral SFC (Stationary phase: Chiralpak IC 5 μm 250×30 mm, Mobile phase: 60% CO$_2$, 40% iPrOH) yielding 224 mg of the first eluted enantiomer and 212 mg of the second eluted enantiomer. The first eluted enantiomer was crystallized from Et$_2$O and a few drops of CH$_3$CN to afford Enantiomer 8A (174 mg) as white powder. The second eluted enantiomer was crystallized from Et$_2$O and a few drops of CH$_3$CN to afford Enantiomer 8B (164 mg) as a white powder.

Compound 8:
$^1$H NMR (300 MHz, DMSO-d$_6$) δ ppm 2.47 (s, 3 H) 3.09 (s, 3 H) 3.72 (s, 3 H) 4.00 (s, 3 H) 6.24 (d, J=7.7 Hz, 1 H) 6.55-6.64 (m, 2 H) 6.73 (td, J=8.4, 2.4 Hz, 1 H) 6.87-6.98 (m, 3 H) 7.04 (d, J=7.7 Hz, 1 H) 7.36 (dd, J=8.6, 6.8 Hz, 1 H) 7.66 (dd, J=9.7, 2.5 Hz, 1 H) 8.46 (s, 1 H) 12.23 (br. s., 1 H)
LC-MS (method LC-E): R$_t$ 8.5 min, MH$^+$ 515

Enantiomer 8A:
$^1$H NMR (500 MHz, DMSO-d$_6$) δ ppm 2.47 (s, 3 H) 3.09 (s, 3 H) 3.72 (s, 3 H) 4.00 (s, 3 H) 6.24 (d, J=7.9 Hz, 1 H) 6.53-6.65 (m, 2 H) 6.73 (td, J=8.8, 2.4 Hz, 1 H) 6.88-6.99 (m, 3 H) 7.05 (d, J=7.9 Hz, 1 H) 7.36 (dd, J=8.8, 6.9 Hz, 1 H) 7.66 (dd, J=9.6, 2.4 Hz, 1 H) 8.46 (s, 1 H) 12.24 (br. s., 1 H)
LC/MS (method LC-C): R$_t$ 3.07 min, MH$^+$ 515
[α]$_D^{20}$: +101.10 (c 0.282, DMF)
Chiral SFC (method SFC-B): R$_t$ 3.31 min, MH$^+$ 515, chiral purity 100%.
Melting point: 208° C.

Enantiomer 8B:
$^1$H NMR (500 MHz, DMSO-d$_6$) δ ppm 2.47 (s, 3 H) 3.09 (s, 3 H) 3.72 (s, 3 H) 4.00 (s, 3 H) 6.24 (d, J=7.9 Hz, 1 H) 6.54-6.63 (m, 2 H) 6.73 (td, J=8.5, 2.4 Hz, 1 H) 6.87-6.98 (m, 3 H) 7.04 (d, J=7.9 Hz, 1 H) 7.35 (dd, J=8.5, 6.9 Hz, 1 H) 7.66 (dd, J=9.6, 2.4 Hz, 1 H) 8.46 (s, 1 H) 12.24 (br. s., 1 H)
LC/MS (method LC-C): R$_t$ 3.07 min, MH$^+$ 515
[α]$_D^{20}$: −105.3° (c 0.264, DMF)
Chiral SFC (method SFC-B): R$_t$ 4.39 min, MH$^+$ 515, chiral purity 99.67%.
Melting point: 208° C.

Example 9 synthesis of 2-(4-fluoro-2-methoxyphenyl)-1-(5-fluoro-6-methyl-1H-indol-3-yl)-2-((3-methoxy-5-(methylsulfonyl)phenyl)amino)ethanone (Compound 9) and chiral separation into Enantiomers 9A and 9B

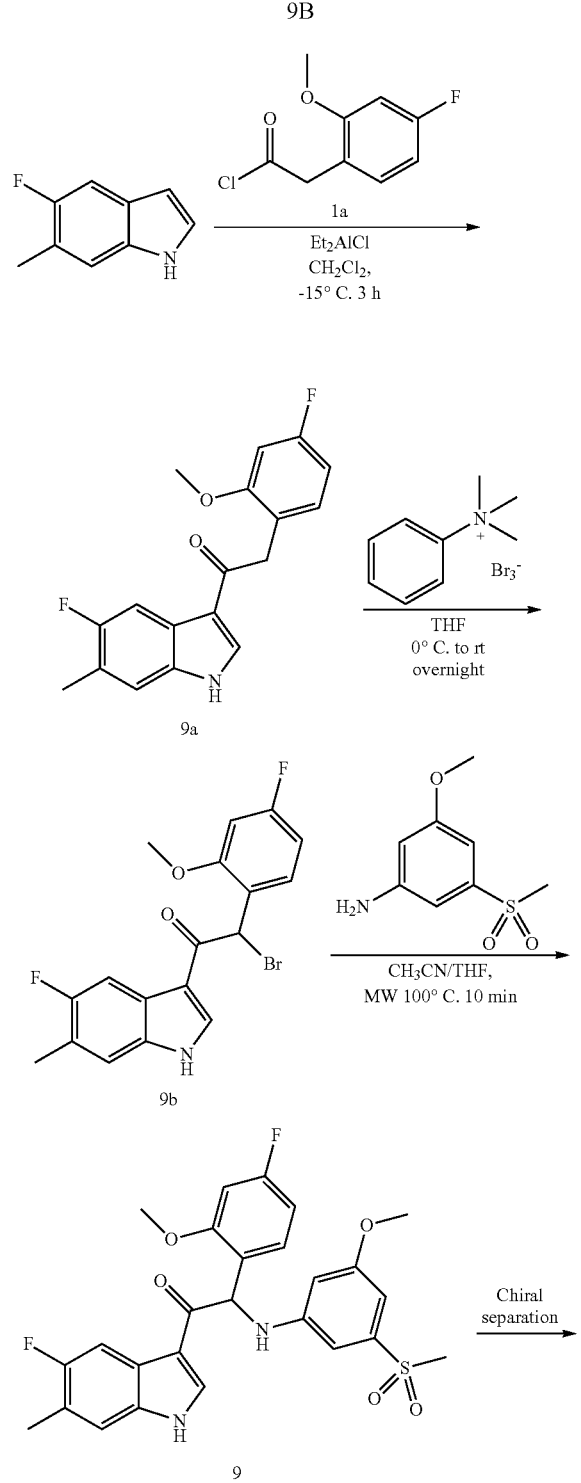

Enantiomers 9A and 9B

Synthesis of Intermediate 9a

A solution of diethylaluminum chloride 1M in hexane (13.5 mL, 13.5 mmol) was added dropwise at −15° C. to a solution of 5-fluoro-6-methyl-1H-indole [CAS 1000343-16-7] (1.0 g, 6.97 mmol) in $CH_2Cl_2$ (30 mL). After 30 min at −15° C., a solution of 2-(4-fluoro-2-methoxyphenyl)acetyl chloride (2.0 g, 10.0 mmol, synthesis: see example 1) in $CH_2Cl_2$ (20 mL) was slowly added. The reaction was stirred at −15° C. for 3 h. 1N Rochelle salt solution (50 mL) was added and the reaction mixture was vigorously stirred at room temperature for 1.5 h. The precipitate was filtered off and partitioned between in EtOAc and 1N HCl. The organic phase was washed with 1N HCl and brine, dried over $MgSO_4$, filtered and concentrated under reduced pressure to give 2-(4-fluoro-2-methoxyphenyl)-1-(5-fluoro-6-methyl-1H-indol-3-yl)ethanone 9a (1.2 g).

Synthesis of Intermediate 9b

A solution of phenyltrimethylammonium tribromide [CAS 4207-56-1] (1.8 g, 4.81 mmol) in THF (50 mL) was added dropwise at 0° C. to a solution 2-(4-fluoro-2-methoxyphenyl)-1-(5-fluoro-6-methyl-1H-indol-3-yl)ethanone 9a (1.2 g, 3.78 mmol) in THF (40 mL). The mixture was stirred at 0° C. for 15 min and at room temperature overnight. The precipitate was filtered off and washed with EtOAc. The filtrate was concentrated under reduced pressure. The residue was taken up with a minimum of EtOAc. The precipitate was filtered off to give 2-bromo-2-(4-fluoro-2-methoxyphenyl)-1-(5-fluoro-6-methyl-1H-indol-3-yl)ethanone 9b (1.2 g).

Synthesis of Compound 9 and chiral separation of Enantiomers 9A and 9B

A mixture of 2-bromo-2-(4-fluoro-2-methoxyphenyl)-1-(5-fluoro-6-methyl-1H-indol-3-yl)ethanone 9b (0.204 g, 0.517 mmol) and 3-methoxy-5-(methylsulfonyl)aniline [CAS 62606-02-4] (0.309 g, 1.54 mmol) in acetonitrile (1 mL) and THF (1 mL) was irradiated in a microwave oven at 100° C. for 10 min. The reaction mixture was diluted with EtOAc and washed with 1N HCl. The organic phase was washed with an aqueous saturated $NaHCO_3$ solution and brine, dried over $MgSO_4$, filtered and concentrated under reduced pressure. The residue was crystallized from EtOAc to afford 2-(4-fluoro-2-methoxyphenyl)-1-(5-fluoro-6-methyl-1H-indol-3-yl)-2-((3-methoxy-5-(methylsulfonyl)phenyl)amino)ethanone (Compound 9, 162 mg) as a racemic mixture.

Chiral separation of the enantiomers of Compound 9 (462 mg) was performed via Preparative Chiral SFC (Stationary phase: Chiralpak AD-H 5 µm 250×30 mm, Mobile phase: 60% $CO_2$, 40% MeOH) yielding 160 mg of the first eluted enantiomer and 170 mg of the second eluted enantiomer. The first eluted enantiomer was purified again by flash chromatography on silica gel (15-40 µm, 4 g, $CH_2Cl_2$/MeOH 99/1). The pure fractions were collected and evaporated to dryness. The residue (120 mg) was solidified from $Et_2O$ and a few drops of $CH_3CN$ to afford Enantiomer 9A (83 mg) as a white powder. The second eluted enantiomer was purified again by flash chromatography on silica gel (15-40 µm, 4 g, $CH_2Cl_2$/EtOAc 98/2). The pure fractions were collected and evaporated to dryness. The residue (110 mg) was solidified from $Et_2O$ and a few drops of $CH_3CN$ to afford Enantiomer 9B (68 mg) as a white powder.

Compound 9:
$^1$H NMR (300 MHz, DMSO-$d_6$) δ ppm 2.31 (d, J=1.4 Hz, 3 H) 3.08 (s, 3 H) 3.72 (s, 3 H) 3.99 (s, 3 H) 6.20 (d, J=7.7 Hz, 1 H) 6.56-6.61 (m, 2 H) 6.73 (td, J=8.5, 2.4 Hz, 1 H) 6.90 (m, 1 H) 6.95 (dd, J=11.6, 2.4 Hz, 1 H) 7.03 (d, J=7.7 Hz, 1 H) 7.28-7.42 (m, 2 H) 7.77 (d, J=10.6 Hz, 1 H) 8.39 (s, 1 H) 12.02 (s, 1 H)

LC-MS (method LC-E): $R_t$ 8.6 min, MH$^+$ 515

Enantiomer 9A:
$^1$H NMR (500 MHz, DMSO-$d_6$) δ ppm 2.29-2.32 (m, 3 H) 3.08 (s, 3 H) 3.71 (s, 3 H) 3.99 (s, 3 H) 6.20 (d, J=7.9 Hz, 1 H) 6.53-6.61 (m, 2 H) 6.73 (td, J=8.4, 2.5 Hz, 1 H) 6.90 (s, 1 H) 6.95 (dd, J=11.4, 2.5 Hz, 1 H) 7.04 (d, J=7.9 Hz, 1 H) 7.28-7.42 (m, 2 H) 7.77 (d, J=10.4 Hz, 1 H) 8.40 (s, 1 H) 12.05 (br. s., 1 H)

LC/MS (method LC-C): $R_t$ 3.05 min, MH$^+$ 515

$[\alpha]_D^{20}$: +125.5° (c 0.3945, DMF)

Chiral SFC (method SFC-D): $R_t$ 2.54 min, MH$^+$ 515, chiral purity 99.05%.

Melting point: 206° C.

Enantiomer 9B:
$^1$H NMR (500 MHz, DMSO-$d_6$) δ ppm 2.26-2.33 (m, 3 H) 3.08 (s, 3 H) 3.71 (s, 3 H) 3.99 (s, 3 H) 6.20 (d, J=7.6 Hz, 1 H) 6.53-6.60 (m, 2 H) 6.73 (td, J=8.5, 2.5 Hz, 1 H) 6.90 (s, 1 H) 6.95 (dd, J=11.4, 2.5 Hz, 1 H) 7.04 (d, J=7.6 Hz, 1 H) 7.27-7.41 (m, 2 H) 7.77 (d, J=10.7 Hz, 1 H) 8.40 (s, 1 H) 12.05 (br. s., 1 H)

LC/MS (method LC-C): $R_t$ 3.05 min, MH$^+$ 515

$[\alpha]_D^{20}$: −129.5° (c 0.3955, DMF)

Chiral SFC (method SFC-D): $R_t$ 2.98 min, MH$^+$ 515, chiral purity 99.18%.

Melting point: 206° C.

Example 10

2-(4-fluoro-2-methoxyphenyl)-2-((3-methoxy-5-(methylsulfonyl)-phenyl)amino)-1-(6-methoxy-5-methyl-1H-indol-3-yl)ethanone (Compound 10) and chiral separation into Enantiomers 10A and 10B

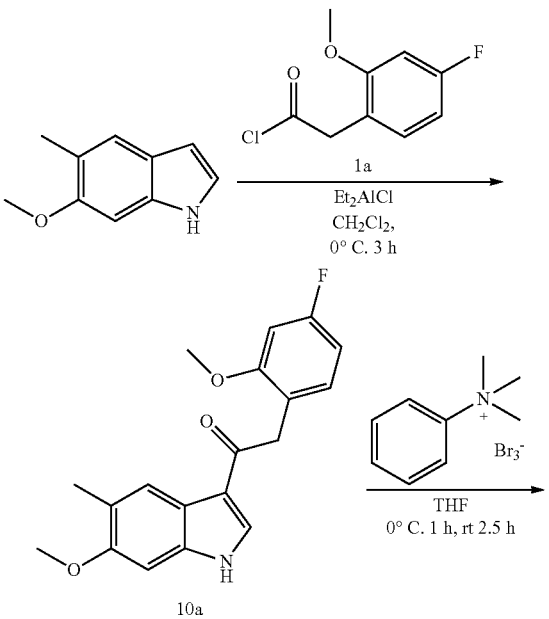

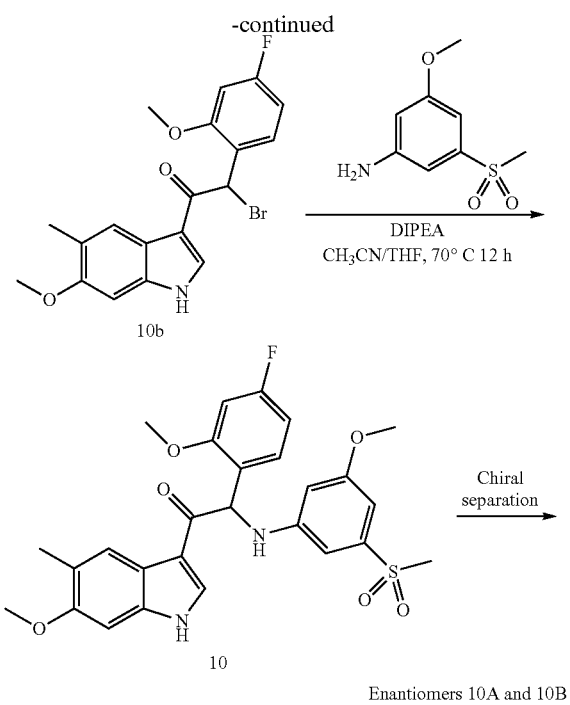

Synthesis of Intermediate 10a

Diethylaluminum chloride 1M in hexane (18.6 mL, 18.6 mmol) was added dropwise at 0° C. to a solution of 6-methoxy-5-methyl-1H-indole [CAS 1071973-95-9] (2 g, 12.4 mmol) in $CH_2Cl_2$ (60 mL). After 30 min at 0° C., 2-(4-fluoro-2-methoxyphenyl)acetyl chloride 1a (3.3 g, 16.3 mmol, synthesis: see Example 1) in $CH_2Cl_2$ (60 mL) was added slowly at 0° C. The reaction was stirred at 0° C. for 3 h. Ice-water was added and the precipitate was filtered off, washed with water, and dried under vacuum to provide 2-(4-fluoro-2-methoxyphenyl)-1-(6-methoxy-5-methyl-1H-indol-3-yl)ethanone 10a (3.15 g).

Synthesis of Intermediate 10b

At 0° C., a solution of phenyltrimethylammonium tribromide [CAS 4207-56-1] (3.8 g, 10.1 mmol) in THF (90 mL) was added dropwise to a mixture of 2-(4-fluoro-2-methoxyphenyl)-1-(6-methoxy-5-methyl-1H-indol-3-yl)ethanone 10a (3.15 g, 9.6 mmol) in THF (90 mL). The mixture was stirred at 0° C. for 1 h and at room temperature for 2.5 h. The precipitate was filtered off and washed with EtOAc. The filtrate was concentrated under reduced pressure. The resulting residue was taken up with a minimum amount of $CH_3CN$ and diisopropylether. The precipitate was filtered off and dried under vacuum to provide 2-bromo-2-(4-fluoro-2-methoxy-phenyl)-1-(6-methoxy-5-methyl-1H-indol-3-yl)ethanone 10b (2.8 g).

Synthesis of Compound 10 and chiral separation of Enantiomers 10A and 10B

A mixture of 2-bromo-2-(4-fluoro-2-methoxyphenyl)-1-(6-methoxy-5-methyl-1H-indol-3-yl)ethanone 10b (1.0 g, 2.46 mmol), 3-methoxy-5-(methylsulfonyl)aniline [CAS 62606-02-4] (743 mg, 3.69 mmol) and diisopropylethylamine (0.64 mL, 3.69 mmol) in $CH_3CN$ (15 mL) and THF (15 mL) was heated at 70° C. for 12 h. The solvents were removed under reduced pressure. The residue was dissolved in EtOAc. The organic layer was washed twice with 1 N HCl, washed with water, dried over $MgSO_4$, filtered and the solvent was concentrated under reduced pressure. Purification was carried out by flash chromatography on silica gel (15-40 µm, 40 g, $CH_2Cl_2$/$CH_3OH$ 99.8/0.2). The pure fractions were collected and evaporated to dryness to give 2-(4-fluoro-2-methoxyphenyl)-2-((3-methoxy-5-(methylsulfonyl)phenyl)amino)-1-(6-methoxy-5-methyl-1H-indol-3-yl)ethanone (Compound 10, 638 mg) as a racemic mixture.

Chiral separation of the enantiomers of Compound 10 was performed via Preparative Chiral SFC (Stationary phase: Chiralpak® AD-H 5 µm 250×30 mm, Mobile phase: 70% $CO_2$, 30% iPrOH) yielding 244 mg of the first eluted enantiomer and 163 mg of the second eluted enantiomer. The first eluted enantiomer was purified again by flash chromatography on silica gel (15-40 µm, 40 g, $CH_2Cl_2$/EtOAc 98/2). The pure fractions were collected and evaporated to dryness. The residue (161 mg) was solidified from $Et_2O$ and a few drops of $CH_3CN$ to afford Enantiomer 10A (136 mg). The second eluted enantiomer was purified again by flash chromatography on silica gel (15-40 µm, 40 g, $CH_2Cl_2$/EtOAc 98/2). The pure fractions were collected and evaporated to dryness. The residue (158 mg) was solidified from $Et_2O$ and a few drops of $CH_3CN$ to afford Enantiomer 10B (135 mg).

Compound 10:
$^1$H NMR (500 MHz, DMSO-$d_6$) δ ppm 2.21 (s, 3 H) 3.08 (s, 3 H) 3.72 (s, 3 H) 3.79 (s, 3 H) 4.00 (s, 3 H) 6.18 (d, J=7.6 Hz, 1 H) 6.55-6.60 (m, 2 H) 6.72 (td, J=8.5, 2.5 Hz, 1 H) 6.89-7.00 (m, 4 H) 7.35 (dd, J=8.5, 7.1 Hz, 1 H) 7.90 (s, 1 H) 8.23 (s, 1 H) 11.75 (br. s., 1 H)

LC/MS (method LC-C): $R_t$ 3.04 min, MH$^+$ 527

Melting point: 224° C.

Enantiomer 10A:
$^1$H NMR (500 MHz, DMSO-d6) δ ppm 2.21 (s, 3 H) 3.08 (s, 3 H) 3.71 (s, 3 H) 3.79 (s, 3 H) 4.00 (s, 3 H) 6.18 (d, J=7.6 Hz, 1 H) 6.53-6.60 (m, 2 H) 6.72 (td, J=8.5, 2.5 Hz, 1 H) 6.87-7.02 (m, 4 H) 7.35 (dd, J=8.5, 7.1 Hz, 1 H) 7.90 (s, 1 H) 8.24 (d, J=2.8 Hz, 1 H) 11.76 (br. s., 1 H)

LC/MS (method LC-C): $R_t$ 3.03 min, MH$^+$ 527

$[\alpha]_D^{20}$: −121.5° (c 0.284, DMF)

Chiral SFC (method SFC-F): $R_t$ 2.35 min, MH$^+$ 527, chiral purity 100%

Melting point: 242° C.

Enantiomer 10B:
$^1$H NMR (500 MHz, DMSO-$d_6$) δ ppm 2.21 (s, 3 H) 3.08 (s, 3 H) 3.71 (s, 3 H) 3.79 (s, 3 H) 4.00 (s, 3 H) 6.18 (d, J=7.9 Hz, 1 H) 6.54-6.60 (m, 2 H) 6.72 (td, J=8.5, 2.2 Hz, 1 H) 6.87-7.02 (m, 4 H) 7.35 (dd, J=8.5, 6.9 Hz, 1 H) 7.90 (s, 1 H) 8.24 (s, 1 H) 11.76 (br. s., 1 H)

LC/MS (method LC-C): $R_t$ 3.03 min, MH$^+$ 527

$[\alpha]_D^{20}$: +122.9° (c 0.284, DMF)

Chiral SFC (method SFC-F): $R_t$ 3.33 min, MH$^+$ 527, chiral purity 99.1%.

Melting point: 242° C.

Example 10.1

Chiral Stability of Enantiomer 10B at pH 7.4

The chiral stability of Enantiomer 10B (R=OMe) was evaluated by determination of the enantiomeric excess (ee %) after incubation for 24 h and 48 h in a buffered solution at pH 7.4 at 40° C. and 60° C. To assess the influence of the methoxy-substituent of Enantiomer 10B (R=OMe) on the stability against racemization, the chiral stability of Enantiomer 10'B (R=H) was tested under the same conditions. To this end, 5 µM buffered (pH=7.4) solutions of 10B and 10'B were prepared by mixing 25 µL of a 100 µM solution of 10B and 10'B in DMSO with 475 µL aqueous buffer pH 7.4. Samples were taken 24 h and 48 h after incubation at 40° C. and 60° C. The analytical samples were analyzed by Chiral SFC (MS detection) and the chiral purity was expressed as the enantiomeric excess (ee %=% enantiomer B−% enantiomer A). Both Enantiomers 10B and 10'B had a chiral purity of 100% prior to their incubation.

|  |  | ee % Sampling timepoints (h) | |
| --- | --- | --- | --- |
| Compound | Temperature | 24 | 48 |
| 10B | 40° C. | 100 | 100 |
|  | 60° C. | 97 | 97 |
| 10'B | 40° C. | 96 | 73 |
|  | 60° C. | 22 | 9 |

Example 11

2-(4-fluoro-2-methoxyphenyl)-1-(5-fluoro-6-methoxy-1H-indol-3-yl)-2-((3-methoxy-5-(methylsulfonyl)phenyl)amino ethanone (Compound 11) and chiral separation into Enantiomers 11A and 11B

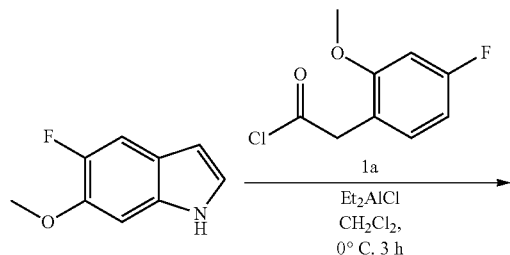

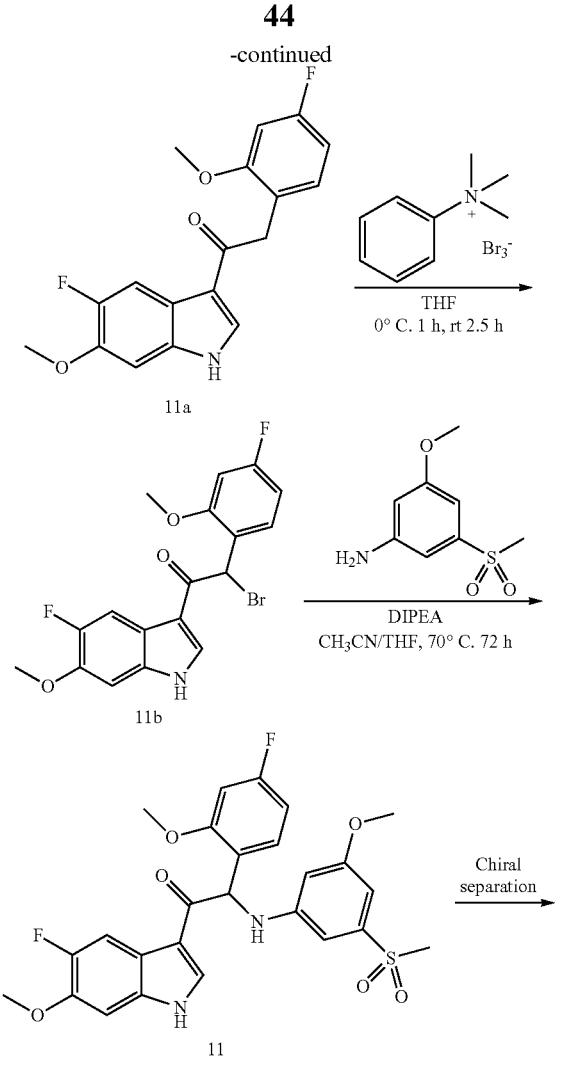

Synthesis of Intermediate 11a

Diethylaluminum chloride 1M in hexane (20 mL, 20 mmol) was added dropwise at 0° C. to a solution of 5-fluoro-6-methoxy-1H-indole [CAS 1211595-72-0] (2.2 g, 13.3 mmol) in CH$_2$Cl$_2$ (60 mL). After 30 min at 0° C., 2-(4-fluoro-2-methoxyphenyl)-acetyl chloride 1a (3.85 g, 19 mmol, synthesis: see Example 1) in CH$_2$CO$_2$ (60 mL) was added slowly at 0° C. The reaction was stirred at 0° C. for 3 h. Ice-water and an aqueous solution of NaHCO$_3$ was added. The reaction mixture was extracted with CH$_2$Cl$_2$/MeOH. The organic layer was washed with water, dried over MgSO$_4$, filtered, and the solvent was concentrated under reduced pressure. The residue was taken up with a minimum of CH$_2$Cl$_2$. The precipitate was filtered off and dried to afford 2-(4-fluoro-2-methoxyphenyl)-1-(5-fluoro-6-methoxy-1H-indol-3-yl)-ethanone 11a (3.2 g).

Synthesis of Intermediate 11b

At 0° C., a solution of phenyltrimethylammonium tribromide [CAS 4207-56-1](3.22 g, 8.56 mmol) in THF (80 mL) was added dropwise to a mixture of 2-(4-fluoro-2-methoxyphenyl)-1-(5-fluoro-6-methoxy-1H-indol-3-yl)ethanone 11a (2.7 g, 8.15 mmol) in THF (80 mL). The mixture was stirred at 0° C. for 1 h and at room temperature for 2.5 h. The precipitate was filtered-off, washed with EtOAc and water and dried to afford a first batch of 2-bromo-2-(4-fluoro-2-methoxy-phenyl)-1-(5-fluoro-6-methoxy-1H-indol-3-yl) ethanone 11 b (1.5 g). The organic layer of the filtrate was separated, dried over MgSO$_4$, filtered and concentrated under reduced pressure. The resulting residue was taken up with a minimum amount of CH$_3$CN and diisopropylether. The precipitate was filtered off and dried under vacuum to give a second batch of 11b (1.7 g).

Synthesis of Compound 11 and Chiral Separation of Enantiomers 11A and 11B

A mixture of 2-bromo-2-(4-fluoro-2-methoxyphenyl)-1-(5-fluoro-6-methoxy-1H-indol-3-yl)ethanone 11 b (0.8 g, 1.95 mmol), 3-methoxy-5-(methylsulfonyl)aniline [CAS 62606-02-4] (589 mg, 2.93 mmol) and diisopropylethylamine (0.51 mL, 2.93 mmol) in CH$_3$CN (15 mL) and THF (15 mL) was heated at 70° C. for 72 h. The solvents were removed under reduced pressure. The residue was dissolved in EtOAc. The organic layer was washed twice with 1 N HCl, washed with water, dried over MgSO$_4$, filtered and the solvent was concentrated under reduced pressure. Purification was carried out by flash chromatography on silica gel (15-40 μm, 40 g, CH$_2$Cl$_2$/CH$_3$OH 99.5/0.5). The pure fractions were collected and evaporated to dryness to give 2-(4-fluoro-2-methoxyphenyl)-1-(5-fluoro-6-methoxy-1H-indol-3-yl)-2-((3-methoxy-5-(methylsulfonyl)phenyl) amino)ethanone (Compound 11, 450 mg) as a racemic mixture.

Chiral separation of the enantiomers of Compound 11 (380 mg) was performed via Preparative Chiral SFC (Stationary phase: Chiralpak® IC 5 μm 250×20 mm, Mobile phase: 70% CO$_2$, 30% MeOH) yielding after crystallization from CH$_3$CN/diisopropylether, 174 mg of the first eluted enantiomer (Enantiomer 11A) and 165 mg of the second eluted enantiomer (Enantiomer 11B).

Compound 11:
$^1$H NMR (500 MHz, DMSO-d$_6$) δ ppm 3.08 (s, 3 H) 3.72 (s, 3 H) 3.85 (s, 3 H) 3.99 (s, 3 H) 6.20 (d, J=7.6 Hz, 1 H) 6.58 (s, 2 H) 6.73 (td, J=8.4, 2.5 Hz, 1 H) 6.87-6.92 (m, 1 H) 6.96 (dd, J=11.3, 2.5 Hz, 1 H) 7.03 (d, J=7.6 Hz, 1 H) 7.15 (d, J=7.3 Hz, 1 H) 7.36 (dd, J=8.4, 6.9 Hz, 1 H) 7.83 (d, J=12.0 Hz, 1 H) 8.34 (s, 1 H) 11.95 (br. s., 1 H)

LC/MS (method LC-C): R$_t$ 2.89 min, MH$^+$ 531

Melting point: 172° C.

Enantiomer 11A:
$^1$H NMR (500 MHz, DMSO-d$_6$) δ ppm 3.08 (s, 3 H) 3.71 (s, 3 H) 3.85 (s, 3 H) 3.99 (s, 3 H) 6.19 (d, J=7.6 Hz, 1 H) 6.53-6.61 (m, 2 H) 6.73 (td, J=8.4, 2.5 Hz, 1 H) 6.90 (s, 1 H) 6.96 (dd, J=11.3, 2.5 Hz, 1 H) 7.04 (d, J=7.6 Hz, 1 H) 7.15 (d, J=7.3 Hz, 1 H) 7.35 (dd, J=8.4, 6.8 Hz, 1 H) 7.82 (d, J=12.0 Hz, 1 H) 8.34 (s, 1 H) 11.96 (br. s., 1 H)

LC/MS (method LC-C): R$_t$ 2.89 min, MH$^+$ 531

[α]$_D^{20}$: +104.9° (c 0.264, DMF)

Chiral SFC (method SFC-E): R$_t$ 2.92 min, MH$^+$ 531, chiral purity 100%.

Melting point: 247° C.

Enantiomer 11B:
$^1$H NMR (500 MHz, DMSO-d$_6$) δ ppm 3.08 (s, 3 H) 3.71 (s, 3 H) 3.85 (s, 3 H) 3.99 (s, 3 H) 6.20 (d, J=7.6 Hz, 1 H) 6.53-6.61 (m, 2 H) 6.73 (td, J=8.4, 2.5 Hz, 1 H) 6.90 (s, 1 H) 6.96 (dd, J=11.3, 2.5 Hz, 1 H) 7.04 (d, J=7.6 Hz, 1 H) 7.15 (d, J=7.3 Hz, 1 H) 7.35 (dd, J=8.4, 6.9 Hz, 1 H) 7.82 (d, J=11.7 Hz, 1 H) 8.34 (s, 1 H) 11.95 (br. s., 1 H)

LC/MS (method LC-C): R$_t$ 2.89 min, MH$^+$ 531

[α]$_D^{20}$: −105.7° (c 0.279, DMF)

Chiral SFC (method SFC-E): R$_t$ 3.92 min, MH$^+$ 531, chiral purity 99.37%.

Melting point: 245° C.

Example 12

1-(7-chloro-6-methoxy-1H-indol-3-yl)-2-(4-fluoro-2-methoxyphenyl)-2-((3-methoxy-5-(methylsulfonyl)phenyl)amino)ethanone (Compound 12) and chiral separation into Enantiomers 12A and 12B

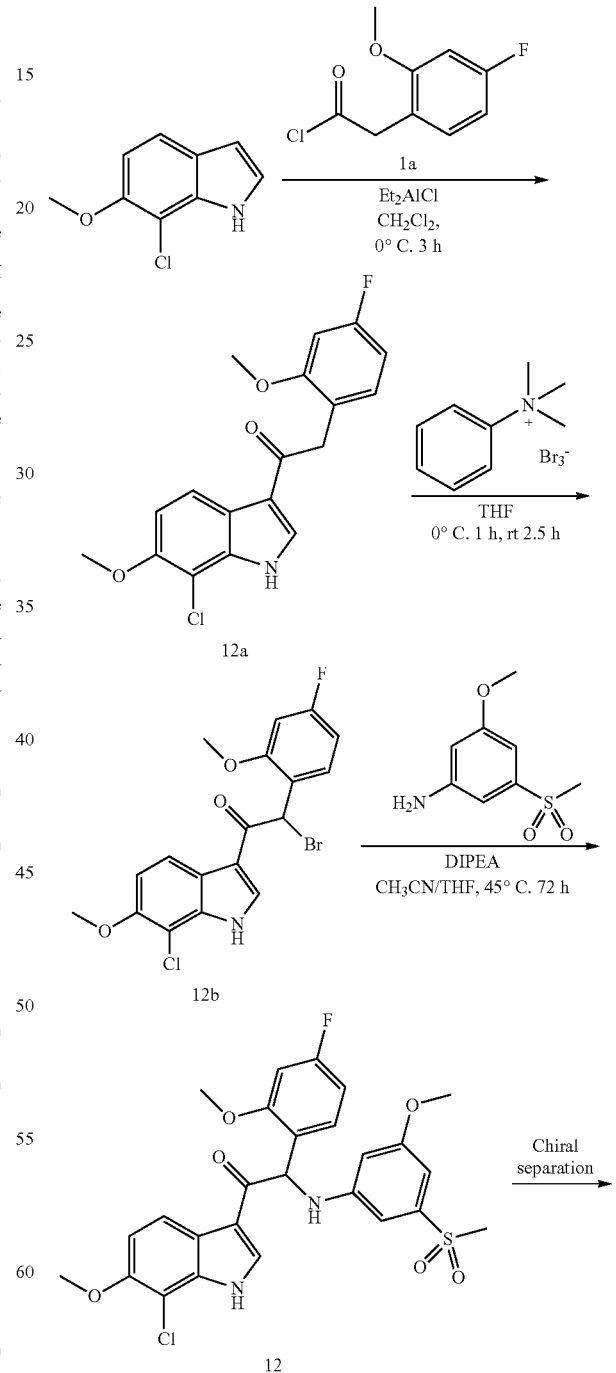

Enantiomers 12A and 12B

Synthesis of Intermediate 12a

Diethylaluminum chloride 1M in hexane (16.5 mL, 16.5 mmol) was added dropwise at 0° C. to a solution of 7-chloro-6-methoxy-1H-indole [CAS 1227604-21-8] (2 g, 11 mmol) in $CH_2Cl_2$ (60 mL). After 30 min at 0° C., 2-(4-fluoro-2-methoxy-phenyl)acetyl chloride 1a (3.3 g, 16.3 mmol, synthesis: see Example 1) in $CH_2Cl_2$ (60 mL) was added slowly at 0° C. The reaction was stirred at 0° C. for 3 h. Ice-water was added and the precipitate was filtered off, washed with water, and dried under vacuum to give 1-(7-chloro-6-methoxy-1H-indol-3-yl)-2-(4-fluoro-2-methoxy-phenyl)ethanone 12a (2.7 g).

Synthesis of Intermediate 12b

At 0° C., a solution of phenyltrimethylammonium tribromide [CAS 4207-56-1](3.06 g, 8.15 mmol) in THF (80 mL) was added dropwise to a mixture of 1-(7-chloro-6-methoxy-1H-indol-3-yl)-2-(4-fluoro-2-methoxyphenyl)ethanone 12a (2.7 g, 7.76 mmol) in THF (80 mL). The mixture was stirred at 0° C. for 1 h and at room temperature for 2.5 h. The precipitate was filtered off and washed with EtOAc. The filtrate was concentrated under reduced pressure, solubilized in EtOAc and washed with water. The organic layer was separated, dried over $MgSO_4$, filtered and concentrated under reduced pressure. The resulting residue was taken up with a minimum amount of $CH_3CN$ and diisopropylether. The precipitate was filtered off and dried under vacuum to give 2-bromo-1-(7-chloro-6-methoxy-1H-indol-3-yl)-2-(4-fluoro-2-methoxyphenyl)ethanone 12b (3.2 g).

Synthesis of Compound 12 and Chiral Separation of Enantiomers 12A and 12B

A mixture of 2-bromo-1-(7-chloro-6-methoxy-1H-indol-3-yl)-2-(4-fluoro-2-methoxy-phenyl)ethanone 12b (0.9 g, 2.11 mmol), 3-methoxy-5-(methylsulfonyl)aniline [CAS 62606-02-4] (637 mg, 3.16 mmol) and diisopropylethylamine (0.55 mL, 3.16 mmol) in $CH_3CN$ (20 mL) and THF (20 mL) was heated at 45° C. for 72 h. The solvents were removed under reduced pressure. The residue was dissolved in EtOAc. The organic layer was washed twice with 1 N HCl, washed with water, dried over $MgSO_4$, filtered and the solvent was concentrated under reduced pressure. Purification was carried out by flash chromatography on silica gel (15-40 μm, 80 g, $CH_2Cl_2/CH_3OH$ 99.5/0.5). The pure fractions were collected and evaporated to dryness to give 1-(7-chloro-6-methoxy-1H-indol-3-yl)-2-(4-fluoro-2-methoxyphenyl)-2-((3-methoxy-5-(methylsulfonyl)phenyl)amino)ethanone (Compound 12, 820 mg) as a racemic mixture.

Chiral separation of the enantiomers of Compound 12 (750 mg) was performed via Preparative Chiral SFC (Stationary phase: Chiralcel® OD-H 5 μm 250×30 mm, Mobile phase: 60% $CO_2$, 40% MeOH) yielding after solidification in diisopropylether, 285 mg of the first eluted enantiomer (Enantiomer 12A) and 260 mg of the second eluted enantiomer (Enantiomer 12B) as amorphous powders.

Compound 12:
$^1$H NMR (500 MHz, DMSO-$d_6$) δ ppm 3.09 (s, 3 H) 3.72 (s, 3 H) 3.87 (s, 3 H) 3.99 (s, 3 H) 6.24 (d, J=7.6 Hz, 1 H) 6.51-6.64 (m, 2 H) 6.73 (td, J=8.4, 2.2 Hz, 1 H) 6.92 (s, 1 H) 6.96 (dd, J=11.4, 2.2 Hz, 1 H) 7.03 (d, J=7.6 Hz, 1 H) 7.11 (d, J=8.8 Hz, 1 H) 7.32-7.41 (m, 1 H) 8.05 (d, J=8.8 Hz, 1 H) 8.36 (s, 1 H) 12.20 (s, 1 H)

LC/MS (method LC-C): $R_t$ 3.02 min, MH$^+$ 547

Enantiomer 12A:
$^1$H NMR (500 MHz, DMSO-$d_6$) δ ppm 3.09 (s, 3 H) 3.72 (s, 3 H) 3.87 (s, 3 H) 3.99 (s, 3 H) 6.24 (d, J=7.6 Hz, 1 H) 6.53-6.64 (m, 2 H) 6.73 (td, J=8.4, 2.2 Hz, 1 H) 6.92 (s, 1 H) 6.96 (dd, J=11.4, 2.2 Hz, 1 H) 7.03 (d, J=7.6 Hz, 1 H) 7.11 (d, J=8.8 Hz, 1 H) 7.36 (dd, J=8.4, 7.6 Hz, 1 H) 8.05 (d, J=8.8 Hz, 1 H) 8.36 (s, 1 H) 12.20 (br. s., 1 H)

LC/MS (method LC-C): $R_t$ 3.01 min, MH$^+$ 547

$[α]_D^{20}$: +89.7° (c 0.262, DMF)

Chiral SFC (method SFC-C): $R_t$ 2.79 min, MH$^+$ 547, chiral purity 98.98%.

Enantiomer 12B:
$^1$H NMR (500 MHz, DMSO-$d_6$) δ ppm 3.09 (s, 3 H) 3.72 (s, 3 H) 3.87 (s, 3 H) 3.99 (s, 3 H) 6.24 (d, J=7.6 Hz, 1 H) 6.54-6.62 (m, 2 H) 6.73 (td, J=8.5, 2.2 Hz, 1 H) 6.92 (s, 1 H) 6.96 (dd, J=11.2, 2.2 Hz, 1 H) 7.03 (d, J=7.6 Hz, 1 H) 7.11 (d, J=8.8 Hz, 1 H) 7.36 (dd, J=8.5, 7.6 Hz, 1 H) 8.05 (d, J=8.8 Hz, 1 H) 8.36 (s, 1 H) 12.20 (br. s., 1 H)

LC/MS (method LC-C): $R_t$ 3.01 min, MH$^+$ 547

$[α]_D^{20}$: −93.2° (c 0.236, DMF)

Chiral SFC (method SFC-C): $R_t$ 3.76 min, MH$^+$ 547, chiral purity 99.66%.

Example 13 synthesis of 1-(6,7-difluoro-1H-indol-3-yl)-2-(4-fluoro-2-methoxy-phenyl)-2-((3-methoxy-5-(methylsulfonyl)phenyl)amino)ethanone (Compound 13) and chiral separation into Enantiomers 13A and 13B

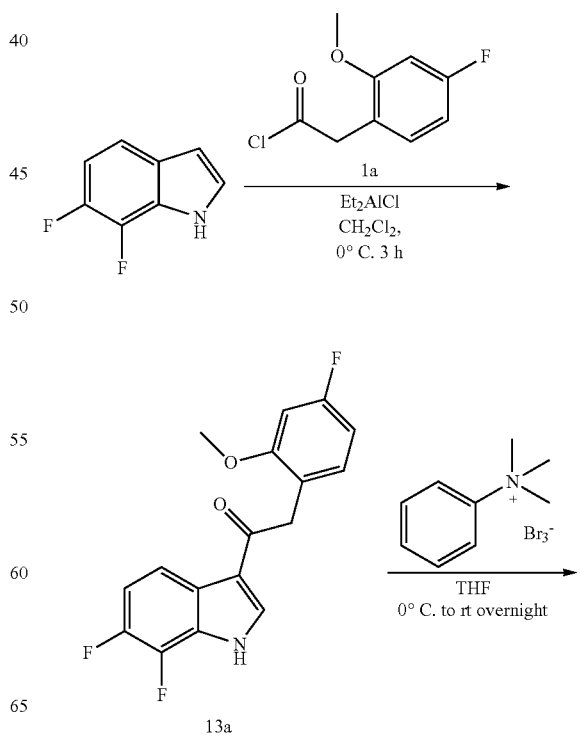

49

-continued

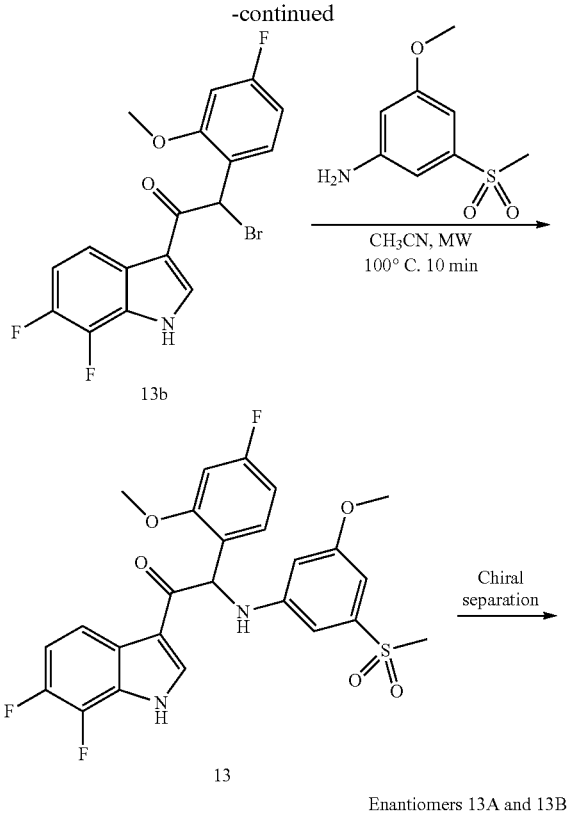

Synthesis of Intermediate 13a

A solution of diethylaluminum chloride 1M in hexane (20 mL, 20 mmol) was added dropwise at 0° C. to a solution of 6,7-difluoro-1H-indole [CAS 271780-84-8] (1.5 g, 10.1 mmol) in $CH_2Cl_2$ (45 mL). After 30 min at 0° C., a solution of 2-(4-fluoro-2-methoxyphenyl)acetyl chloride 1a (3.1 g, 15.04 mmol, synthesis: see Example 1) in $CH_2Cl_2$ (30 mL) was slowly added. The reaction was stirred at 0° C. for 3 h. 1N Rochelle salt solution (50 mL) was added and the reaction mixture was vigorously stirred at room temperature for 1 h. The precipitate was filtered off and partitioned between in EtOAc and 1 N HCl. The aqueous phase was extracted with EtOAc. The organic phases were combined, washed with brine, dried over $MgSO_4$, filtered and concentrated under reduced pressure to give 1-(6,7-difluoro-1H-indol-3-yl)-2-(4-fluoro-2-methoxyphenyl)ethanone 13a (1.6 g).

Synthesis of Intermediate 13b

A solution of phenyltrimethylammonium tribromide [CAS 4207-56-1] (2.3 g, 6.06 mmol) in THF (45 mL) was added dropwise at 0° C. to a solution of 1-(6,7-difluoro-1H-indol-3-yl)-2-(4-fluoro-2-methoxyphenyl)ethanone 13a (1.8 g, 5.57 mmol) in THF (55 mL). The mixture was stirred at 0° C. for 15 min and at room temperature overnight. The precipitate was filtered off and washed with EtOAc. The filtrate was concentrated under reduced pressure. The residue was taken up with a minimum of acetonitrile. The precipitate was filtered off to give 2-bromo-1-(6,7-difluoro-1H-indol-3-yl)-2-(4-fluoro-2-methoxyphenyl)ethanone 13b (2.0 g).

50

Synthesis of Compound 13 and chiral separation of Enantiomers 13A and 13B

A mixture of 2-bromo-1-(6,7-difluoro-1H-indol-3-yl)-2-(4-fluoro-2-methoxyphenyl)-ethanone 13b (1.3 g, 3.29 mmol) and 3-methoxy-5-(methylsulfonyl)aniline [CAS 62606-02-4] (2.0 g, 9.91 mmol) in acetonitrile (13 mL) was irradiated in a microwave oven at 100° C. for 10 min. The reaction mixture was diluted with EtOAc, washed with 1 N HCl and brine, dried over $MgSO_4$, filtered and concentrated under reduced pressure. The residue was triturated with acetonitrile, ethyl acetate and diethyl ether to afford 1-(6,7-difluoro-1H-indol-3-yl)-2-(4-fluoro-2-methoxyphenyl)-2-((3-methoxy-5-(methylsulfonyl)phenyl)amino)ethanone (Compound 13, 750 mg) as a racemic mixture.

Chiral separation of the enantiomers of Compound 13 (1.27 g) was performed via Preparative Chiral SFC (Stationary phase: Chiralpak® IC 5 μm 250×30 mm, Mobile phase: 70% $CO_2$, 30% MeOH) yielding after crystallization from $CH_2Cl_2$/diisopropylether, 409 mg of the first eluted enantiomer (Enantiomer 13A) and 385 mg of the second eluted enantiomer (Enantiomer 13B).

Compound 13:

$^1$H NMR (300 MHz, DMSO-$d_6$) δ ppm 3.09 (s, 3 H) 3.72 (s, 3 H) 3.98 (s, 3 H) 6.27 (d, J=7.9 Hz, 1 H) 6.56-6.63 (m, 2 H) 6.74 (td, J=8.4, 2.4 Hz, 1 H) 6.92 (s, 1 H) 6.96 (dd, J=11.3, 2.4 Hz, 1 H) 7.06 (d, J=7.9 Hz, 1 H) 7.25 (m, 1 H) 7.36 (dd, J=8.6, 6.9 Hz, 1 H) 7.93 (dd, J=8.8, 4.4 Hz, 1 H) 8.51 (d, J=2.8 Hz, 1 H) 12.8 (br. s., 1 H)

LC-MS (method LC-F) $R_t$ 1.41 min, MH$^+$ 519

Enantiomer 13A:

$^1$H NMR (500 MHz, DMSO-$d_6$) δ ppm 12.80 (br. s, 1 H) 8.50 (s., 1 H) 7.93 (m, 1 H) 7.37 (t, J=7.3 Hz, 1 H) 7.16-7.29 (m, 1 H) 7.06 (d, J=7.3 Hz, 1 H) 6.86-6.99 (m, 2 H) 6.74 (t, J=7.3 Hz, 1 H) 6.60 (m, 2 H) 6.26 (d, J=7.3 Hz, 1 H) 3.98 (s., 3 H) 3.73 (s., 3 H) 3.10 (s., 3 H)

LC/MS (method LC-C): $R_t$ 3.05 min, MH$^+$ 519

$[\alpha]_D^{20}$: −47.8° (c 0.2827, DMF)

Chiral SFC (method SFC-A): $R_t$ 2.52 min, MH$^+$ 519, chiral purity 100%.

Melting point: 226° C.

Enantiomer 13B:

$^1$H NMR (500 MHz, DMSO-$d_6$) δ ppm 12.78 (br. s, 1 H) 8.49 (s, 1 H) 7.92 (dd, J=8.7, 4.3 Hz, 1 H) 7.36 (t, J=7.7 Hz, 1 H) 7.16-7.28 (m, 1 H) 7.04 (d, J=7.9 Hz, 1 H) 6.86-6.99 (m, 2 H) 6.74 (td, J=8.5, 1.9 Hz, 1 H) 6.54-6.65 (m, 2 H) 6.26 (d, J=7.9 Hz, 1 H) 3.98 (s, 3 H) 3.72 (s, 3 H) 3.09 (s, 3 H)

LC/MS (method LC-C): $R_t$ 3.05 min, MH$^+$ 519

$[\alpha]_D^{20}$: +48.2° (c 0.3009, DMF)

Chiral SFC (method SFC-A): $R_t$ 3.04 min, MH$^+$ 519, chiral purity 99.57%.

Melting point: 222° C.

Example 14 synthesis 2-(4-fluoro-2-methoxyphenyl)-1-(6-fluoro-5-methyl-1H-indol-3-yl)-2-((3-methoxy-5-(methylsulfonyl)phenyl)amino)ethanone (Compound 14) and chiral separation into Enantiomers 14A and 14B

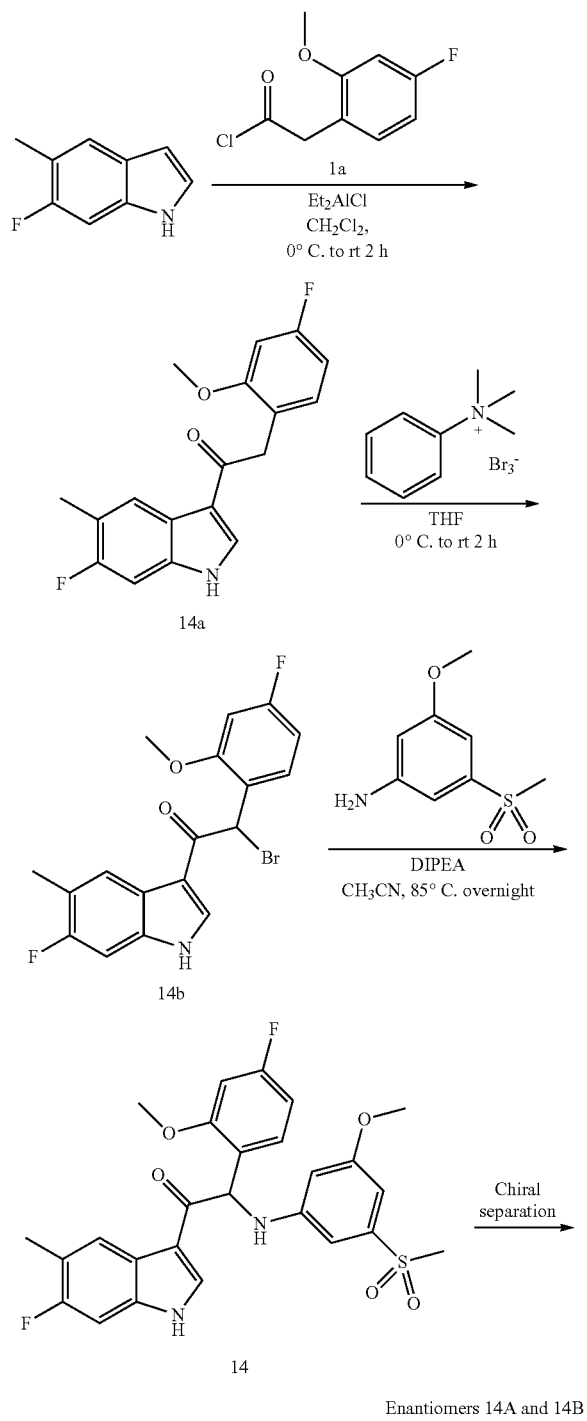

Synthesis of Intermediate 14a

A solution of 6-fluoro-5-methyl-1H-indole [CAS 162100-95-0] (880 mg, 5.9 mmol) in CH$_2$Cl$_2$ (50 mL) was cooled to 0° C. under N$_2$-atmosphere. A solution of diethylaluminum chloride 1M in hexane (8.85 mL, 8.85 mmol) was added dropwise and the resulting mixture was kept at 0° C. for 15 min. A solution of 2-(4-fluoro-2-methoxyphenyl)acetyl chloride 1a (1.67 g, 8.26 mmol) in CH$_2$Cl$_2$ (25 mL) was added dropwise. Stirring was continued at 0° C. for 1 h and the reaction mixture was subsequently stirred at room temperature for 2 h. The reaction mixture was poured out in a stirring ice/Rochelle salt solution. The mixture was filtered over Dicalite® and the filter cake was washed several times with THF. The filtrates were combined. The layers were separated and the organic layer was washed with brine and water, dried over MgSO$_4$, filtered and evaporated under reduced pressure. The solid residue was suspended in CH$_2$Cl$_2$ (30 mL). The precipitate was filtered off, washed with a small amount of CH$_2$Cl$_2$ and dried under vacuum at 50° C. to provide 2-(4-fluoro-2-methoxyphenyl)-1-(6-fluoro-5-methyl-1H-indol-3-yl)ethanone 14a (1.22 g).

Synthesis of Intermediate 14b stirred solution of 2-(4-fluoro-2-methoxyphenyl)-1-(6-fluoro-5-methyl-1H-indol-3-yl)ethanone 14a (1.22 g, 3.87 mmol) in THF (125 mL) was cooled to 0° C. A solution of phenyltrimethylammonium tribromide [CAS 4207-56-1] (1.6 g, 4.26 mmol) in THF (25 mL) was added dropwise. The reaction mixture was stirred at 0° C. for 2 h and at room temperature for 2 h. The solids were removed by filtration and washed with THF. The combined filtrates were evaporated under reduced pressure. The residue was mixed with EtOAc (50 mL). The solids were isolated by filtration, washed with a small amount of EtOAc and dried under vacuum at 50° C. to provide 2-bromo-2-(4-fluoro-2-methoxyphenyl)-1-(6-fluoro-5-methyl-1H-indol-3-yl)ethanone 14b (1.48 g), which was used without further purification in the next step.

Synthesis of Compound 14 and chiral separation of Enantiomers 14A and 14B

A mixture 2-bromo-2-(4-fluoro-2-methoxyphenyl)-1-(6-fluoro-5-methyl-1H-indol-3-yl)ethanone 14b (1.5 g, 3.65 mmol), 3-methoxy-5-(methylsulfonyl)aniline [CAS 62606-02-4] (1.10 g, 5.48 mmol) and diisopropylethylamine (629 µL, 3.65 mmol) in CH$_3$CN (100 mL) was stirred at 85° C. overnight. The reaction mixture was concentrated under reduced pressure. The residue was dissolved in CH$_2$Cl$_2$ (100 mL), washed with 1N HCl (100 mL) and water (100 mL), dried over MgSO$_4$, filtered and evaporated under reduced pressure. The residue was purified by flash chromatography on silica (Stationary phase: Grace Reveleris® silica 120 g, Mobile phase: EtOAc:EtOH(3:1)/heptane gradient 0/100 to 50/50). The desired fractions were combined and evaporated under reduced pressure. The residual solid was stirred up in CH$_2$Cl$_2$ (20 mL). The precipitate was filtered off and washed with CH$_2$Cl$_2$. The solid was stirred up in MeOH (20 mL). The precipitate was filtered off and washed with MeOH. The solid (630 mg) was further purified via preparative HPLC (Stationary phase: Uptisphere® C18 ODB—10 µm, 200 g, 5 cm, Mobile phase: 0.25% NH$_4$HCO$_3$ solution in water, CH$_3$CN). The desired fractions were combined, evaporated under reduced pressure, and co-evaporated with EtOAc (20 mL) to give 2-(4-fluoro-2-methoxyphenyl)-1-(6-fluoro-5- methyl-1H-indol-3-yl)-2-((3-methoxy-5-(methylsulfonyl)phenyl)amino)ethanone (Compound 14, 426 mg) as a racemic mixture.

Chiral separation of the enantiomers of Compound 14 (426 mg) was performed via preparative SFC (Stationary phase: Chiralpak® Diacel AD 20×250 mm, Mobile phase: $CO_2$, EtOH+0.4% iPrNH$_2$). The product fractions were combined and evaporated to provide Enantiomer 14A as the first eluted product and Enantiomer 14B as the second eluted product. Both enantiomers 14A and 14B were solidified as follows: the evaporation residues were stirred up in $H_2O$/MeOH 1/1 (5 mL) for 1 h, The precipitate was isolated by filtration, washed with $H_2O$/MeOH 1/1 and dried at under vacuum at 50° C. to provide Enantiomer 14A (113 mg) and Enantiomer 14B (97 mg) as white powders.

Compound 14:

$^1$H NMR (400 MHz, DMSO-d$_6$) δ ppm 2.30 (d, J=1.3 Hz, 3 H) 3.08 (s, 3 H) 3.72 (s, 3 H) 3.99 (s, 3 H) 6.21 (d, J=7.7 Hz, 1 H) 6.58 (d, J=1.8 Hz, 2 H) 6.73 (td, J=8.5, 2.5 Hz, 1 H) 6.91 (t, J=1.8 Hz, 1 H) 6.95 (dd, J=11.4, 2.4 Hz, 1 H) 6.99 (d, J=7.7 Hz, 1 H) 7.22 (d, J=10.3 Hz, 1 H) 7.36 (dd, J=8.6, 6.8 Hz, 1 H) 8.03 (d, J=7.9 Hz, 1 H) 8.37 (s, 1 H) 11.95 (br s, 1 H)

LC/MS (method LC-B): R$_t$ 2.07 min, MH$^+$ 515

Enantiomer 14A:

$^1$H NMR (400 MHz, DMSO-d$_6$) δ ppm 2.30 (d, J=1.5 Hz, 3 H) 3.08 (s, 3 H) 3.72 (s, 3 H) 3.99 (s, 3 H) 6.21 (d, J=7.7 Hz, 1 H) 6.58 (d, J=1.5 Hz, 2 H) 6.73 (td, J=8.5, 2.6 Hz, 1 H) 6.91 (t, J=1.7 Hz, 1 H) 6.95 (dd, J=11.3, 2.5 Hz, 1 H) 6.98 (d, J=7.7 Hz, 1 H) 7.22 (d, J=10.3 Hz, 1 H) 7.36 (dd, J=8.6, 6.8 Hz, 1 H) 8.03 (d, J=7.9 Hz, 1 H) 8.37 (s, 1 H) 11.95 (br s, 1 H)

LC/MS (method LC-B): R$_t$ 2.06 min, MH$^+$ 515

$[α]_D^{20}$: +150.0° (c 0.51, DMF)

Chiral SFC (method SFC-J): R$_t$ 3.49 min, MH$^+$ 515, chiral purity 100%.

Enantiomer 14B:

$^1$H NMR (400 MHz, DMSO-d$_6$) δ ppm 2.31 (d, J=1.3 Hz, 3 H) 3.09 (s, 3 H) 3.72 (s, 3 H) 3.99 (s, 3 H) 6.21 (d, J=7.9 Hz, 1 H) 6.59 (d, J=1.8 Hz, 2 H) 6.73 (td, J=8.5, 2.4 Hz, 1 H) 6.92 (t, J=1.8 Hz, 1 H) 6.95 (dd, J=11.4, 2.4 Hz, 1 H) 6.99 (d, J=7.7 Hz, 1 H) 7.22 (d, J=10.3 Hz, 1 H) 7.36 (dd, J=8.6, 7.0 Hz, 1 H) 8.03 (d, J=7.9 Hz, 1 H) 8.37 (s, 1 H) 11.95 (br s, 1 H)

LC/MS (method LC-B): R$_t$ 2.06 min, MH$^+$ 515

$[α]_D^{20}$: −137.3° (c 0.52, DMF)

Chiral SFC (method SFC-J): R$_t$ 3.85 min, MH$^+$ 515, chiral purity 100%.

Example 15 synthesis 2-(4-fluoro-2-methoxyphenyl)-2-((3-methoxy-5-(methyl-sulfonyl)phenyl)amino)-1-(5-methyl-1H-indol-3-yl)ethanone (Compound 15) and chiral separation into Enantiomers 15A and 15B

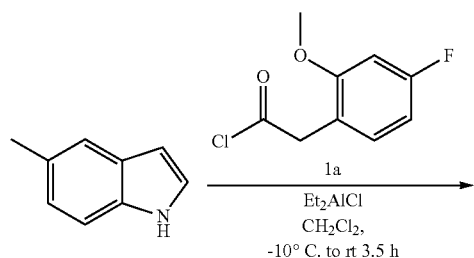

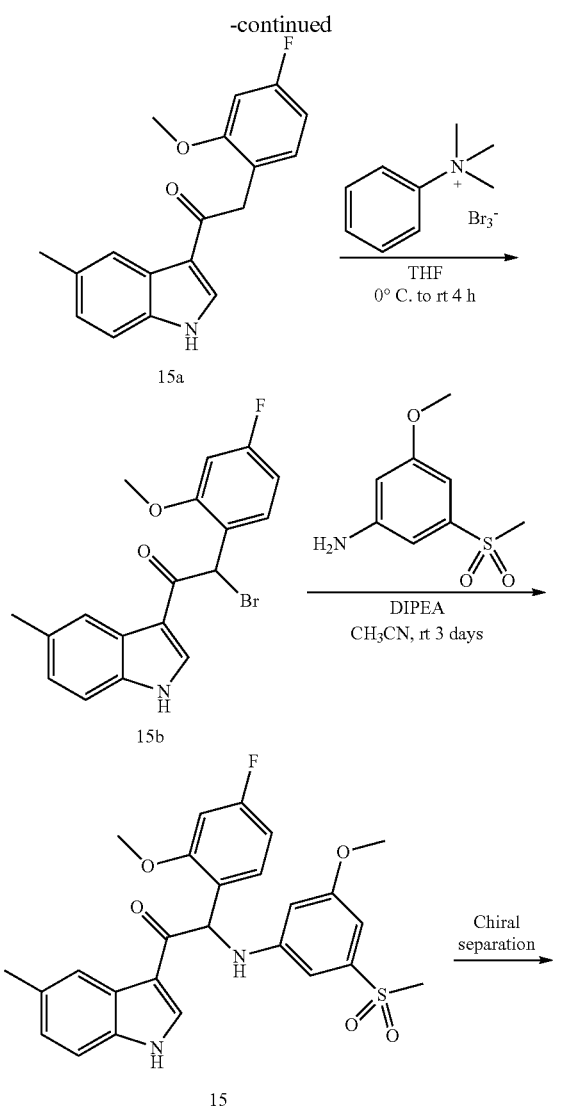

Synthesis of Intermediate 15a

A solution 5-methyl-1H-indole [CAS 614-96-0] (5 g, 38.1 mmol) in $CH_2Cl_2$ (100 mL) was cooled to −10° C. under $N_2$-atmosphere. A solution of diethylaluminum chloride 1M in hexane (57.2 mL, 57.2 mmol) was added dropwise and the resulting mixture was kept at −10° C. for 10 min. A solution of 2-(4-fluoro-2-methoxyphenyl)acetyl chloride 1a (11.6 g, 57.2 mmol) in $CH_2Cl_2$ (100 mL) was added dropwise. The reaction mixture was stirred at room temperature for 3.5 h. The reaction mixture was poured out in a stirring ice/Rochelle salt solution. The mixture was filtered over Dicalite® and the filter cake was washed several times with THF. The filtrates were combined. The layers were separated and the organic layer was washed with water, dried over $MgSO_4$, filtered and evaporated under reduced pressure. The solid residue was suspended in $CH_2Cl_2$ (30 mL). The precipitate was filtered off, washed (2×) with a small amount of $CH_2Cl_2$ and dried under vacuum at 50° C. to provide 2-(4-fluoro-2-methoxyphenyl)-1-(5-methyl-1H-indol-3-yl)ethanone 15a (7.19 g).

Synthesis of Intermediate 15b

A stirred solution of 2-(4-fluoro-2-methoxyphenyl)-1-(5-methyl-1H-indol-3-yl)-ethanone 15a (7.19 g, 24.2 mmol) in THF (500 mL) was cooled to 0° C. A solution of phenyltrimethylammonium tribromide [CAS 4207-56-1] (10 g, 26.6 mmol) in THF (150 mL) was added dropwise. The reaction mixture was stirred at room temperature for 4 h. The solids were removed by filtration and washed with THF. The combined filtrates were evaporated under reduced pressure. The residue was mixed with EtOAc (50 mL). The solids were isolated by filtration, washed with a small amount of EtOAc and dried under vacuum at 50° C. to provide 2-bromo-2-(4-fluoro-2-methoxyphenyl)-1-(5-methyl-1H-indol-3-yl)ethanone 15b (8.02 g).

Synthesis of Compound 15 and chiral separation of Enantiomers 15A and 15B

A mixture 2-bromo-2-(4-fluoro-2-methoxyphenyl)-1-(5-methyl-1H-indol-3-yl)-ethanone 15b (3.5 g, 9.3 mmol), 3-methoxy-5-(methylsulfonyl)aniline [CAS 62606-02-4] (2.81 g, 14 mmol) and diisopropylethylamine (1.60 mL, 9.3 mmol) in CH₃CN was stirred overnight at room temperature. The reaction temperature was increased to 80° C. for 1 h and the mixture was subsequently stirred again at room temperature for 2 days. The reaction mixture was concentrated under reduced pressure. The residue was dissolved in CH₂Cl₂ (100 mL), washed with 1N HCl (100 mL) and brine (100 mL), dried over MgSO₄, filtered and evaporated under reduced pressure. The residue was purified by column chromatography (Stationary phase: Grace Reveleris® silica 120 g, Mobile phase: EtOAc/heptane gradient 35/65 to 45/55). The desired fractions were combined and evaporated under reduced pressure. The residue (3.96 g) was further purified via preparative HPLC (Stationary phase: Uptisphere® C18 ODB—10 µm, 200 g, 5 cm, Mobile phase: 0.25% NH₄HCO₃ solution in water, CH₃CN). The desired fractions were combined, evaporated under reduced pressure, and co-evaporated with EtOAc (20 mL). The residual solid was stirred up in a mixture of MeOH (5 mL) and water (5 mL) for 1 h. The precipitate was filtered off and dried under vacuum to give 2-(4-fluoro-2-methoxyphenyl)-2-((3-methoxy-5-(methylsulfonyl)phenyl)amino)-1-(5-methyl-1H-indol-3-yl)ethanone (Compound 15, 1.92 g) as a racemic mixture. Chiral separation of the enantiomers of Compound 15 (1.50 g) was performed via Normal Phase Chiral separation (Stationary phase: AS 20 µm, Mobile phase: 100% methanol). The product fractions were combined and evaporated to provide Enantiomer 15A (742 mg) as the first eluted product and Enantiomer 15B (745 mg) as the second eluted product. Enantiomer 15A was further purified by column chromatography on silica (stationary phase: Grace Reveleris® silica 40 g, Mobile phase: CH₂Cl₂/MeOH gradient 100/0 to 90/10). The fractions containing product were combined and evaporated. The solid residue was stirred up in MeOH/water (1/1) (14 mL) for 2 h. The precipitate was filtered off and dried under vacuum at 50° C. to provide Enantiomer 15A (361 mg) as a white powder. Enantiomer 15B was stirred up in MeOH/water (1/1) (14 mL) for 5 h. The precipitate was filtered off and dried under vacuum at 50° C. to provide Enantiomer 15B (445 mg) as a white powder.

Compound 15:

$^1$H NMR (360 MHz, DMSO-d$_6$) δ ppm 2.39 (s, 3 H) 3.09 (s, 3 H) 3.72 (s, 3 H) 4.00 (s, 3 H) 6.22 (d, J=7.7 Hz, 1 H) 6.55-6.62 (m, 2 H) 6.73 (td, J=8.5, 2.4 Hz, 1 H) 6.92 (br s, 1 H) 6.96 (dd, J=11.3, 2.6 Hz, 1 H) 6.99-7.06 (m, 2 H) 7.31-7.39 (m, 2 H) 7.98 (s, 1 H) 8.37 (s, 1 H) 11.94 (br s, 1 H)

LC/MS (method LC-A): R$_t$ 1.09 min, MH$^+$ 497

Enantiomer 15A:

$^1$H NMR (400 MHz, DMSO-d$_6$) δ ppm 2.39 (s, 3 H) 3.08 (s, 3 H) 3.72 (s, 3 H) 4.00 (s, 3 H) 6.21 (d, J=7.7 Hz, 1 H) 6.56-6.61 (m, 2 H) 6.72 (td, J=8.5, 2.4 Hz, 1 H) 6.92 (t, J=1.7 Hz, 1 H) 6.95 (dd, J=11.2, 2.4 Hz, 1 H) 6.99 (d, J=7.7 Hz, 1 H) 7.04 (dd, J=8.4, 1.3 Hz, 1 H) 7.32-7.39 (m, 2 H) 7.98 (s, 1 H) 8.36 (s, 1 H) 11.92 (br s, 1 H)

LC/MS (method LC-B): R$_t$ 2.03 min, MH$^+$ 497

$[\alpha]_D^{20}$: +149.8° (c 0.49, DMF)

Chiral SFC (method SFC-J): R$_t$ 3.67 min, MH$^+$ 497, chiral purity 100%.

Enantiomer 15B:

$^1$H NMR (360 MHz, DMSO-d$_6$) δ ppm 2.39 (s, 3 H) 3.09 (s, 3 H) 3.72 (s, 3 H) 4.00 (s, 3 H) 6.21 (d, J=7.7 Hz, 1 H) 6.55-6.61 (m, 2 H) 6.73 (td, J=8.5, 2.4 Hz, 1 H) 6.92 (t, J=1.6 Hz, 1 H) 6.96 (dd, J=11.3, 2.2 Hz, 1 H) 7.00-7.06 (m, 2 H) 7.31-7.39 (m, 2 H) 7.98 (s, 1 H) 8.37 (s, 1 H) 11.95 (br s, 1 H)

LC/MS (method LC-B): R$_t$ 2.03 min, MH$^+$ 497

$[\alpha]_D^{20}$: −149.3° (c 0.515, DMF)

Chiral SFC (method SFC-J): R$_t$ 4.06 min, MH$^+$ 497, chiral purity 99.6%.

Example 16 synthesis 1-(5-chloro-6-methoxy-1H-indol-3-yl)-2-(4-fluoro-2-methoxyphenyl)-2-((3-methoxy-5-(methylsulfonyl)phenyl)amino)ethanone (Compound 16) and chiral separation into Enantiomers 16A and 16B

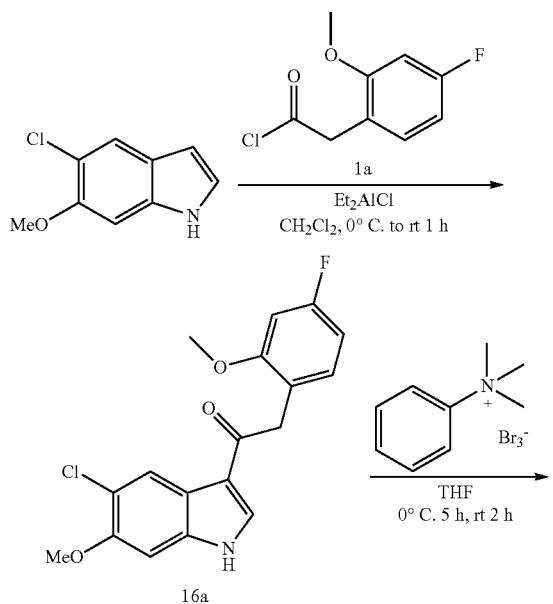

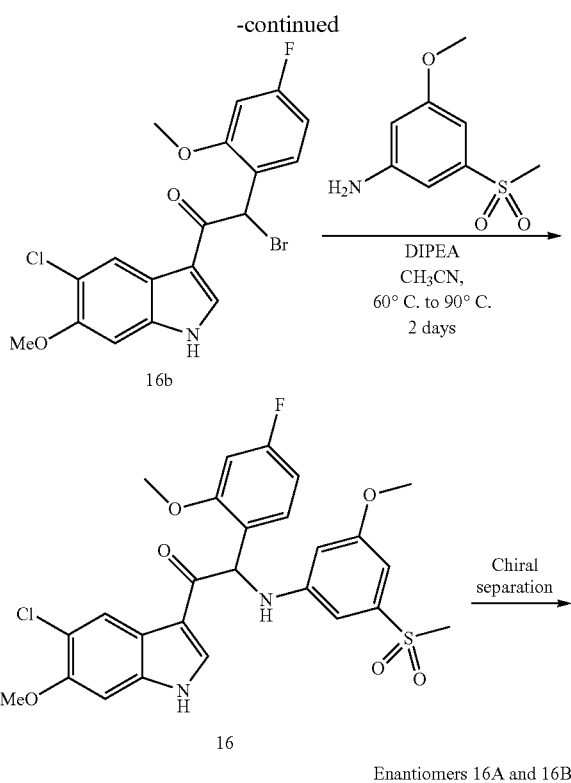

Synthesis of Intermediate 16a

A solution 5-chloro-6-methoxy-1H-indole [CAS 90721-60-1] (4 g, 22 mmol) in CH$_2$Cl$_2$ (150 mL) was cooled to 0° C. under N$_2$-atmosphere. A solution of diethyl-aluminum chloride 1M in hexane (33 mL, 33 mmol) was added dropwise and the resulting mixture was kept at 0° C. for 15 min. A solution of 2-(4-fluoro-2-methoxy-phenyl)acetyl chloride 1a (6.25 g, 30.8 mmol) in CH$_2$Cl$_2$ (50 mL) was added dropwise. The reaction mixture was stirred at 0° C. for 1 h and subsequently at room temperature for 1 h. The reaction mixture was poured out in a stirring ice/Rochelle salt solution. The mixture was filtered over Dicalite® and the filter cake was washed several times with THF. The filtrates were combined. The layers were separated and the organic layer was washed with brine, dried over MgSO$_4$, filtered and evaporated under reduced pressure. The residue was mixed with CH$_2$Cl$_2$ (50 mL). The solids were filtered off and dried under vacuum at 50° C. to provide 1-(5-chloro-6-methoxy-1H-indol-3-yl)-2-(4-fluoro-2-methoxyphenyl)-ethanone 16a (4.01 g) as a powder. The filtrate was evaporated under reduced pressure. The residue was taken up with CH$_2$Cl$_2$ (10 mL). The solids were filtered off and dried under vacuum at 50° C. to provide a second crop of 16a (369 mg).

Synthesis of Intermediate 16b

A stirred solution of 1-(5-chloro-6-methoxy-1H-indol-3-yl)-2-(4-fluoro-2-methoxyphenyl)ethanone 16a (3.5 g, 8.96 mmol) in THF (500 mL) was cooled to 0° C. A solution of phenyltrimethylammonium tribromide [CAS 4207-56-1] (3.7 g, 9.85 mmol) in THF (100 mL) was added dropwise. The reaction mixture was stirred under cooling (0° C.) for 5 h and subsequently at room temperature for 2 h. The solids were removed by filtration and washed with THF. The combined filtrates were evaporated under reduced pressure. The residue was mixed with EtOAc (50 mL). The solids were isolated by filtration, washed with a small amount of EtOAc and dried under vacuum at 50° C. to provide 2-bromo-1-(5-chloro-6-methoxy-1H-indol-3-yl)-2-(4-fluoro-2-methoxyphenyl)ethanone 16b (3.02 g).

Synthesis of Compound 16 and chiral separation of Enantiomers 16A and 16B

A mixture 2-bromo-1-(5-chloro-6-methoxy-1H-indol-3-yl)-2-(4-fluoro-2-methoxy-phenyl)ethanone 16b (3.02 g, 6.58 mmol), 3-methoxy-5-(methylsulfonyl)aniline [CAS 62606-02-4] (1.81 g, 8.99 mmol) and diisopropylethylamine (1.13 mL, 6.58 mmol) in CH$_3$CN (120 mL) was stirred overnight at 60° C. The reaction temperature was increased to 80° C. for 8 h and finally to 90° C. with overnight stirring. The reaction mixture was concentrated under reduced pressure. The residue was dissolved in CH$_2$Cl$_2$ (100 mL), washed with 1N HCl (100 mL) and water (100 mL), dried over MgSO$_4$, filtered and evaporated under reduced pressure. The residue was purified via Preparative HPLC (Stationary phase: RP XBridge® Prep C18 OBD—10 μm, 50×150 mm, Mobile phase: 0.25% NH$_4$HCO$_3$ solution in water, CH$_3$CN). The desired fractions were combined and evaporated under reduced pressure. The residue was stirred up in EtOAc (20 mL). The solids were isolated by filtration to provide a first crop of 1-(5-chloro-6-methoxy-1H-indol-3-yl)-2-(4-fluoro-2-methoxyphenyl)-2-((3-methoxy-5-(methylsulfonyl)phenyl)-amino)ethanone (Compound 16, 309 mg) as a racemic mixture. The filtrate was evaporated under reduced pressure. MeOH was added and the resulting suspension was stirred up for 30 min. the Solids were filtered off to provide a second crop of racemic Compound 16 (423 mg).

Chiral separation of the enantiomers of Compound 16 (493 mg) was performed via Normal Phase Chiral separation (Stationary phase: AS 20 μm, Mobile phase: 100% methanol). The product fractions were combined and evaporated to provide Enantiomer 16A as the first eluted product and Enantiomer 16B as the second eluted product. Enantiomer 16A was stirred up in MeOH (5 mL) for 30 min. The precipitate was filtered off, washed with MeOH (2×2 mL) and dried under vacuum at 50° C. to provide Enantiomer 16A (156 mg) as a white powder. Enantiomer 16B was stirred up in MeOH (5 mL) for 30 min. The precipitate was filtered off, washed with MeOH (2×2 mL) and dried under vacuum at 50° C. to provide Enantiomer 16B (146 mg) as a white powder.

Compound 16:
$^1$H NMR (400 MHz, DMSO-d$_6$) δ ppm 3.08 (s, 3 H) 3.72 (s, 3 H) 3.87 (s, 3 H) 3.99 (s, 3 H) 6.20 (d, J=7.7 Hz, 1 H) 6.59 (d, J=1.3 Hz, 2 H) 6.73 (td, J=8.5, 2.4 Hz, 1 H) 6.91 (t, J=1.8 Hz, 1 H) 6.96 (dd, J=11.4, 2.4 Hz, 1 H) 7.01 (d, J=7.9 Hz, 1 H) 7.14 (s, 1 H) 7.36 (dd, J=8.6, 6.8 Hz, 1 H) 8.12 (s, 1 H) 8.35 (s, 1 H) 11.98 (br s, 1 H)
LC/MS (method LC-B): R$_t$ 2.02 min, MH$^+$ 547

Enantiomer 16A:
$^1$H NMR (400 MHz, DMSO-d$_6$) δ ppm 3.08 (s, 3 H) 3.72 (s, 3 H) 3.86 (s, 3 H) 3.99 (s, 3 H) 6.20 (d, J=7.7 Hz, 1 H) 6.55-6.62 (m, 2 H) 6.73 (td, J=8.5, 2.4 Hz, 1 H) 6.90 (t, J=1.2 Hz, 1 H) 6.95 (dd, J=11.3, 2.5 Hz, 1 H) 7.00 (d, J=7.9 Hz, 1 H) 7.14 (s, 1 H) 7.36 (dd, J=8.6, 6.8 Hz, 1 H) 8.11 (s, 1 H) 8.34 (s, 1 H) 11.97 (br s, 1 H)
LC/MS (method LC-A): R$_t$ 1.10 min, MH$^+$ 547
$[\alpha]_D^{20}$: +138.10 (c 0.565, DMF)

Chiral SFC (method SFC-J): $R_t$ 4.17 min, MH+ 547, chiral purity 100%.

Melting point: 252° C.

Enantiomer 16B:

$^1$H NMR (400 MHz, DMSO-$d_6$) δ ppm 3.08 (s, 3 H) 3.72 (s, 3 H) 3.86 (s, 3 H) 3.99 (s, 3 H) 6.20 (d, J=7.9 Hz, 1 H) 6.58 (d, J=1.3 Hz, 2 H) 6.73 (td, J=8.5, 2.4 Hz, 1 H) 6.91 (t, J=1.5 Hz, 1 H) 6.95 (dd, J=11.4, 2.4 Hz, 1 H) 7.00 (d, J=7.7 Hz, 1 H) 7.14 (s, 1 H) 7.36 (dd, J=8.6, 7.0 Hz, 1 H) 8.11 (s, 1 H) 8.34 (s, 1 H) 11.98 (brs, 1 H)

LC/MS (method LC-A): $R_t$ 1.11 min, MH+ 547

$[α]_D^{20}$: −121.7° (c 0.545, DMF)

Chiral SFC (method SFC-J): $R_t$ 4.57 min, MH+ 547, chiral purity 100%.

Melting point: 253° C.

Example 17 synthesis of 2-(4-fluoro-2-methoxyphenyl)-2-((3-methoxy-5-(methyl-sulfonyl)phenyl)amino)-1-(5-(trifluoromethyl)-1H-indol-3-yl)ethanone (Compound 17) and chiral separation into Enantiomers 17A and 17B

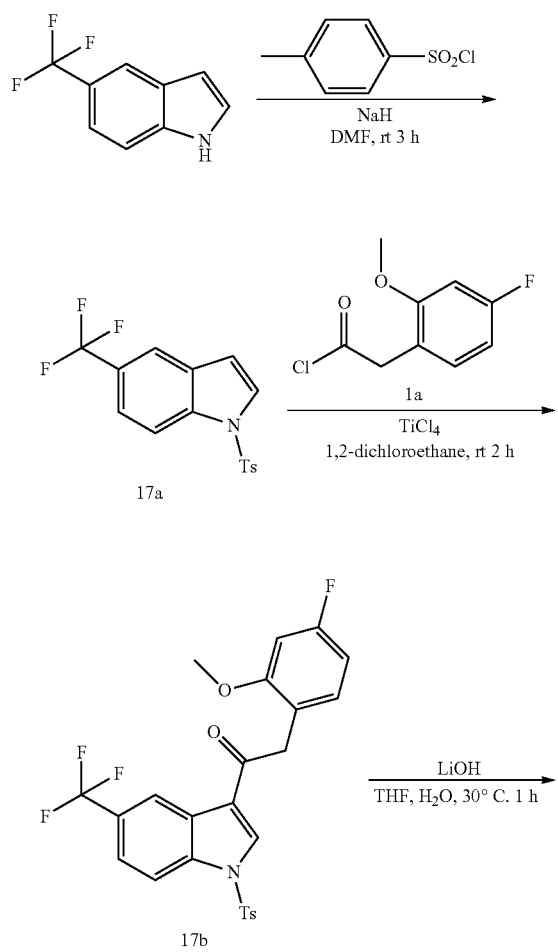

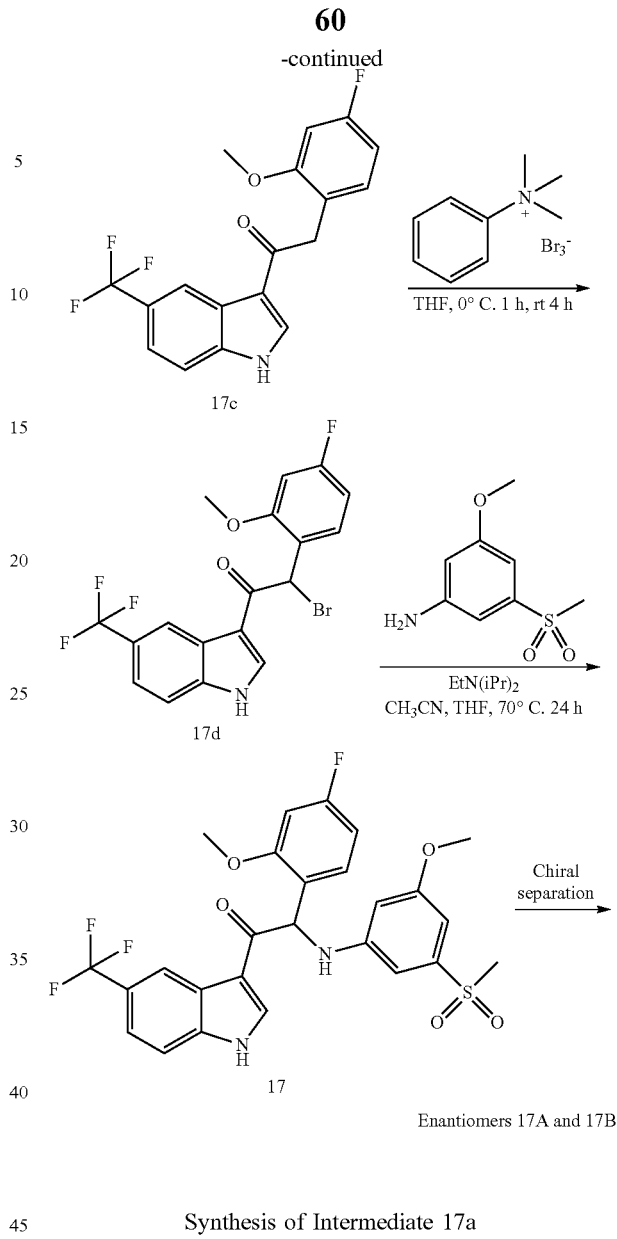

Enantiomers 17A and 17B

Synthesis of Intermediate 17a

At 0° C., under a N$_2$ flow, sodium hydride (2.48 g, 64.81 mmol) was added portionwise to a mixture of 5-(trifluoromethyl)-1H-indole [CAS 100846-24-0] (10 g, 54.01 mmol) in DMF (150 mL) and the mixture was stirred at 0° C. for 30 min. A solution of tosyl chloride (11.3 g, 59.4 mmol) in DMF (50 mL) was added dropwise and the resulting mixture was stirred at room temperature for 3 h. After cooling to 0° C., the reaction was quenched by the addition of water. The resulting precipitate was filtered off and dried under vacuum at 70° C. overnight to give 1-tosyl-5-(trifluoromethyl)-1H-indole 17a (18.4 g).

Synthesis of Intermediate 17b

Titanium(IV) chloride (2.32 mL, 21.2 mmol) was added dropwise at room temperature to a stirred solution of 1-tosyl-5-(trifluoromethyl)-1H-indole 17a (3.6 g, 10.6 mmol) and 2-(4-fluoro-2-methoxyphenyl)acetyl chloride 1a (3.85 g, 19 mmol, synthesis: see Example 1) in 1,2-dichloroethane (70 mL). The reaction was stirred at room temperature for 2 h. Ice-water was added. The reaction mixture was extracted with EtOAc. The organic layer was dried over MgSO$_4$, filtered, and the solvent was concentrated under reduced pressure. The crude compound was purified by column chromatography on silica gel (15-40 μm, 80 g, CH$_2$Cl$_2$/MeOH 99.5/0.5). The fractions containing Compound 17b were combined and the solvent was evaporated under reduced pressure. The compound was stirred up in CH$_3$CN/diisopropylether. The precipitate was filtered off and dried to give 2-(4-fluoro-2-methoxyphenyl)-1-(1-tosyl-5-(trifluoromethyl)-1H-indol-3-yl)ethanone 17b (3 g).

Synthesis of Intermediate 17c

Lithium hydroxide (0.66 g, 15.8 mmol) was added to a solution of 2-(4-fluoro-2-methoxyphenyl)-1-(1-tosyl-5-(trifluoromethyl)-1H-indol-3-yl)ethanone 17b (3.2 g, 6.33 mmol) in THF (18 mL) and water (6 mL). The mixture was stirred at 30° C. for 1 h. Water and EtOAc were added. The organic layer was separated, dried over MgSO$_4$, filtered and the solvent was evaporated under reduced pressure. The solid residue was stirred up in diisopropylether. The precipitate was filtered off and dried to give 2-(4-fluoro-2-methoxyphenyl)-1-(5-(trifluoromethyl)-1H-indol-3-yl)-ethanone 17c (2.1 g).

Synthesis of Intermediate 17d

At 0° C., a solution of phenyltrimethylammonium tribromide [CAS 4207-56-1] (1.6 g, 4.27 mmol) in THF (50 mL) was added dropwise to a mixture of 2-(4-fluoro-2-methoxyphenyl)-1-(5-(trifluoromethyl)-1H-indol-3-yl)ethanone 17c (1.5 g, 4.27 mmol) in THF (50 mL). The mixture was stirred at 0° C. for 1 h and at room temperature for 4 h. The precipitate was filtered off and washed with EtOAc. The combined filtrates were concentrated under reduced pressure. The residue was dissolved in EtOAc. The organic layer was washed with water, dried over MgSO$_4$, filtered, and the solvent was evaporated under reduced pressure. The residue was stirred up in diisopropylether. The precipitate was filtered off and dried to give 2-bromo-2-(4-fluoro-2-methoxyphenyl)-1-(5-(trifluoromethyl)-1H-indol-3-yl)-ethanone 17d (1.8 g).

Synthesis of Compound 17 and chiral separation of Enantiomers 17A and 17B

A mixture of 2-bromo-2-(4-fluoro-2-methoxyphenyl)-1-(5-(trifluoromethyl)-1H-indol-3-yl)ethanone 17d (1.2 g, 2.79 mmol), 3-methoxy-5-(methylsulfonyl)aniline [CAS 62606-02-4] (617 mg, 3.07 mmol) and diisopropylethylamine (0.48 mL, 2.79 mmol) in CH$_3$CN (60 mL) and THF (30 mL) was stirred at 70° C. for 24 h. The solution was concentrated under reduced pressure. The residue was dissolved in EtOAc and the solution was washed with 1 N HCl. The organic layer was separated, dried over MgSO$_4$, filtered and evaporated under reduced pressure. The residue was purified by column chromatography on silica gel (15-40 μm, 80 g, CH$_2$Cl$_2$/MeOH 99.5/0.5). The fractions containing Compound 17 were combined and the solvent was evaporated under reduced pressure. The compound was crystallized from diisopropylether/CH$_3$CN to give 2-(4-fluoro-2-methoxyphenyl)-2-((3-methoxy-5-(methylsulfonyl)phenyl)amino)-1-(5-(trifluoromethyl)-1H-indol-3-yl)ethanone (Compound 17, 410 mg) as a racemic mixture.

The Enantiomers of Compound 17 were separated via preparative Chiral SFC (Stationary phase: Chiralpak® AD-H 5 μm 250×20 mm, Mobile phase: 75% CO$_2$, 25% iPrOH) to give, after crystallization from petroleum ether/diisopropylether, 147 mg of the first eluted enantiomer 17A and 150 mg of the second eluted enantiomer 17B.

Compound 17:

$^1$H NMR (500 MHz, DMSO-d$_6$) δ ppm 3.09 (s, 3 H) 3.72 (s, 3 H) 3.98 (s, 3 H) 6.27 (d, J=7.9 Hz, 1 H) 6.59 (d, J=1.3 Hz, 2 H) 6.74 (td, J=8.4, 2.4 Hz, 1 H) 6.92 (s, 1 H) 6.97 (dd, J=11.3, 2.5 Hz, 1 H) 7.06 (d, J=7.9 Hz, 1 H) 7.37 (dd, J=8.5, 6.9 Hz, 1 H) 7.54 (dd, J=8.5, 1.6 Hz, 1 H) 7.69 (d, J=8.5 Hz, 1 H) 8.49 (s, 1 H) 8.60 (s, 1 H) 12.43 (br s, 1 H)

LC/MS (method LC-C): R$_t$ 3.09 min, MH$^+$ 551

Melting point: 160° C.

Enantiomer 17A:

$^1$H NMR (400 MHz, DMSO-d$_6$) δ ppm 3.09 (s, 3 H) 3.72 (s, 3 H) 3.98 (s, 3 H) 6.27 (d, J=7.6 Hz, 1 H) 6.59 (d, J=1.5 Hz, 2 H) 6.74 (td, J=8.5, 2.3 Hz, 1 H) 6.92 (s, 1 H) 6.96 (dd, J=11.4, 2.3 Hz, 1 H) 7.04 (d, J=7.6 Hz, 1 H) 7.37 (dd, J=8.6, 7.1 Hz, 1 H) 7.53 (dd, J=8.6, 1.5 Hz, 1 H) 7.69 (d, J=8.6 Hz, 1 H) 8.49 (s, 1 H) 8.59 (s, 1 H) 12.39 (br s, 1 H)

LC/MS (method LC-C): R$_t$ 3.13 min, MH$^+$ 551

$[α]_D^{20}$: −119.3° (c 0.2364, DMF)

Chiral SFC (method SFC-H): R$_t$ 3.40 min, MH$^+$ 551, chiral purity 100%.

Melting point: 231° C.

Enantiomer 17B:

$^1$H NMR (400 MHz, DMSO-d$_6$) δ ppm 3.09 (s, 3 H) 3.73 (s, 3 H) 3.99 (s, 3 H) 6.27 (brd, J=8.1 Hz, 1 H) 6.59 (s, 2 H) 6.74 (td, J=8.2, 2.3 Hz, 1 H) 6.92 (s, 1 H) 6.96 (br d, J=11.6 Hz, 1 H) 7.05 (br d, J=8.1 Hz, 1 H) 7.33-7.41 (m, 1 H) 7.54 (br d, J=8.6 Hz, 1 H) 7.69 (br d, J=8.6 Hz, 1 H) 8.49 (s, 1 H) 8.60 (s, 1 H) 12.37 (br s, 1 H)

LC/MS (method LC-C): R$_t$ 3.13 min, MH$^+$ 551

$[α]_D^{20}$: +112.8° (c 0.2545, DMF)

Chiral SFC (method SFC-H): R$_t$ 4.45 min, MH$^+$ 551, chiral purity 100%.

Melting point: 230° C.

Example 18 synthesis 2-(4-fluoro-2-methoxyphenyl)-2-((3-methoxy-5-(methyl-sulfonyl)phenyl)amino)-1-(5-(trifluoromethoxy)-1H-indol-3-yl)ethanone (Compound 18) and chiral separation into Enantiomers 18A and 18B

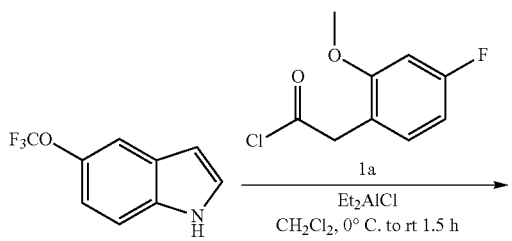

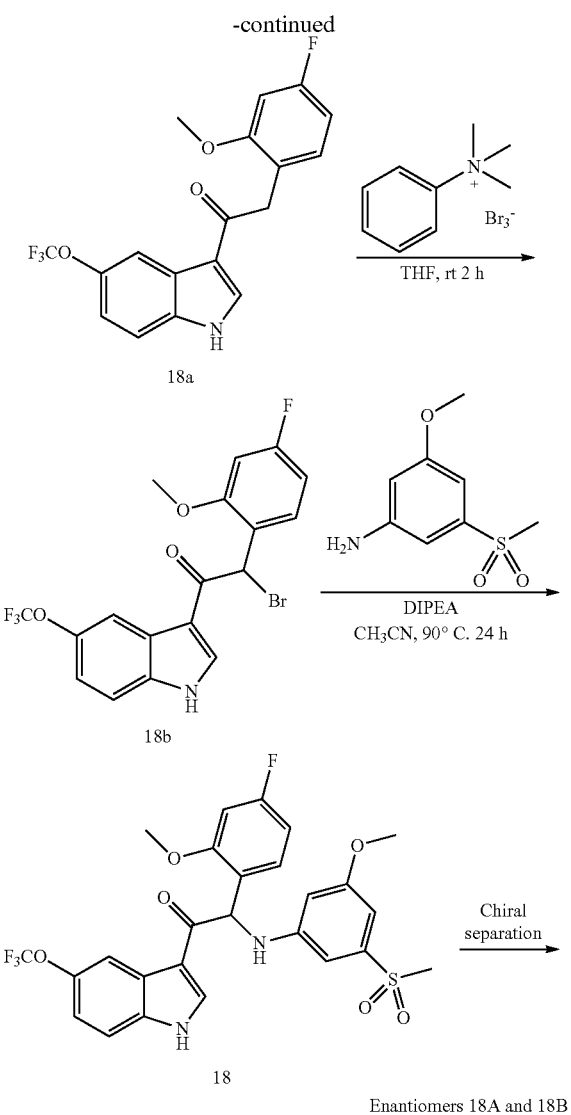

Synthesis of Intermediate 18a

A solution of 5-(trifluoromethoxy)-1H-indole [CAS 262593-63-5] (5 g, 24.9 mmol) in CH$_2$Cl$_2$ (150 mL) was cooled to 0° C. under N$_2$-atmosphere. A solution of diethylaluminum chloride 1M in hexane (37.3 mL, 37.3 mmol) was added dropwise and the resulting mixture was kept at 0° C. for 15 min. A solution of 2-(4-fluoro-2-methoxyphenyl) acetyl chloride 1a (7.05 g, 34.8 mmol) in CH$_2$Cl$_2$ (50 mL) was added dropwise. Stirring was continued at 0° C. for 1 h and at room temperature for 1.5 h. The reaction mixture was poured out in a stirring ice/Rochelle salt solution. After the ice had melted, the mixture was filtered over Dicalite® and the filter cake was washed several times with THF. The filtrates were combined. The layers were separated and the organic layer washed with brine, dried over MgSO$_4$, filtered and evaporated under reduced pressure. The residue was triturated with CH$_2$Cl$_2$ (50 mL) and the precipitate was filtered off to provide 2-(4-fluoro-2-methoxy-phenyl)-1-(5-(trifluoromethoxy)-1H-indol-3-yl)ethanone 18a (7.36 g). The filtrate was concentrated under vacuum and the solid residue was stirred up in CH$_2$Cl$_2$ (10 mL). Filtration of the solids provided a second crop of 18a (431 mg).

Synthesis of Intermediate 18b

A stirred solution of 2-(4-fluoro-2-methoxyphenyl)-1-(5-(trifluoromethoxy)-1H-indol-3-yl)ethanone 18a (7.35 g, 20.0 mmol) in THF (200 mL) was cooled to 0° C. A solution of phenyltrimethylammonium tribromide [CAS 4207-56-1] (8.28 g, 22.0 mmol) in THF (100 mL) was added dropwise. The resulting suspension was stirred at room temperature for 2 h. The solids were removed by filtration and washed with THF. The combined filtrates were evaporated under reduced pressure. The residue was mixed with EtOAc (30 mL). The solids were isolated by filtration, washed with a small amount of EtOAc and dried under vacuum at 50° C. to provide 2-bromo-2-(4-fluoro-2-methoxyphenyl)-1-(5-(trifluoromethoxy)-1H-indol-3-yl)ethanone 18b (7.8 g).

Synthesis of Compound 18 and chiral separation of Enantiomers 18A and 18B

A mixture 2-bromo-2-(4-fluoro-2-methoxyphenyl)-1-(5-(trifluoromethoxy)-1H-indol-3-yl)ethanone 18b (3 g, 6.72 mmol), 3-methoxy-5-(methylsulfonyl)aniline [CAS 62606-02-4] (1.85 g, 9.18 mmol) and diisopropylethylamine (1.16 mL, 6.72 mmol) in CH$_3$CN (120 mL) was stirred at 90° C. for 24 h. The reaction mixture was concentrated under reduced pressure. The residue was dissolved in CH$_2$Cl$_2$ (100 mL), washed with 1N HCl (100 mL) and water (100 mL), dried over MgSO$_4$, filtered and evaporated under reduced pressure. The residue was purified by column chromatograph on silica (Stationary phase: Grace Reveleris® silica 120 g, Mobile phase: EtOAc:EtOH (3:1)/heptane gradient 0/100 to 50/50). The desired fractions were combined and evaporated under reduced pressure. The residue was stirred up in EtOAc (20 mL). The solids were isolated by filtration and dried under vacuum at 50° C. to provide 2-(4-fluoro-2-methoxyphenyl)-2-((3-methoxy-5-(methylsulfonyl)phenyl)amino)-1-(5-(trifluoromethoxy)-1H-indol-3-yl)ethanone (Compound 18, 608 mg) as a racemic mixture.

Chiral separation of the enantiomers of Compound 18 (578 mg) was performed via Normal Phase Chiral separation (Stationary phase: AS 20 μm, Mobile phase: 100% methanol). The product fractions were combined and evaporated to provide Enantiomer 18A as the first eluted product and Enantiomer 18B as the second eluted product. Enantiomer 18A was precipitated by overnight stirring from MeOH/water. The precipitate was filtered off and dried under vacuum at 50° C. to provide Enantiomer 18A (123 mg) as a white powder. Enantiomer 18B was precipitated by overnight stirring from MeOH/water. The precipitate was filtered off and dried under vacuum at 50° C. to provide Enantiomer 18B (91 mg) as a white powder.

Compound 18:
$^1$H NMR (400 MHz, DMSO-d$_6$) δ ppm 3.09 (s, 3 H) 3.73 (s, 3 H) 3.99 (s, 3 H) 6.25 (d, J=7.7 Hz, 1 H) 6.59 (d, J=1.3 Hz, 2 H) 6.74 (td, J=8.5, 2.5 Hz, 1 H) 6.92 (t, J=1.3 Hz, 1 H) 6.96 (dd, J=11.2, 2.4 Hz, 1 H) 7.05 (d, J=7.7 Hz, 1 H) 7.21 (dd, J=8.7, 1.9 Hz, 1 H) 7.38 (dd, J=8.6, 6.8 Hz, 1 H) 7.59 (d, J=8.8 Hz, 1 H) 8.07 (br s, 1 H) 8.54 (s, 1 H) 12.28 (br s, 1 H)

LC/MS (method LC-B): R$_t$ 2.13 min, MH$^+$ 567

Enantiomer 18A:
$^1$H NMR (400 MHz, DMSO-d$_6$) δ ppm 3.09 (s, 3 H) 3.72 (s, 3 H) 3.99 (s, 3 H) 6.25 (d, J=7.7 Hz, 1 H) 6.59 (d, J=1.5 Hz, 2 H) 6.74 (td, J=8.5, 2.5 Hz, 1 H) 6.91 (t, J=1.7 Hz, 1

H) 6.96 (dd, J=11.2, 2.4 Hz, 1 H) 7.04 (d, J=7.9 Hz, 1 H) 7.21 (dd, J=8.8, 2.0 Hz, 1 H) 7.37 (dd, J=8.7, 6.9 Hz, 1 H) 7.59 (d, J=8.8 Hz, 1 H) 8.07 (d, J=1.1 Hz, 1 H) 8.54 (s, 1 H) 12.29 (br s, 1 H)

LC/MS (method LC-B): $R_t$ 2.12 min, MH$^+$ 567

$[\alpha]_D^{20}$: +112.00 (c 0.465, DMF)

Chiral SFC (method SFC-J): $R_t$ 2.85 min, MH$^+$ 547, chiral purity 100%.

Melting point: 215° C.

Enantiomer 18B:

$^1$H NMR (400 MHz, DMSO-d$_6$) δ ppm 3.09 (s, 3 H) 3.72 (s, 3 H) 3.99 (s, 3 H) 6.25 (d, J=7.7 Hz, 1 H) 6.59 (d, J=1.3 Hz, 2 H) 6.74 (td, J=8.5, 2.5 Hz, 1 H) 6.91 (t, J=1.7 Hz, 1 H) 6.96 (dd, J=11.2, 2.4 Hz, 1 H) 7.04 (d, J=7.9 Hz, 1 H) 7.21 (dd, J=8.7, 1.9 Hz, 1 H) 7.37 (dd, J=8.6, 6.8 Hz, 1 H) 7.59 (d, J=8.8 Hz, 1 H) 8.07 (d, J=0.9 Hz, 1 H) 8.54 (s, 1 H) 12.28 (br s, 1 H)

LC/MS (method LC-B): $R_t$ 2.12 min, MH$^+$ 567

$[\alpha]_D^{20}$: −116.7° (c 0.425, DMF)

Chiral SFC (method SFC-J): $R_t$ 3.17 min, MH$^+$ 547, chiral purity 100%.

Melting point: 214° C.

Antiviral Activity of the Compounds of the Invention

DENV-2 Antiviral Assay

The antiviral activity of all the compounds of the invention was tested against DENV-2 16681 strain which was labeled with enhanced green fluorescent protein (eGPF; Table 1). The culture medium consists of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 25 μL was added to 384-well plates (2500 cells/well), which already contain the antiviral compounds. Typically, these plates contain a 4-fold serial dilution of 9 dilution steps of the test compound at 200 times the final concentration in 100% DMSO (200 nL). In addition, each compound concentration is tested in quadruplicate (final concentration range: 25 μM-0.00038 μM). Finally, each plate contains wells which are assigned as virus controls (containing cells and virus in the absence of compound), cell controls (containing cells in the absence of virus and compound) and medium controls (containing medium in the absence of cells, virus and compounds). To the wells assigned as medium control, 25 μL of culture medium was added instead of Vero cells. Once the cells were added to the plates, the plates were incubated for 30 minutes at room temperature to allow the cells to distribute evenly within the wells. Next, the plates were incubated in a fully humidified incubator (37° C., 5% CO$_2$) until the next day. Then, DENV-2 strain 16681, labeled with eGFP, was added at a multiplicity of infection (MOI) of 0.5. Therefore, 15 μL of virus suspension was added to all the wells containing test compound and to the wells assigned as virus control. In parallel, 15 μL of culture medium was added to the medium and cell controls. Next, the plates were incubated for 3 days in a fully humidified incubator (37° C., 5% CO$_2$). At the day of the read out, the eGFP fluorescence was measured using an automated fluorescence microscope at 488 nm (blue laser). Using an in-house LIMS system, inhibition dose response curves for each compound were calculated and the half maximal effective concentration (EC$_{50}$) was determined. Therefore, the percent inhibition (I) for every test concentration is calculated using the following formula: I=100*(S$_T$−S$_{CC}$)/(S$_{VC}$−S$_{CC}$); S$_T$, S$_{CC}$ and S$_{VC}$ are the amount of eGFP signal in the test compound, cell control and virus control wells, respectively. The EC$_{50}$ represents the concentration of a compound at which the virus replication is inhibited with 50%, as measured by a 50% reduction of the eGFP fluorescent intensity compared to the virus control. The EC$_{50}$ is calculated using linear interpolation.

In parallel, the toxicity of the compounds was assessed on the same plates. Once the read-out for the eGFP signal was done, 10 μL of resazurin, a cell viability stain, was added to all wells of the 384-well plates. The resazurin assay is based on the reduction of the blue resazurin by NADH, produced by the cells, into the highly fluorescent product, resorufin. The formation of pink fluorescent resorufin is directly related to the number of viable cells in the well. The plates were incubated for an additional 5 hours in a fully humidified incubator (37° C., 5% CO$_2$). Next, the plates were measured on an Infinite reader (Tecan) using an excitation wavelength of 530 nm. The half maximal cytotoxic concentration (CC$_{50}$) was also determined, defined as the concentration required to reduce the resazurin conversion by 50% compared to that of the cell control wells. Finally, the selectivity index (SI) was determined for the compounds, which was calculated as followed: SI=CC$_{50}$/EC$_{50}$.

TABLE 1

EC$_{50}$, CC$_{50}$, and SI for the compounds of the invention in the DENV-2 antiviral assay

| compound# | EC$_{50}$ (μM) | N | CC$_{50}$ (μM) | N | SI | N |
|---|---|---|---|---|---|---|
| 1 | 0.0020 | 6 | 9.9 | 6 | 4879 | 6 |
| 1A* | 0.00088 | 5 | 5.9 | 5 | 6654 | 5 |
| 1B | 0.050 | 3 | 12 | 3 | 283 | 3 |
| 2 | 0.0013 | 3 | 8.0 | 3 | 6338 | 3 |
| 2A* | 0.00077 | 5 | 6.1 | 5 | 7834 | 5 |
| 2B | 0.055 | 7 | 8.0 | 7 | 146 | 7 |
| 3 | 0.00058 | 4 | 7.2 | 4 | 10845 | 4 |
| 3A* | 0.00030 | 5 | 4.8 | 4 | 17249 | 4 |
| 3B | 0.032 | 4 | 11 | 4 | 324 | 4 |
| 4 | 0.0011 | 4 | 6.6 | 4 | 6211 | 4 |
| 4A* | 0.0005 | 6 | 4.4 | 5 | 8726 | 5 |
| 4B | 0.018 | 4 | 16 | 4 | 814 | 4 |
| 5 | 0.0020 | 3 | 24 | 4 | 10164 | 3 |
| 5A | 0.070 | 3 | 24 | 3 | 530 | 3 |
| 5B* | 0.0010 | 4 | >13 | 3 | 14546 | 3 |
| 6A* | 0.0027 | 3 | 5.0 | 3 | 1887 | 3 |
| 6B | 0.20 | 3 | 12 | 3 | 67 | 3 |
| 7 | 0.0015 | 3 | 5.0 | 3 | 3411 | 3 |
| 7A* | 0.00076 | 4 | 4.4 | 4 | 5733 | 4 |
| 7B | 0.043 | 3 | 9.6 | 4 | 216 | 3 |
| 8 | 0.0028 | 3 | 7.6 | 3 | 2710 | 3 |
| 8A* | 0.0010 | 3 | 5.1 | 3 | 5071 | 3 |
| 8B | 0.24 | 3 | 11 | 3 | 45 | 3 |
| 9 | 0.0016 | 3 | 8.8 | 3 | 5457 | 3 |
| 9A* | 0.0011 | 3 | 4.8 | 3 | 4398 | 3 |
| 9B | 0.098 | 3 | 21 | 3 | 212 | 3 |
| 10 | 0.0011 | 3 | 7.8 | 3 | 7070 | 3 |
| 10A | 0.054 | 4 | 18 | 4 | 550 | 4 |
| 10B* | 0.00067 | 6 | 4.5 | 6 | 6770 | 6 |
| 11 | 0.0030 | 3 | 12 | 3 | 4058 | 3 |
| 11A* | 0.0011 | 3 | 6.6 | 3 | 6248 | 3 |
| 11B | 0.055 | 3 | >25 | 3 | >1617 | 3 |
| 12 | 0.00060 | 4 | >25 | 4 | >65542 | 4 |
| 12A* | 0.00042 | 3 | >25 | 3 | >36121 | 3 |
| 12B | 0.021 | 3 | >25 | 4 | >1373 | 3 |
| 13 | 0.0014 | 3 | 7.6 | 3 | 5298 | 3 |
| 13A | 0.017 | 7 | 9.5 | 7 | 484 | 6 |
| 13B* | 0.0011 | 4 | 6.7 | 4 | 6211 | 4 |
| 14 | 0.0015 | 3 | 5.3 | 4 | 3360 | 3 |
| 14A* | 0.00044 | 4 | 3.4 | 3 | 8101 | 3 |
| 14B | 0.041 | 3 | 11 | 3 | 262 | 3 |
| 15 | 0.0015 | 3 | 7.8 | 3 | 5240 | 3 |
| 15A* | 0.00080 | 3 | 5.4 | 3 | >4057 | 3 |
| 15B | 0.073 | 3 | 17 | 3 | 196 | 3 |
| 16 | 0.00066 | 3 | 8.8 | 3 | 13287 | 3 |
| 16A* | 0.00042 | 5 | 3.7 | 7 | 8049 | 5 |
| 16B | 0.013 | 3 | 22 | 3 | 1692 | 3 |
| 17 | 0.00024 | 6 | 3.5 | 7 | 19799 | 6 |

TABLE 1-continued

EC$_{50}$, CC$_{50}$, and SI for the compounds of the invention in the DENV-2 antiviral assay

| compound# | EC$_{50}$ (μM) | N | CC$_{50}$ (μM) | N | SI | N |
|---|---|---|---|---|---|---|
| 17A | 0.038 | 3 | 14 | 3 | 353 | 3 |
| 17B* | 0.00020 | 5 | 3.6 | 5 | >27559 | 5 |
| 18 | 0.00025 | 5 | 3.3 | 8 | >15249 | 5 |
| 18A* | 0.000086 | 6 | 3.1 | 7 | >28953 | 6 |
| 18B | 0.0092 | 3 | 10 | 3 | 1132 | 3 |

N = the number of independent experiments in which the compounds were tested.

Tetravalent Reverse Transcriptase Quantitative-PCR (RT-qPCR) Assay: Protocol A.

The antiviral activity of the compounds of the invention was tested against DENV-1 strain TC974#666 (NCPV; Table 6), DENV-2 strain 16681 (Table 7), DENV-3 strain H87 (NCPV; Table 8) and DENV-4 strains H241 (NCPV; Table 9) in a RT-qPCR assay. Therefore, Vero cells were infected with either DENV-1, or -2, or -3, or -4 in the presence or absence of test compounds. At day 3 post-infection, the cells were lysed and cell lysates were used to prepare cDNA of both a viral target (the 3'UTR of DENV; table 2) and a cellular reference gene (β-actin, table 2). Subsequently, a duplex real time PCR was performed on a Lightcycler480 instrument. The generated Cp value is inversely proportional to the amount of RNA expression of these targets. Inhibition of DENV replication by a test compound result in a shift of Cp's for the 3'UTR gene. On the other hand, if a test compound is toxic to the cells, a similar effect on β-actin expression will be observed. The comparative ΔΔCp method is used to calculate EC$_{50}$, which is based on the relative gene expression of the target gene (3'UTR) normalized with the cellular housekeeping gene (β-actin).

concentration range: 25 μM-0.00038 μM). In addition, each plate contains wells which are assigned as virus controls (containing cells and virus in the absence of compound) and cell controls (containing cells in the absence of virus and compound). Once the cells were added in the plates, the plates were incubated in a fully humidified incubator (37° C., 5% CO$_2$) until the next day. Then, DENV-1 strain TC974#666 at an MOI of 0.6, DENV-2 strain 16681 at an MOI of 0.01, DENV-3 strain H87 at an MOI of 1.0 and DENV-4 strains H241 at an MOI of 0.2 and SG/06K2270DK1/2005 at an MOI of 0.16, were added. Therefore, 25 μL of virus suspension was added to all the wells containing test compound and to the wells assigned as virus control. In parallel, 25 μL of culture medium was added to the cell controls. Next, the plates were incubated for 3 days in a fully humidified incubator (37° C., 5% CO$_2$). After 3 days, the supernatant was removed from the wells and the cells were washed twice with ice-cold PBS (~100 μL). The cell pellets within the 96-well plates were stored at −80° C. for at least 1 day. Next, RNA was extracted using the Cells-to-CT™ lysis kit, according to the manufacture's guideline (Applied Biosystems). The cell lysates can be stored at −80° C. or immediately used in the reverse transcription step.

In preparation of the reverse transcription step, mix A (table 3A) was prepared and 7.57 μL/well was dispensed in a 96-well plate. After addition of 5 μL of the cell lysates, a five minute denaturation step at 75° C. was performed (table 3B). Afterwards, 7.43 μL of mix B was added (table 3C) and the reverse transcription step was initiated (table 3D) to generate cDNA.

TABLE 2

Primers and probes used for the real-time, quantitative RT-PCR.

| Primer/probe | Target | Sequence[a,b] |
|---|---|---|
| F3utr258 | DENV 3'-UTR | 5'-CGGTTAGAGGAGACCCCTC-3' |
| R3utr425 | DENV 3'-UTR | 5'-GAGACAGCAGGATCTCTGGTC-3' |
| P3utr343 | DENV 3'-UTR | *FAM*-5'-AAGGACTAGAGGTTAGAGGAGACCCCCC-3'-*BHQ1* |
| Factin743 | β-actin | 5'-GGCCAGGTCATCACCATT-3' |
| Ractin876 | β-actin | 5'-ATGTCCACGTCACACTTCATG-3' |
| Pactin773 | β-actin | *HEX*-5'-TTCCGCTGCCCTGAGGCTCTC-3'-*BHQ1* |

[a]Reporter dyes (FAM, HEX) and quencher (BHQ1) elements are indicated in bold and italics.
[b]The nucleotide sequence of the primers and probes were selected from the conserved region in the 3'UTR region of the dengue virus genome, based on the alignment of 300 nucleotide sequences of the four dengue serotypes deposited in Genbank (Gong et al., 2013, Methods Mol Biol, Chapter 16).

The culture medium consisted of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 75 μL/well was added in 96-well plates (10000 cells/well), which already contain the antiviral compounds. Typically, these plates contain a 4-fold serial dilution of 9 dilution steps of the test compound at 200 times the final concentration in 100% DMSO (500 nL; final Finally, a RT-qPCR mix was prepared, mix C (table 4A), dispensed in 96-well LightCycler qPCR plates to which 3 μL of cDNA was added and the qPCR was performed according to the conditions in table 4B on a LightCycler 480. Using the LightCycler software and an in-house LIMS system, dose response curves for each compound were calculated and the half maximal effective concentration (EC$_{50}$) and the half maximal cytotoxic concentration (CC$_{50}$) were determined.

TABLE 3 cDNA synthesis using Mix A, denaturation, Mix B and reverse transcription.

A Mix A

Plates 8
Samples 828    Reaction Vol. (µl) 20

| Mix Item | Unit | Concentration Stock | Final | Volume for (µl) 1 sample | x samples |
|---|---|---|---|---|---|
| Milli-Q H$_2$O | | | | 7.27 | 6019.56 |
| R3utr425 | µM | 20 | 0.27 | 0.15 | 124.20 |
| Ractin876 | µM | 20 | 0.27 | 0.15 | 124.20 |
| Volume mix/well (µl) | | | | 7.57 | |
| Cell lysates | | | | 5.00 | |

B Denaturation step:

| Step | Temp | Time |
|---|---|---|
| Denaturation | 75° C. | 5' |
| Hold | 4° C. | hold |

C Mix B

Samples 864

| Mix Item | Unit | Concentration Stock | Final | Volume for (µl) 1 sample | x samples |
|---|---|---|---|---|---|
| Expand HIFI buffer 2 | X | 10.00 | 1.00 | 2.00 | 1728.0 |
| MgCl$_2$ | mM | 25.00 | 3.50 | 2.80 | 2419.2 |
| dNTPs | mM | 10.00 | 1.00 | 2.00 | 1728.0 |
| Rnase inhibitor | U/µl | 40.00 | 1.00 | 0.50 | 432.0 |
| Expand RT | U/µl | 50.00 | 0.33 | 0.13 | 112.3 |
| Total Volume Mix (µl) | | | | 7.43 | |

D Protocol cDNA synthesis

| Step | Temp | Time |
|---|---|---|
| Rev transc | 42° C. | 30' |
| Denaturation | 99° C. | 5' |
| Hold | 4° C. | hold |

TABLE 4 qPCR mix and protocol.

A Mix C

Samples 833    Reaction Vol. (µl) 25

| Mix Item | Unit | Concentration Stock | Final | Volume for (µl) 1 sample | x samples |
|---|---|---|---|---|---|
| H$_2$O PCR grade Roche | | | | 7.74 | 6447.42 |
| Roche 2xMM mix | X | 2 | 1 | 12.50 | 10412.50 |
| F3utr258 | µM | 20 | 0.3 | 0.38 | 316.54 |
| R3utr425 | µM | 20 | 0.3 | 0.38 | 316.54 |
| P3utr343 | µM | 20 | 0.1 | 0.13 | 108.29 |
| Factin743 | µM | 20 | 0.3 | 0.38 | 316.54 |
| Ractin876 | µM | 20 | 0.3 | 0.38 | 316.54 |

TABLE 4-continued qPCR mix and protocol.

| | | | | | |
|---|---|---|---|---|---|
| Pactin773 | µM | 20 | 0.1 | 0.13 | 108.29 |
| Volume Mix/Tube (µl) | | | | 22.02 | |
| cDNA | | | | 3.00 | |

B Protocol qPCR3

| Step | Temp | Time | Ramp rate | |
|---|---|---|---|---|
| preincub/denat | 95° C. | 10 min | 4.4 | |
| Denaturation | 95° C. | 10 sec | 4.4 | 40 cycles |
| annealing | 58° C. | 1 min | 2.2 | |
| Elongation | 72° C. | 1 sec | 4.4 | |
| Cooling | 40° C. | 10 sec | 1.5 | |

TABLE 6

EC$_{50}$, CC$_{50}$, and SI for the compounds against serotype 1 in the RT-qPCR assays Protocol A
RT-qPCR serotype 1 TC974#666

| compound# | EC$_{50}$ (µM) | N | CC$_{50}$ (µM) | N | SI | N |
|---|---|---|---|---|---|---|
| 1A | 0.00518 | 6 | 3.52 | 6 | 642 | 6 |
| 2A | 0.005853 | 3 | 2.92 | 3 | 474 | 3 |
| 3A | 0.007178 | 3 | 3.91 | 3 | 545 | 3 |
| 4A | 0.004217 | 3 | 3.59 | 3 | 851 | 3 |
| 5B | 0.008894 | 4 | 8.38 | 4 | 928 | 4 |
| 6A | 0.009698 | 3 | 4.61 | 3 | 476 | 3 |
| 7A | 0.003703 | 3 | 3.87 | 3 | 904 | 3 |
| 8A | 0.006835 | 3 | 4.4 | 3 | 644 | 3 |
| 9A | 0.01 | 3 | 4.04 | 3 | 402 | 3 |
| 10B | 0.004463 | 3 | 5.14 | 3 | 921 | 3 |
| 11A | 0.0109 | 3 | 4.38 | 3 | 402 | 3 |
| 12A | 0.014 | 3 | >10.00 | 3 | >870 | 3 |
| 13B | | | | | | |
| 14A | 0.001402 | 4 | 2.42 | 3 | 1682 | 3 |
| 15A | 0.003513 | 1 | >2.50 | 1 | >712 | 1 |
| 16A | 0.003264 | 4 | 3.17 | 4 | 970 | 4 |
| 17B | 0.000478 | 4 | 1.61 | 4 | 2960 | 3 |
| 18A | 0.000357 | 3 | 3.01 | 4 | 7331 | 3 |

N = the number of independent experiments in which the compounds were tested.
NA: not approved.
ND: not determined.

TABLE 7

EC$_{50}$, CC$_{50}$, and SI for the compounds against serotype 2 in the RT-qPCR assays Protocol A
RT-qPCR serotype 2 16681

| compound# | EC$_{50}$ (µM) | N | CC$_{50}$ (µM) | N | SI | N |
|---|---|---|---|---|---|---|
| 1A | 0.00083 | 6 | 3.84 | 6 | 4303 | 6 |
| 2A | 0.000856 | 4 | 3.84 | 4 | 4858 | 4 |
| 3A | 0.000285 | 4 | 4.35 | 8 | 20905 | 5 |
| 4A | 0.000377 | 5 | 4.63 | 5 | 12281 | 5 |
| 5B | 0.001231 | 3 | 7.24 | 3 | 5868 | 3 |
| 6A | 0.003482 | 3 | 4.44 | 3 | 1274 | 3 |
| 7A | 0.000525 | 3 | 5.64 | 2 | 7689 | 2 |
| 8A | 0.001274 | 3 | 5.34 | 3 | 4191 | 3 |
| 9A | 0.001135 | 3 | 5.33 | 3 | 4693 | 3 |
| 10B | 0.000605 | 4 | 4.39 | 4 | 6630 | 4 |
| 11A | 0.001091 | 3 | 4.96 | 3 | 4543 | 3 |
| 12A | 0.00025 | 3 | >12.12 | 3 | >42176 | 3 |
| 13B | 0.000675 | 1 | 3.71 | 1 | 5492 | 1 |
| 14A | 0.000567 | 3 | 3.54 | 4 | 4710 | 2 |
| 15A | 0.001021 | 2 | 4.62 | 2 | 4357 | 2 |

TABLE 7-continued $EC_{50}$, $CC_{50}$, and SI for the compounds against serotype 2 in the RT-qPCR assays Protocol A
RT-qPCR serotype 2 16681

| compound# | $EC_{50}$ (μM) | N | $CC_{50}$ (μM) | N | SI | N |
|---|---|---|---|---|---|---|
| 16A | 0.000188 | 4 | 4.35 | 5 | 19958 | 4 |
| 17B | 9.21E−05 | 4 | 2.51 | 5 | 21074 | 3 |
| 18A | 0.00014 | 3 | 3.2 | 4 | 20747 | 2 |

N = the number of independent experiments in which the compounds were tested.
NA: not approved.
ND: not determined.

TABLE 8

$EC_{50}$, $CC_{50}$, and SI for the compounds against serotype 3 in the RT-qPCR assays Protocol A
RT-qPCR serotype 3 H87

| compound# | EC50 (μM) | N | CC50 (μM) | N | SI | N |
|---|---|---|---|---|---|---|
| 1A | 0.0496 | 6 | 2.47 | 5 | 50 | 5 |
| 2A | 0.0584 | 3 | 3.04 | 3 | 57 | 3 |
| 3A | 0.0586 | 3 | 3.05 | 3 | 52 | 3 |
| 4A | 0.0553 | 3 | 2.61 | 3 | 47 | 3 |
| 5B | 0.1001 | 4 | 3.05 | 3 | 28 | 3 |
| 6A | 0.1233 | 3 | 4.79 | 2 | 43 | 2 |
| 7A | 0.0616 | 3 | 3.3 | 3 | 48 | 3 |
| 8A | 0.0821 | 3 | 3.93 | 3 | 48 | 3 |
| 9A | 0.104 | 3 | 3.56 | 3 | 34 | 3 |
| 10B | 0.0554 | 3 | 3.24 | 2 | 45 | 2 |
| 11A | 0.093 | 3 | 4.84 | 3 | 52 | 3 |
| 12A | 0.0738 | 4 | 5.6 | 3 | 76 | 3 |
| 13B | | | | | | |
| 14A | 0.0131 | 3 | 2.72 | 3 | 241 | 3 |
| 15A | 0.0221 | 1 | | | | |
| 16A | 0.0254 | 3 | 4.17 | 3 | 164 | 3 |

TABLE 8-continued $EC_{50}$, $CC_{50}$, and SI for the compounds against serotype 3 in the RT-qPCR assays Protocol A
RT-qPCR serotype 3 H87

| compound# | EC50 (μM) | N | CC50 (μM) | N | SI | N |
|---|---|---|---|---|---|---|
| 17B | 0.007281 | 3 | 1.98 | 3 | 272 | 3 |
| 18A | 0.007543 | 3 | 2.52 | 3 | 333 | 3 |

N = the number of independent experiments in which the compounds were tested.
NA: not approved;
ND: not determined.

TABLE 9

$EC_{50}$ $CC_{50}$, and SI for the compounds against serotype 4 in the RT-qPCR assays Protocol A
RT-qPCR serotype 4 H241

| compound# | EC50 (μM) | N | CC50 (μM) | N | SI | N |
|---|---|---|---|---|---|---|
| 1A | 0.1652 | 7 | 2.93 | 7 | 17 | 7 |
| 2A | 0.1225 | 4 | 2.49 | 3 | 16 | 3 |
| 3A | 0.1211 | 7 | 2.27 | 7 | 19 | 7 |
| 4A | 0.1308 | 4 | 3.18 | 4 | 24 | 4 |
| 5B | 0.1864 | 4 | 5.48 | 4 | 27 | 4 |
| 6A | 0.2393 | 3 | 2.7 | 3 | 11 | 3 |
| 7A | 0.1416 | 4 | 2.88 | 4 | 18 | 4 |
| 8A | 0.2482 | 5 | 3.55 | 5 | 14 | 5 |
| 9A | 0.2409 | 3 | 3.39 | 3 | 14 | 3 |
| 10B | 0.1093 | 4 | 2.97 | 4 | 26 | 4 |
| 11A | 0.2256 | 3 | 3.51 | 3 | 16 | 3 |
| 12A | 0.2611 | 4 | >17.15 | 3 | >111 | 3 |
| 13B | 0.2301 | 1 | 2.6 | 1 | 11 | 1 |
| 14A | 0.0694 | 5 | 1.97 | 4 | 27 | 4 |
| 15A | 0.091 | 2 | 3.75 | 1 | 40 | 1 |
| 16A | 0.0801 | 5 | 3.16 | 5 | 38 | 5 |
| 17B | 0.0213 | 5 | 1.8 | 4 | 91 | 4 |
| 18A | 0.0182 | 5 | 1.89 | 4 | 130 | 4 |

N = the number of independent experiments in which the compounds were tested.
NA: not approved.

The invention claimed is:

1. A compound of formula (I)

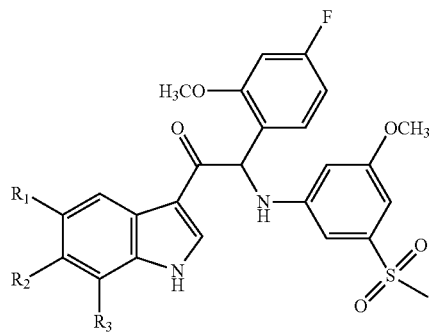

wherein:

R₁ is F, R₂ is F, CH₃ or OCH₃ and R₃ is H,
R₁ is H, R₂ is Cl or F and R₃ is CH₃,
R₁ is CH₃, R₂ is OCH₃, F or H and R₃=H,
R₁ is H, R₂ is Cl or F and R₃ is H,
R₁ is CH₃, R₂ is H and R₃ is F,
R₁ is F, R₂ is H and R₃ is CH₃,
R₁ is H, R₂ is OCH₃ and R₃ is H or Cl,
R₁ is H, R₂ is F and R₃ is F,
R₁ is CF₃ or OCF₃, R₂ is H and R₃ is H,
R₁ is Cl, R₂ is OCH₃ and R₃ is H;

and a stereo-isomeric form, a pharmaceutically acceptable salt, solvate or polymorph thereof.

2. A compound of claim 1 selected from the group consisting of:

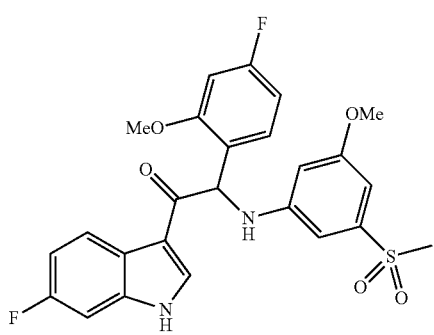

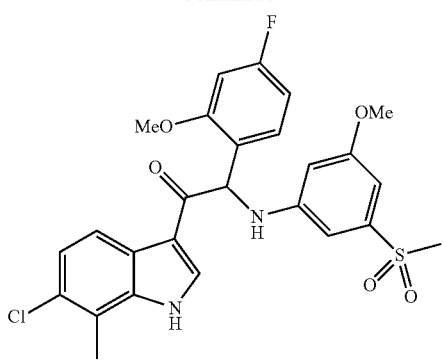

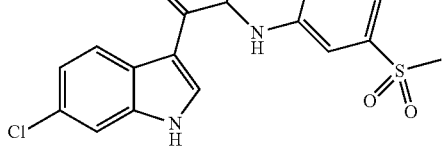

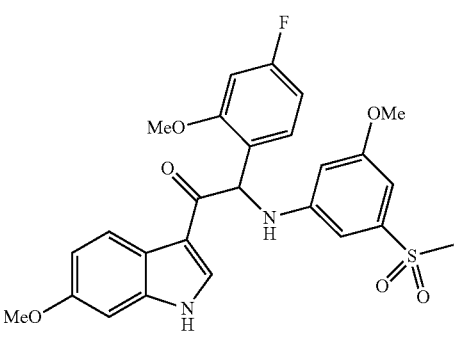

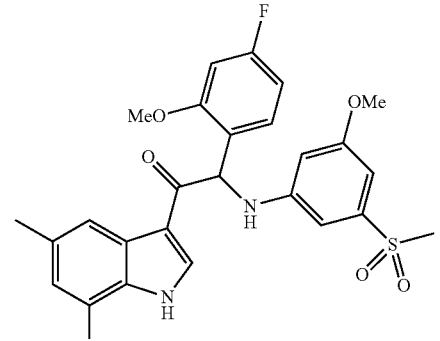

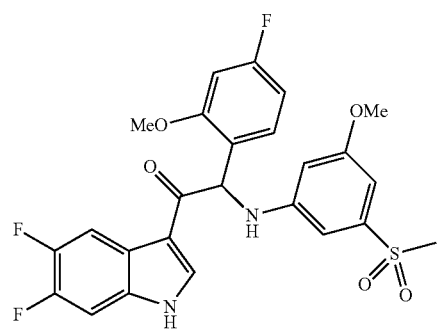

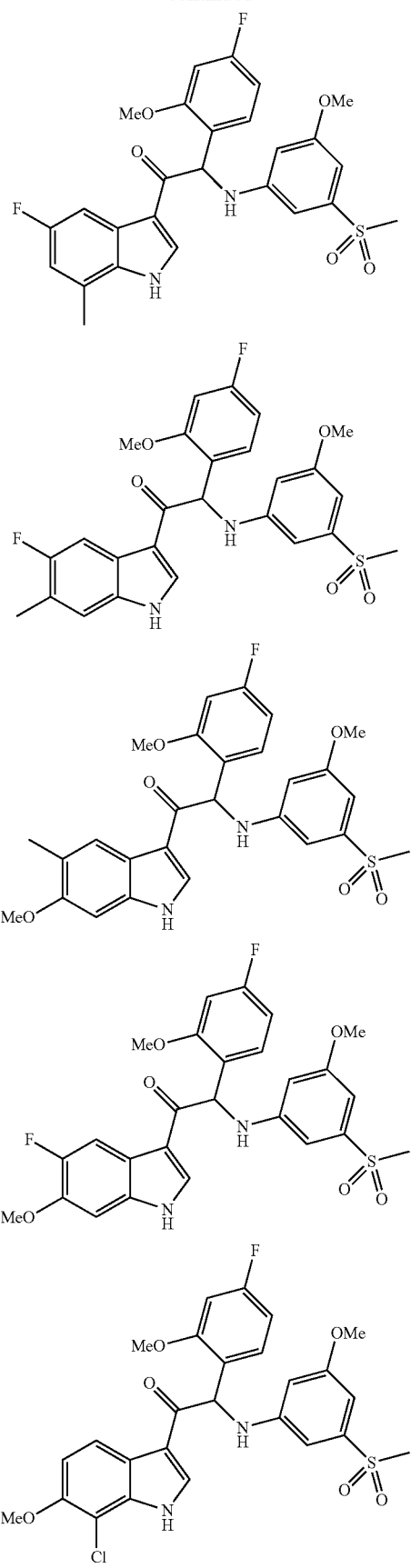
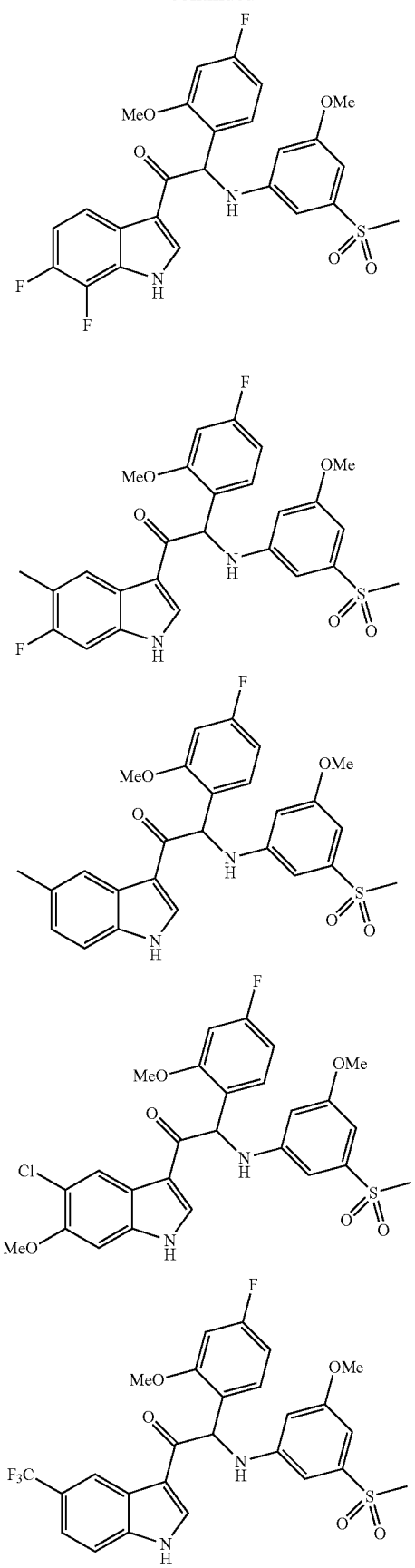

-continued

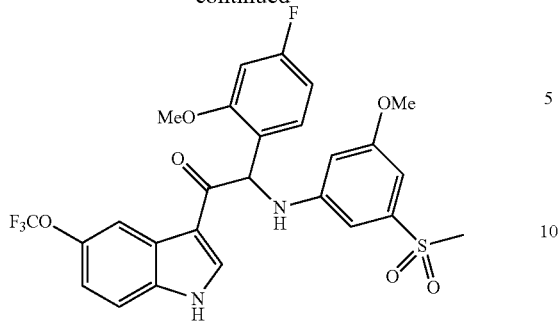

and a stereo-isomeric form, a pharmaceutically acceptable salt, solvate or polymorph thereof.

3. A pharmaceutical composition comprising a compound of claim 1 together with one or more pharmaceutically acceptable excipients, diluents or carriers.

4. A method of inhibiting the replication of dengue virus in a biological sample or patient, comprising administering to said sample or patient a dengue virus replication-inhibiting amount of the compound of claim 1.

5. The method of claim 4, further comprising administering an additional therapeutic agent.

* * * * *